(12) United States Patent
Bobilev et al.

(10) Patent No.: US 11,926,665 B2
(45) Date of Patent: *Mar. 12, 2024

(54) METHODS OF TREATING CANCER WITH ANTI-TIM-3 ANTIBODIES

(71) Applicant: TESARO, INC., Waltham, MA (US)

(72) Inventors: Dmitri Bobilev, Waltham, MA (US); Andrew R. Ferguson, Waltham, MA (US); Kristen Anne McEachern, Waltham, MA (US); Jing Wang, Waltham, MA (US)

(73) Assignee: TESARO, INC., Waltham, MA (US)

( * ) Notice: Subject to any disclaimer, the term of this patent is extended or adjusted under 35 U.S.C. 154(b) by 397 days.

This patent is subject to a terminal disclaimer.

(21) Appl. No.: 16/476,534

(22) PCT Filed: Jan. 9, 2018

(86) PCT No.: PCT/US2018/013021
§ 371 (c)(1),
(2) Date: Jul. 8, 2019

(87) PCT Pub. No.: WO2018/129553
PCT Pub. Date: Jul. 12, 2018

(65) Prior Publication Data
US 2019/0322746 A1 Oct. 24, 2019

Related U.S. Application Data

(60) Provisional application No. 62/444,354, filed on Jan. 9, 2017, provisional application No. 62/582,272, filed on Nov. 6, 2017.

(51) Int. Cl.
| | | |
|---|---|---|
| *A61K 39/00* | (2006.01) | |
| *A61K 9/00* | (2006.01) | |
| *A61P 35/00* | (2006.01) | |
| *C07K 16/28* | (2006.01) | |

(52) U.S. Cl.
CPC ........ *C07K 16/2803* (2013.01); *A61K 9/0019* (2013.01); *A61P 35/00* (2018.01); *C07K 16/2818* (2013.01); *A61K 2039/505* (2013.01); *A61K 2039/507* (2013.01); *A61K 2039/545* (2013.01); *C07K 2317/24* (2013.01); *C07K 2317/76* (2013.01); *C07K 2317/94* (2013.01)

(58) Field of Classification Search
CPC ............................................... A61K 2039/505
See application file for complete search history.

(56) References Cited

U.S. PATENT DOCUMENTS

| | | | |
|---|---|---|---|
| 4,828,981 A | 5/1989 | Maddio | |
| 5,122,464 A | 6/1992 | Wilson et al. | |
| 5,464,758 A | 11/1995 | Gossen et al. | |
| 5,770,359 A | 6/1998 | Wilson et al. | |
| 5,814,618 A | 9/1998 | Bujard et al. | |
| 6,843,987 B2 | 1/2005 | Debets et al. | |
| 7,112,715 B2 | 9/2006 | Chambon et al. | |
| 8,008,449 B2 | 8/2011 | Korman et al. | |
| 8,034,771 B2 | 10/2011 | Sims et al. | |
| 8,101,176 B2 | 1/2012 | Kuchroo et al. | |
| 8,168,757 B2 | 5/2012 | Finnefrock et al. | |
| 8,481,021 B2 | 7/2013 | Sims et al. | |
| 8,552,156 B2 | 10/2013 | Takayanagi et al. | |
| 8,568,992 B2 | 10/2013 | Walker et al. | |
| 8,841,418 B2 | 9/2014 | Karsunky et al. | |
| 8,871,192 B2 | 10/2014 | Sims et al. | |
| 9,023,995 B2 | 5/2015 | Brown et al. | |
| 10,472,419 B2 * | 11/2019 | Sabatos-Peyton | ...... A61P 37/02 |
| 10,508,149 B2 * | 12/2019 | Kehry | ...... A61P 37/00 |
| 10,981,990 B2 * | 4/2021 | Sabatos-Peyton | ...... C07K 16/2803 |
| 11,352,427 B2 | 6/2022 | Kehry et al. | |
| 2003/0103985 A1 | 6/2003 | Adolf et al. | |
| 2006/0134105 A1 | 6/2006 | Lazar et al. | |
| 2008/0193465 A1 | 8/2008 | Dimitrov et al. | |
| 2009/0093002 A1 | 4/2009 | Pfeifer et al. | |
| 2009/0093024 A1 | 4/2009 | Bowers et al. | |
| 2011/0159011 A1 | 6/2011 | Carrier et al. | |
| 2011/0287485 A1 | 11/2011 | Bowers et al. | |
| 2012/0189617 A1 | 7/2012 | Takayanagi et al. | |
| 2012/0258495 A1 | 10/2012 | Gallo et al. | |
| 2013/0022623 A1 | 1/2013 | Karsunky et al. | |
| 2013/0156774 A1 | 6/2013 | Kuchroo et al. | |
| 2013/0236471 A1 | 9/2013 | Brown et al. | |
| 2013/0336982 A1 | 12/2013 | Mader et al. | |
| 2014/0234330 A1 | 8/2014 | Budelsky et al. | |
| 2014/0271627 A1 | 9/2014 | Puro | |
| 2014/0294834 A1 | 10/2014 | Harms et al. | |
| 2015/0017123 A1 | 1/2015 | Sims et al. | |

(Continued)

FOREIGN PATENT DOCUMENTS

| | | |
|---|---|---|
| CN | 101516911 | 8/2009 |
| CN | 105209497 | 12/2015 |

(Continued)

OTHER PUBLICATIONS

Nielsen et al. (Cell Immunol. Jun. 2005; 235 (2): 109-16).*
Winkler et al. (J. Immunol. Oct. 15, 2000; 165 (8): 4505-4514).*
Chang et al. (Structure. Jan. 7, 2014; 22 (1): 9-21).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*

(Continued)

*Primary Examiner* — Stephen L Rawlings
(74) *Attorney, Agent, or Firm* — Shan Liu

(57) ABSTRACT

The present disclosure provides methods of administering certain TIM-3 binding agents to patients having cancer. Dosage regimens for compositions comprising a TIM-3 binding agent are also explicitly provided.

13 Claims, 12 Drawing Sheets

Specification includes a Sequence Listing.

(56) References Cited

U.S. PATENT DOCUMENTS

| | | |
|---|---|---|
| 2015/0203584 A1 | 7/2015 | Brown et al. |
| 2015/0218274 A1 | 8/2015 | Sabatos-Peyton et al. |
| 2016/0137708 A1 | 5/2016 | Sims et al. |
| 2017/0121409 A1 | 5/2017 | Verona et al. |
| 2017/0190777 A1* | 7/2017 | Sabatos-Peyton ........ A61P 1/04 |
| 2018/0127500 A1 | 5/2018 | Kehry et al. |
| 2019/0276533 A1 | 9/2019 | Zhang et al. |
| 2019/0284280 A1 | 9/2019 | King et al. |
| 2020/0148770 A1 | 5/2020 | Kehry et al. |
| 2020/0164084 A1* | 5/2020 | Cortez ................ A61K 31/52 |
| 2022/0169734 A1 | 6/2022 | King et al. |
| 2022/0363759 A1 | 11/2022 | Kehry et al. |

FOREIGN PATENT DOCUMENTS

| | | |
|---|---|---|
| JP | 2005-523018 A | 8/2005 |
| WO | WO 1992/008796 | 5/1992 |
| WO | WO 1994/028143 | 12/1994 |
| WO | WO 2003/063792 | 8/2003 |
| WO | WO 2005/012524 | 2/2005 |
| WO | WO 2008/084261 | 7/2008 |
| WO | WO 2008/156712 | 12/2008 |
| WO | WO 2009/087381 | 7/2009 |
| WO | WO 2011/155607 | 12/2011 |
| WO | WO 2013/006490 | 1/2013 |
| WO | WO 2013/098420 | 7/2013 |
| WO | WO 2014/140240 | 9/2014 |
| WO | WO 2014/179664 | 11/2014 |
| WO | WO2015/117002 A1 | 8/2015 |
| WO | WO 2015/138920 | 9/2015 |
| WO | WO 2016/068802 | 5/2016 |
| WO | WO 2016/071448 | 5/2016 |
| WO | WO 2016/126858 | 9/2016 |
| WO | WO2016/161270 A1 | 10/2016 |
| WO | WO 2017/019894 | 11/2017 |
| WO | WO 2017/193032 | 11/2017 |
| WO | WO 2018/005818 | 1/2018 |
| WO | WO 2018/129553 | 7/2018 |

OTHER PUBLICATIONS

De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Ingram et al. (Proc. Natl. Acad. Sci. USA. Apr. 10, 2018; 115 (15): 3912-3917).*
Bell et al. (Cancer Genome Atlas Research Network) (Nature. Jun. 29, 2011; 474 (7353): 609-15).*
Anderson (Cancer Immunol. Res. 2014; 2 (5): 393-8).*
Sun et al. (J. Immunother. Cancer. May 2020; 8 (1): e000294; pp. 1-12).*
Sakuishi et al. (J. Exp. Med. Sep. 27, 2010; 207 (10): 2187-94).*
Liu et al. (J. Immunother. May 2016; 39 (4): 171-80).*
Harding et al. (Clin. Cancer Res. Apr. 15, 2021; 27 (8): 2168-2178).*
Takashima et al. (Sci. Rep. Jul. 10, 2019; 9 (1): 10004; pp. 1-13).*
Bailly et al. (Biochem, Pharmacol. Mar. 2023; 209: 115445; pp. 1-14).*
ClinicalTrials.gov Identifier: NCT03307785 (first posted Oct. 12, 2017) (pp. 1-52).*
Yap et al. (J. Immunother. Cancer. Mar. 2022; 10 (3): e003924; pp. 1-11).*
ClinicalTrials.gov Identifier: NCT03680508 (first posted Sep. 21, 2018) (pp. 1-10).*
Acoba et al. (J. Clin. Oncol. Feb. 1, 2023; 41 (4 Suppl.): 580; p. 1).*
ClinicalTrials.gov Identifier: NCT02817633 (first posted Sep. 21, 2018) (pp. 1-13).*
Falchook et al. (J. Clin. Oncol. Feb. 1, 2023; 41 (4 Suppl.): 580; p. 1).*
Hollebecque et al. (Clin. Cancer Res. Dec. 1, 2021; 27 (23):6393-6404).*
Kim et al. (Clin. Cancer Res. Jan. 1, 2017; 23 (1): 124-136).*
Murtaza et al. (Eur. J. Cancer. Nov. 29, 2016; 69 (Suppl. 1): S102; p. 1).*
Gomes de Morais et al. (Curr. Oncol. Rep. May 2022; 24 (5): 651-658).*
Acharya et al. (J. Immunother. Cancer. Jun. 2020; 8 (1): e000911; pp. 1-11).*
Altschul et al., "Basic local alignment search tool," J. Molecular Biol., 1990, 215(3):403-410.
Altschul et al., "Gapped BLAST and PSI-BLAST: a new generation of protein database search programs," Nucleic Acids Res., 1997, 25(17):3389-3402.
Anderson et al., "Promotion of tissue inflammation by the immune receptor Tim-3 expressed on innate immune cells ," Science, 2007, 318:1141-1143.
Anderson et al., "TIM-3 in autoimmunity," Curr Opin Immunol., 2006, 18:665-669.
Ayers et al., "IFN-γ-related mRNA profile predicts clinical response to PD-1 blockade," J Clin Invest., 2017, 127(8):2930-2940, 2017.
Baitsch et al., "Extended Co-Expression of Inhibitory Receptors by Human CD8 T-Cells Depending on Differentiation, Antigen-Specificity and Anatomical Localization," PLoS ONE, 2012, 7:e30852.
Beigert et al., "Sequence context-specific profiles for homology searching, " Proc. Natl. Acad Sci. USA, 2009, 106(10):3770-3775.
Bhatia et al., "Immunobiology of Merkel cell carcinoma: implications for immunotherapy of a polyomavirus-associated cancer," Curr Oncol Rep., 2011, 13(6):488-497.
Bird et al., "Single-chain antigen-binding proteins," Science, 1988, 242:423-426 (1988).
Blumberg et al., "IL-1RL2 and its ligands contribute to the cytokine network in psoriasis," J. Immunol., 2010, 185(7):4354-4362.
Blumberg et al., "Opposing activities of two novel members of the IL-1 ligand family regulate skin inflammation," J. Exp. Med., 2007, 204(11): 2603-2614.
Bohnsack et al., "Adaptation of the immune-related response criteria: irRecist," ESMO, 2014, Abstract 4958.
Bowers et al., "Coupling mammalian cell surface display with somatic hypermutation for the discovery and maturation of human antibodies," Proc. Natl. Acad. Sci. USA, 2011, 108(51):20455-20460.
Braitbard et al., "Competition between bound and free peptides in an ELISA-based procedure that assays peptides derived from protein digests," Proteome Science., 2006, 4(12):1-14.
Brash et al., "Strontium phosphate transfection of human cells in primary culture: stable expression of the simian virus 40 large-T-antigen gene in primary human bronchial epithelial cells," Mol. Cell Biol., 1987, 7:2031-2034.
Brown et al., "Tolerance to single, but not multiple, amino acid replacements in antibody V CDR2: a means of minimizing B cell wastage from somatic hypermutation?" J of Immunol., 1996, 156:3285-3291.
Burkhart et al., "Peptide-induced T cell regulation of experimental autoimmune encephalomyelitis: a role for IL-10," Int bnmunol., 1999, 11:1625-1634.
Chiba et al., "Tumor-infiltrating DCs suppress nucleic acid-mediated innate immune responses through interactions between the receptor TIM-3 and the alarmin HMGB1," Nature Immunology, 2012, 13: 832-842.
Clayton et al., "T Cell Ig and Mucin Domain-Containing Protein 3 Is Recruited to the Immune Synapse, Disrupts Stable Synapse Formation, and Associates with Receptor Phosphatases," J Immunol., 2014, 192(2):782-791.
Colbere-Garapin et al., "A new dominant hybrid selective marker for higher eukarvotic cells." J. Molecular Biol., 1981, 150(1):1-14.
Conese et al., "Gene therapy progress and prospects: episomally maintained self-replicating systems," Gene Therapy, 2004, 11:1735-1742.
David et al., "Protein iodination with solid state lactoperoxidase," Biochemistry, 1974, 13:1014-1021.

(56) References Cited

OTHER PUBLICATIONS

Davies et al. "Antibody-Antigen Complexes," Annual Rev Biochem., 1990, 59:439-473.
De Waal et al., "Pustulosis palmopiantaris is a disease distinct from psoriasis" J. Dermatoloaical Treatment, 2011, 22(2):102-105.
Deben et al., "APR-246 (PRIMA-1MET) strongly synergizes with AZD2281 (olaparib) induced PARP inhibition to induce apoptpsis in non-small cell lung cancer cell lines," Cancer Letters, 2016, 375(2):313-322.
DeKruyff et al., "T Cell/Transmembrane, Ig, and Mucin-3 Allelic Variants Differentially Recognize Phosphatidylserine and Mediate Phagocytosis of Apoptotic Cells," J Immunol., 2010, 184(4):1918-1930.
Dinarello et al., "IL-1 family nomenclature," Nat. Immunol., 2010, 11(11):973.
Eisenhauer, et al., "New response evaluation criteria in solid tumors: Revised Recist guideline (version 1.1.)," Eur. J. of Cancer, 45: 228-247 (2009).
EP Search Report in European Appln. No. 17867255.6, dated Jul. 6, 2020, 10 pages.
EP Search Report in European Appln. No. 20150611.0, dated May 8, 2020, 10 pages.
European Patent Office, extended European Search Report in European Patent Application No. 16774301.2 (dated Nov. 14, 2018).
Fourcade et al., "Upregulation of Tim-3 and PD-1 expression is associated with tumor antigen-specific CD8+ T cell dysfunction in melanoma patients," J. Exp. Med., 2010, 207(10):2175-2186.
Fuhrmann-Benzakein et al., "Inducible and irreversible control of gene expression using a single transgene," Nuc. Acid. Res., 2000, 28:e99.
Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol., 2009, 83(18):9122-9130.
Guo et al., "Combined TIM-3 blockade and CD137 activation affords the long-term protection in a murine model of ovarian cancer," Journal of Translational Medicine, 2013, 11:215.
Han et al., "Tim-3: an activation marker and activation limiter of innate immune cells," Frontiers in Immunology, 2013, 4:449.
Hastings et al., "TIM-3 is expressed on activated human CD4+ T cells and regulates Th1 and Th17 cytokines, " Eur J Immunol., 2009, 39: 2492-2501.
Holliger et al., "Engineered antibody fragments and the rise of single domains," Nature biotechnol., 2005, 23(9):1126-1136.
Horlick et al., "Combinatorial gene expression using multiple episomal vectors," Gene, 2000, 243(1-2):187-194.
Hou et al., "Humanization of an anti-CD34 monoclonal antibody by complementarity-determining region grafting based on computer-assisted molecular modelling," J. Biochem., 2008, 144(1):115-120.
Huang et al., "CEACAM1 regulates TIM-3-mediated tolerance and exhaustion, " Nature, 2015, 517(7534):386-90.
Hunter et al., "Preparation of iodine-131 labelled human growth hormone of high specific activity," Nature, 1962, 194:495-496.
Huston et al., "Protein engineering of antibody binding sites: recovery of specific activity in an anti-digoxin single-chain Fv analogue produced in *Escherichia coli*," Proc. Natl. Acad. Sci. USA, 1988, 85:5879-5883.
Ichii et al., "Local overexpression of interleukin-1 family, member 6 relates to the development of tubulointerstitial lesions," Laboratory Investigation, 2010, 90(3):459-475.
Ignatova, "Monitoring protein stability in vivo," Microb. Cell Fact., 2005, 4:23.
Indra et al., "Temporally-controlled site-specific mutagenesis in the basal layer of the epidermis: comparison of the recombinase activity of the tamoxifen-inducible Cre-ER(T) and Cre-ER(T2) recombinases," Nuc. Acid. Res., 1999, 27:4324-4327.
International Preliminary Report on Patentability in International Appln. No. PCT/US2017/059619, dated May 7, 2019, 7 pages.
International Search Report and Written Opinion in International Application No. PCT/US2016/025532 (dated Aug. 22, 2016).

International Search Report and Written Opinion in International Application No. PCT/US2017/059619 (dated Jun. 15, 2018).
International Search Report and Written Opinion in International Appln. No. PCT/US2016/025535, dated Aug. 22, 2016, 16 pages.
International Search Report and Written Opinion in International Appln. No. PCT/US2017/059619, dated Jun. 15, 2018, 10 pages.
Jack et al., "Looping out and deletion mechanism for the immunoglobulin heavy-chain class switch," Proc. Natl. Acad. Sci. USA, 1988, 85:1581-1585.
Jin et al., "Cooperation of Tim-3 and PD-1 in CD8 T-cell exhaustion during chronic viral infection," Proc Natl Acad Sci USA, 2010, 107(33):14733-14738.
Johnston, "Biolistic transformation: microbes to mice," Nature, 1990, 346:776-777.
Jones et al., "Tim-3 expression defines a novel population of dysfunctional T cells with highly elevated frequencies in progressive HIV-1 infection," J. Exp. Med., 2008, 205:2763-2779.
Ju et al., "T cell immunoglobulin- and mucin-domain-containing molecule-3 (Tim-3) mediates natural killer cell suppression in chronic hepatitis B," B. J. Hepatol., 2010, 52:322-329.
Kane, "TIM Proteins and Immunity," Journal of Immunology, 2010, 184(6):2743-2749.
Kashmiri et al., "SDR grafting—a new approach to antibody humanization," Methods, 2005, 36(1):25-34.
Kent et al., "Ouabain resistance conferred by expression of the cDNA for a murine Na+, K+-ATPase alpha subunit," Science, 1987, 237:901-903.
Kitts et al., "A method for producing recombinant baculovirus expression vectors at high frequency," Biotechniques, 1993, 14:810-17.
Kohler and Milstein, "Derivation of specific antibody-producing tissue culture and tumor lines by cell fusion, " Eur. J. Immunol., 1976, 5:511-519.
Kramer & Fussenegger, "Transgene control engineering in mammalian cells," Methods Mol. Biol., 2005, 308:123-144.
Le et al., "PD-1 Blockade in Tumors with Mismatch-Repair Deficiency," N. Engl. J. Med., 2015, 372(26):2509-2520.
Liberal et al., "The impaired immune regulation of autoimmune hepatitis is linked to a defective galectin-9/tim-3 pathway," Hepatology, 2012, 56(2):677-686.
Lonberg, "Human antibodies from transgenic animals," Nat. Biotechnol., 2005, 23(9):1117-25.
Lonberg, "Human monoclonal antibodies from transgenic mice," Handb. Exp. Pharmacol., 2008, 181:69-97.
Lowy et al., "Isolation of transforming DNA: cloning the hamster aprt gene," Cell, 1980, 22:817-823.
Lucklow et al., "Efficient generation of infectious recombinant baculoviruses by site-specific transposon-mediated insertion of foreign genes into a baculovirus genome propagated in *Escherichia coli*," J Viral., 1993, 67:4566-4579.
Lucklow, "Baculovirus systems for the expression of human gene products," Curr. Opin. Biotechnol., 1993, 4:564-572.
Marrakchi et al., "Interleukin-36-receptor antagonist deficiency and generalized pustular psoriasis," N. Engl. J. Med., 2011, 365(7): 620-628.
McMahan et al., "Tim-3 expression on PD-1+ HCV-specific human CTLs is associated with viral persistence, and its blockade restores hepatocyte-directed in vitro cytotoxicity," J. Clin. Invest., 2010, 120(12):4546-4557.
Monney et al., "Th1-specific cell surface protein Tim-3 regulates macrophage activation and severity of an autoimmune disease," Nature, 2002, 415: 536-541.
Mulligan & Berg, "Selection for animal cells that express the *Escherichia coli* gene coding for xanthine-guanine phosphoribosyltransferase," Proc. Natl. Acad Sci. USA, 1981, 78:2072-2076.
Myers and Miller, "Optimal alignments in linear space," Cabios, 1989, 4:11-17.
Naik et al., "Autoinflammatory pustular neutrophilic diseases," Dermatologic Clinics, 2013, 31(3):405-425.
Nakayama et al., "Tim-3 mediates phagocytosis of apoptotic cells and cross-presentation," Blood, 2009, 113:3821-3830.

(56) References Cited

OTHER PUBLICATIONS

Ndhlovu et al., "Tim-3 marks human natural killer cell maturation and suppresses cell-mediated cytotoxicity," Blood, 2012, 119:3734-3743.
Ngiow et al., "Anti-TIM3 antibody promotes T cell IFN-γ-mediated antitumor immunity and suppresses established tumors," Cancer Res., 2011, 71(10):3540-3551.
Ngiow et al., "Prospects for TIM3-Targeted Antitumor Immunotherapy," Cancer Res., 2011, 71(21):6567-6571.
Nishina et al., "Developing a common language for tumor response to immunotherapy: immune-related response criteria using unidimensional measurements," Clin. Cancer Res., 2013, 19(14):3936-43.
No et al., "Ecdysone-Inducible Gene Expression in Mammalian Cells and Transgenic Mice," Proc. Natl. Acad. Sci., 1996, 93:3346-3351.
Nygren, "Conjugation of horseradish peroxidase to Fab fragments with different homobifunctional and heterobifunctional cross-linking reagents. A comparative study," J Histochem. and Cytochem., 1982, 30:407-412.
O'Hare et al., "Transformation of mouse fibroblasts to methotrexate resistance by a recombinant plasmid expressing a prokaryotic dihydrofolate reductase," Proc. Natl. Acad Sci. USA, 1981, 78:1527-1531.
Osbourn et al., "Directed selection of MIP-1 alpha neutralizing CCR5 antibodies from a phage display human antibody library," Nat. Biotechnol., 1998, 16:778.
Pain et al., "Preparation of protein A-peroxidase monoconjugate using a heterobifunctional reagent, and its use in enzyme immunoassays," J Immunol. Meth., 1981, 40:219-230.
Rustin et al., "Definitions for response and progression in ovarian cancer clinical trials incorporating Recist 1.1 and CA 125 agreed by the Gynecological Cancer Intergroup (GCIG)," Int J Gynecol Cancer 2011, 21:419-423.
Sakuishi et al., "Emerging Tim-3 functions in antimicrobial and tumor immunity," Trends in Immunology, 2011, 32(8): 345-349.
Sakuishi et al., "Targeting Tim-3 and PD-1 pathways to reverse T cell exhaustion and restore anti-tumor immunity, " J. Exp. Med., 2010, 207(10):2187-2194.
Santerre et al., "Expression of prokaryotic genes for hygromycin B and G418 resistance as dominant-selection markers in mouse L cells," Gene, 1984, 30:147-156.
Seki et al., "Galectin-9 suppresses the generation of Th17, promotes the induction of regulatory T cells, and regulates experimental autoimmune arthritis ," Clin. Immunol., 2008, 127:78-88.
Silva et al., "The S228P mutation prevents in vivo and in vitro IgG4 Fab-arm exchange as demonstrated using a combination of novel quantitative immunoassays and physiological matrix preparation ," J. Biol. Chem. 2015, 290(9):5462-5469.
Soding, "Protein homology detection by HMM-HMM comparison," Bioinformatics, 2005, 21(7):951-960.
Sugiura et al., "The majority of generalized pustular psoriasis without psoriasis vulgaris is caused by deficiency of interleukin-36 receptor antagonist," J. Invest. Derm., 2013, 133(11):2514-2521.
Szybalska & Szybalski, "Genetics of human cell line. IV. DNA-mediated heritable transformation of a biochemical trait," Proc. Natl. Acad Sci. USA, 1962, 48:2026-2034.
Tortola et al., "Psoriasiform dermatitis is driven by IL-36-mediated DC-keratinocyte crosstalk, " J. Clin. Invest., 2012, 122(11): 3965-3976.
Towne et al., "IL-36 in psoriasis," Curr. Opin. Pharmacol., 2012, 12(4):486-490.
Towne et al., "Interleukin (IL)-1 F6, IL-1 F8, and IL-1 F9 Signal through IL-1 Rrp2 and IL-1 RAcP to Activate the Pathway Leading to NF-KB and MAPKs" J. Biol. Chem., 2004, 279(14):13677-13688.
Turnis et al., "Combinatorial Immunotherapy: PD-1 may not be LAG-ing behind anymore," Oncoimmunology, 1.7, 2012, 1172-1174.
Urlaub et al., "Isolation of Chinese hamster cell mutants deficient in dihydrofolate reductase activity," Proc. Natl. Acad. Sci. USA, 1980, 97:4216-4220.
Vigne et al., "IL-36 signaling amplifies Th1 responses by enhancing proliferation and Th1 polarization of naive CD4+ T cells," Blood, 2012, 120(17):3478-3487.
Vigne et al., "IL-36R ligands are potent regulators of dendritic and T cells," Blood, 2011, 118(22):5813-5823.
Westdorp et al., "Opportunities for immunotherapy in microsatellite instable colorectal cancer ," Cancer Immunol. Immunother., 2016, 65(10):1249-1259.
Wigler et al., "Transfer of purified herpes virus thymidine kinase gene to cultured mouse cells," Cell, 1977, 11:223-232.
Wigler et al., "Transformation of mammalian cells with an amplifiable dominant-acting gene," Proc. Natl. Acad Sci. USA, 1980, 77:3567-3570.
Woo et al., "Immune inhibitory molecules LAG-3 and PD-1 synergistically regulate T-cell function to promote tumoral immune escape," Cancer Res., 2012, 72:917-927.
Wu et al., "Blockade of Tim-3 signaling restores the virus-specific $CD8^+$T-cell response in patients with chronic hepatitis B," Eur. J Immunol., 2012, 42(5):1180-1191.
Zhou et al., "Coexpression of Tim-3 and PD-1 identifies a CD8+ T-cell exhaustion phenotype in mice with disseminated acute myelogenous leukemia," Blood, 2011, 117(17):4501-4510.
Zhu et al., "The Tim-3 ligand galectin-9 negatively regulates T helper type 1 immunity ," Nat. Immunol., 2005, 6:1245-1252.
Anonymous: "View of NCT02608268 on Oct. 13, 2016", ClinicalTrials.gov Archive, Oct. 13, 2016 (Oct. 13, 2016), pp. 1-9, XP055458570, Retrieved from Internet: URL:https://clinicaltrials.gov/archive/NCT02608268/2016_10_13 [retrieved on Mar. 12, 2018] the whole document.
Anonymous: "View of NCT02817633 on Jan. 14, 2016", ClinicalTrials.gov Archive, Nov. 14, 2016 (Nov. 14, 2016), pp. 1-7, XP055458594, Retrieved from Internet: URL:https://clinicaltrials.gov/archive/NCT02817633/2016_11_14 [retrieved on Mar. 12, 2018] the whole document.
Glen J. Weiss et al: "A Phase 1 Study of TSR-022, an Anti-TIM-3 Monoclonal Antibody, in Patents (pts) With Advanced Solid Tumors", Journal for Immunotherapy of Cancer, vol. 5, No. Supplement 2, Nov. 7, 2017 (Nov. 7, 2017), p. 7, XP055458584, 013.
Murtaza A et al: "Discovery of TRS-022, a Novel, Potent Anti-Human TIM-3 Therapeutic Antibody", Eurpoean Journal of Cancer, vol. 69, 311, Nov. 29, 2016 (Nov. 29, 2016), p. S102, XP029843768, ISSN: 0959-8049, DOI: 10.1016/S0959-8049 (16) 32903-3 the whole document.
International Search Report for PCT/US2018/013021, 6 pages (dated Mar. 23, 2018).
ClinicalTrials.gov [online], "NCT02723955: Dose Escalation and Expansion Study of GSK3359609 in Participants With Selected Advanced Solid Tumors (Induce-1)," GlaxoSmithKline, Mar. 31, 2016, retrieved on Oct. 7, 2021, retrieved from URL <https://clinicaltrials.gov/ct2/show/NCT02723955>, 16 pages.
ClinicalTrials.gov [online], "NCT02817633: A Study of TSR-022 in Participants With Advanced Solid Tumors (Amber)," Tesaro, Inc., Jun. 29, 2016, retrieved on Oct. 7, 2021, retrieved from URL <https://clinicaltrials.gov/ct2/show/NCT02817633>, 15 pages.
ClinicalTrials.gov [online], "NCT03680508: TSR-022 (Anti-TIM-3 Antibody) and TSR-042 (Anti-PD-1 Antibody) in Patients With Liver Cancer," University of Hawaii, Sep. 21, 2018, retrieved on Oct. 7, 2021, retrieved from URL <https://clinicaltrials.gov/ct2/show/NCT03680508>, 9 pages.
ClinicalTrials.gov [online], "NCT03739710: Platform Trial of Novel Regimens Versus Standard of Care (SoC) in Non-small Cell Lung Cancer (NSCLC)," GlaxoSmithKline, Nov. 14, 2018, retrieved on Oct. 7, 2021, retrieved from URL <https://clinicaltrials.gov/ct2/show/NCT03739710>, 14 pages.
ClinicalTrials.gov [online], "NCT04139902: Neoadjuvant PD-1 Inhibitor Dostarlimab (TSR-042) vs. Combination of Tim-3 Inhibitor Cobolimab (TSR-022) and PD-1 Inhibitor Dostarlimab (TSR-042) in Melanoma," Diwakar Davar, Oct. 25, 2019, retrieved on Oct. 7, 2021, retrieved from URL <https://clinicaltrials.gov/ct2/show/NCT04139902>, 10 pages.

(56) References Cited

OTHER PUBLICATIONS

ClinicalTrials.gov [online], "NCT04655976: Study of Cobolimab in Combination With Dostarlimab and Docetaxel in Advanced NSCLC Participants (Costar Lung), " GlaxoSmithKline, Dec. 7, 2020, retrieved on Oct. 7, 2021, retrieved from URL <https://clinicaltrials.gov/ct2/show/NCT04655976>, 10 pages.

Davar et al., "A Phase 1 Study of TSR-022 (Anti-TIM-3) in Combination with TSR-042 (Anti-PD-1)," Oral Presentation, Society for Immunotherapy of Cancer 33rd Annual Meeting, Nov. 7-11, 2018, 21 pages.

Davar et al., "A Phase 1 Study of TSR-022, an Anti-TIM-3 Monoclonal Antibody, in Combination with TSR-042 (Anti-PD-1) in Patients with Colorectal Cancer and Post-PD-1 NSCLC and Melanoma," Full Poster, Society for Immunotherapy of Cancer 33rd Annual Meeting, Nov. 7-11, 2018, 1 page.

Davar et al., "A phase 1 study of TSR-022, an anti-TIM-3 monoclonal antibody, in combination with TSR-042 (anti-PD-1) in patients with colorectal cancer and post-PD-1 NSCLC and melanoma," Submission Summary, Aug. 1, 2018, retrieved from URL <https://sitc.planion.com/Web.User/ProofForm?FT=ABSSUBMIT&ACCOUNT=SITC&FORMID=10361&SCHEDID=10877&CONF=RABS18&CKEY=15HH13HSS>, 3 pages.

Kehry et al., "Targeting PD-1, TIM-3 and LAG-3 in Combination for Improved Immunotherapy Combinations," Poster, AACR Annual Meeting, 2015, 1 page.

Murtaza et al., "Discovery of TSR-022, a novel, potent anti-human TIM-3 therapeutic antibody," Poster Sessions: Immunotherapy, Nov. 29, 2016, Poster P137, 1 page.

Sharma et al., "Evaluation of TSR-042, TSR-022 and TSR-033 as single agents and in combination in humanized mice," Poster, Regeneron's Workshop on Humanized Immune System (HIS) Mice, Nov. 28-30, 2018, 1 page.

Weiss et al., "A phase 1 study of TSR-022, an anti-TIM-3 monoclonal antibody, in patients (pts) with advanced solid tumors," Regular Abstract, SITC 32nd Annual meeting & Pre-Conference Programs, Aug. 1, 2017, 9 pages.

Weiss et al., "A Phase 1 Study of TSR-022, an Anti-TIM-3 Monoclonal Antibody, in Patients with Advanced Solid Tumors," Oral Presentation, Society for Immunotherapy of Cancer, Nov. 8-12, 2017, 12 pages.

Zahra et al., "Randomized Phase II Neoadjuvant Study of PD-1 Inhibitor Dostarlimab (TSR-042) vs. Combination of Tim-3 Inhibitor TSR-022 and PD-1 Inhibitor Dostarlimab (TSR-042) in Resectable Stage III or Oligometastatic Stage IV Melanoma (Neo-MEL-T)," Society for Immunotherapy of Cancer—34th Annual Meeting, Nov. 6-10, 2019, P457, 1 page.

GenBank Accession No. AEX28953.1, "immunoglobulin G heavy chain variable region, partial [*Homo sapiens*]," Jan. 10, 2014, 2 pages.

Kunik et al., "Structural Consensus among Antibodies Defines the Antigen Binding Site," PLoS Computational Biology, Feb. 2012, 8(2):e1002388, 12 pages.

Schiller, "Current Standards of Care in Small-Cell and Non-Small-Cell Lung Cancer", Oncology, Sep. 2001, 61:3-13.

Jemperli, Highlights of Prescribing Information, United States Prescribing Information, Apr. 2021.

Jemperli, Statement on a Nonproprietary Name Adopted by the USAN Council, United States Adopted Name, Nov. 29, 2017, 2 pages.

Anderson, "Tim-3, a negative regulator of anti-tumor immunity," Current Opinion in Immunology, Apr. 2012, 24(2):213-216.

Chunmei et al., "Biological activity and application of TIM-3 antibody," Military Medical Sciences, 2014, 8:617-625 (Abstract Only).

clinicaltrials.gov [online], "Phase I-Ib/II Study of MBG453 as Single Agent and in Combination With PDR001 in Patients With Advanced Malignancies," Nov. 18, 2015, retrieved on Jan. 17, 2023, retrieved from URL<https://clinicaltrials.gov/ct2/show/NCT02608268?term=nct02608268&draw=2&rank=1>, 10 pages.

Malmqvist, "Biospecific interaction analysis using biosensor technology," Nature, Jan. 14, 1993, 361:186-187.

Chen et al., "Generation and analysis of random point mutations in an antibody CDR2 sequence: many mutated antibodies lose their ability to bind antigen," Sep. 1992, J. Exp. Med. 176:855-66.

Dostarlimab, Statement on a Nonproprietary Name Adopted by the USAN Council, retrieved on Oct. 17, 2022, retrieved from URL<https://searchusan.ama~assn.org/usan/documentDownload?uri=%2Funstructured%2Fbinary%2Fusan%2Fdostarlimab.pdf>, 2 pages.

Kegg Drug: Nivolumab, retrieved on Oct. 17, 2022, retrieved from URL<https://www.genome.jp/dbget-bin/www_bget?drug:D10316>, 2 pages.

Klein et al., "Somatic Mutations of the Immunoglobulin Framework are Generally Required for Broad and Potent HIV-1 Neutralization," Mar. 2013, Cell, vol. 153, Issue 1, pp. 126-138.

Nivolumab, Statement on a Nonproprietary Name Adopted by the USAN Council, retrieved on Oct. 17, 2022, retrieved from URL<https://searchusan.ama-assn.org/usan/documentDownload?uri=/unstructured/binary/usan/nivolumab.pdf>, 1 page.

Pembrolizumab, Statement on a Nonproprietary Name Adopted by the USAN Council, Nov. 27, 2013, retrieved on Oct. 17, 2022, retrieved from URL<https://searchusan.ama-assn.org/usan/documentDownload?uri=%2Funstructured%2Fbinary%2Fusan%2Fpembrolizumab.pdf>, 2 pages.

Tislelizumab, Statement on a Nonproprietary Name Adopted by the USAN Council, retrieved on Oct. 17, 2022, retrieved from URL<https://searchusan.ama-assn.org/usan/documentDownload?uri=%2Funstructured%2Fbinary%2Fusan%2Ftislelizumab.pdf>, 2 pages.

ABCD_AA805 in the ABCD (AntiBodies Chemically Defined) Database, retrieved on Oct. 18, 2022, retrieved from URL<https://web.expasy.org/abcd/ABCD_AA805>, 1 page.

Cemiplimab, Statement on a Nonproprietary Name Adopted by the USAN Council, retrieved on Oct. 18, 2022, retrieved from URL<https://searchusan.ama-assn.org/usan/documentDownload?uri=%2Funstructured%2Fbinary%2Fusan%2Fcemiplimab.pdf>, 2 pages.

Finlay et al., "Anti-PD1 'SHR-1210' aberrantly targets pro-angiogenic receptors and this polyspecificity can be ablated by paratope refinement," 2019, MABS, vol. 11, No. 1, 26-44.

Mathijssen et al., "Flat-Fixed Dosing Versus Body Surface Area-Based Dosing of Anticancer Drugs in Adults: Does It Make a Difference?" The Oncologist, Aug. 2007, 12(8): 913-923.

\* cited by examiner

| Characteristic | All patients enrolled (N=38) |
|---|---|
| Age, y | |
| Mean (SD) | 60.1 (13.5) |
| Median (min, max) | 61.0 (25, 85) |
| Sex, n (%) | |
| Male | 21 (55.3) |
| Female | 17 (44.7) |
| ECOG performance status score, n (%) | |
| 0 | 10 (26.3) |
| 1 | 28 (73.7) |
| Number of prior treatment lines, n (%) | |
| Mean (SD) | 3.2 (2.3) |
| Median (min, max) | 2.0 (1, 10) |

| Tumor site, N=38 | |
|---|---|
| • Colon (n=5) | • Pleura (n=1) |
| • Skin (n=4) | • Lung (n=2) |
| • Ovary (n=1) | • Rectum (n=3) |
| • Breast (n=2) | • Thyroid (n=2) |
| • Brain (n=2) | • Liver (n=2) |
| • Head and neck (n=2) | • Esophagus (n=1) |
| • Testis (n=1) | • Other (n=10) |

ECOG=eastern Cooperative Oncology Group; SD=standard deviation
As of October 2017, database cutoff.

FIG. 5

METHODS OF TREATING CANCER WITH ANTI-TIM-3 ANTIBODIES

CROSS-REFERENCE TO RELATED APPLICATIONS

The present application is a 35 U.S.C. § 371 National Stage Application of International Application No. PCT/US2018/013021, filed Jan. 9, 2018, and claims the benefit of U.S. Provisional Patent Application No. 62/444,354, filed Jan. 9, 2017, and U.S. Provisional Application No. 62/582,272, filed Nov. 6, 2017, each of which is incorporated by reference in its entirety.

SEQUENCE LISTING

The present specification makes reference to a Sequence Listing provided in electronic form as an ASCII.txt file named "TSR-002 SEQ LIST_ST25" that was generated on Jan. 8, 2018, and is 39,647 bytes in size.

BACKGROUND

Cancer is a serious public health problem, with about 600,920 people in the United States of America expected to die of cancer in 2017 alone according to the American Cancer Society, Cancer Facts & Figures 2017 (https://www.cancer.org/research/cancer-facts-statistics/all-cancer-facts-figures/cancer-facts-figures-2017.html). Accordingly, there continues to be a need for effective therapies to treat cancer patients.

SUMMARY

The present invention encompasses a recognition that certain dosage regimens for agents that are capable of inhibiting T Cell Immunoglobulin and Mucin Domain-3 (TIM-3) signaling (e.g., anti-TIM-3 antibody agents) are useful for treating disorders such as cancer.

In some embodiments, the present disclosure provides methods of treating disorders such as cancer that include administering compositions that deliver particular TIM-3 inhibitors (e.g., anti-TIM-3 antibody agents) according to dosing regimens that may achieve clinical benefit in at least some patients.

In embodiments, a TIM-3 inhibitor is a TIM-3 binding agent. In embodiments, a TIM-3 binding agent is an antibody, an antibody conjugate, or an antigen-binding fragment thereof. In embodiments, a TIM-3 binding agent is an antibody agent (i.e., an anti-TIM-3 antibody agent).

In embodiments, an anti-TIM-3 antibody agent comprises a heavy chain variable region with one or more CDR sequences selected from SEQ ID NOs: 21, 22, and 23 and/or a light chain variable region with one or more CDR sequences selected from SEQ ID NOs: 24, 25, and 26. In embodiments, an anti-TIM-3 antibody agent comprises a heavy chain variable region with two or three CDR sequences selected from SEQ ID NOs: 21, 22, and 23 and/or a light chain variable region with two or three CDR sequences selected from SEQ ID NOs: 24, 25, and 26. In embodiments, an anti-TIM-3 antibody agent comprises a heavy chain variable region with three CDR sequences of SEQ ID NOs: 21, 22, and 23 and/or a light chain variable region with three CDR sequences of SEQ ID NOs: 24, 25, and 26. In embodiments, an anti-TIM-3 antibody agent comprises a heavy chain variable region with three CDR sequences of SEQ ID NOs: 21, 22, and 23 and a light chain variable region with three CDR sequences of SEQ ID NOs: 24, 25, and 26.

In embodiments, an anti-TIM-3 antibody agent comprises an immunoglobulin heavy chain variable domain whose amino acid sequence having at least about 80%, 85%, 90%, 91%, 92%, 93%, 94%, 95%, 96%, 97%, 98%, or 99% sequence identity to SEQ ID NO:1 or SEQ ID NO:7. In embodiments, an anti-TIM-3 antibody agent comprises an immunoglobulin light chain variable domain whose amino acid sequence having at least about 80%, 85%, 90%, 91%, 92%, 93%, 94%, 95%, 96%, 97%, 98%, or 99% sequence identity to SEQ ID NO:2 or SEQ ID NO:8. In some embodiments, an anti-TIM-3 antibody agent comprises an immunoglobulin heavy chain variable domain whose amino acid sequence comprises SEQ ID NO: 1 or SEQ ID NO: 7 and/or an immunoglobulin light chain variable domain whose amino acid sequence comprises SEQ ID NO: 2 or SEQ ID NO: 8. In some embodiments, an anti-TIM-3 antibody agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8.

In some embodiments, an anti-TIM-3 antibody agent comprises an immunoglobulin heavy chain polypeptide comprising an amino acid sequence having about 80%, 85%, 90%, 91%, 92%, 93%, 94%, 95%, 96%, 97%, 98%, or 99% sequence identity to SEQ ID NO:3. In some embodiments, an anti-TIM-3 antibody agent comprises an immunoglobulin light chain polypeptide comprising an amino acid sequence having about 80%, 85%, 90%, 91%, 92%, 93%, 94%, 95%, 96%, 97%, 98%, or 99% sequence identity to SEQ ID NO:4. In some embodiments, an anti-TIM-3 antibody agent comprises an immunoglobulin heavy chain whose amino acid sequence comprises SEQ ID NO: 3 and/or an immunoglobulin light chain whose amino acid sequence comprises SEQ ID NO: 4. In some embodiments, an anti-TIM-3 antibody agent comprises an immunoglobulin heavy chain whose amino acid sequence comprises SEQ ID NO: 3 and an immunoglobulin light chain whose amino acid sequence comprises SEQ ID NO: 4.

The present disclosure provides, in some embodiments, methods of treating a disorder in a subject that is responsive to T Cell Immunoglobulin and Mucin Protein 3 (TIM-3) inhibition comprising administering a therapeutically effective dose of an agent that is capable of inhibiting TIM-3 signaling. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of increasing T cell activation or T cell effector function in a subject that is responsive to T Cell Immunoglobulin and Mucin Protein 3 (TIM-3) inhibition comprising administering a therapeutically effective dose of an agent that is capable of inhibiting TIM-3 signaling. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of reducing tumors or inhibiting the growth of tumor cells in a subject that is responsive to T Cell Immunoglobulin and Mucin Protein 3 (TIM-3) inhibition comprising administering a therapeutically effective dose of an agent that is capable of inhibiting TIM-3 signaling. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of inducing an immune response in a subject that is responsive to T Cell Immunoglobulin and Mucin Protein 3 (TIM-3) inhibition comprising administering a therapeutically effective dose of an agent that is capable of inhibiting TIM-3 signaling. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of enhancing an immune response or increasing the activity of an immune cell in a subject that is responsive to T Cell Immunoglobulin and Mucin Protein 3 (TIM-3) inhibition comprising administering a therapeutically effective dose of an agent that is capable of inhibiting TIM-3 signaling. In embodiments, an immune response is a humoral or cell mediated immune response. In embodiments, an immune response is a CD4 or CD8 T cell response. In embodiments, an immune response is a B cell response. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of treating cancer that comprises administering to a patient in need of treatment an anti-T Cell Immunoglobulin and Mucin Domain-3 (TIM-3) at a therapeutically effective dose. In embodiments, a therapeutically effective dose is about 1, 3 or 10 mg/kg of a TIM-3 inhibitor. In embodiments, a therapeutically effective dose is about 100-1500 mg of a TIM-3 inhibitor. In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of a TIM-3 inhibitor. In embodiments, a therapeutically effective dose is about 1 mg/kg. In embodiments, a therapeutically effective dose is about 3 mg/kg. In embodiments, a therapeutically effective dose is about 10 mg/kg. In embodiments, a therapeutically effective dose is a flat dose about 100 mg of a TIM-3 inhibitor. In embodiments, a therapeutically effective dose is a flat dose about 300 mg of a TIM-3 inhibitor. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of a TIM-3 inhibitor. In embodiments, a TIM-3 inhibitor is any anti-TIM-3 antibody agent described herein.

The present disclosure provides, in some embodiments, methods of treating cancer comprising administering to a patient in need of treatment an anti-T Cell Immunoglobulin and Mucin Domain-3 (TIM-3) antibody at a therapeutically effective dose at an administration interval for a period sufficient to achieve clinical benefit. In embodiments, an anti-TIM-3 antibody comprises a heavy chain comprising three CDRs that have sequences of SEQ ID NOs: 21, 22, or 23; and/or a light chain comprising three CDRs that have sequences of SED ID NOs: 24, 25, or 26. In embodiments, an anti-TIM-3 antibody comprises an immunoglobulin heavy chain variable domain comprising SEQ ID NO: 1 or SEQ ID NO: 7 and an immunoglobulin light chain variable domain comprising SEQ ID NO:2 or SEQ ID NO: 8. In embodiments, an anti-TIM-3 antibody comprises a heavy chain polypeptide comprising SEQ ID NO: 3 and a light chain polypeptide comprising SEQ ID NO: 4. In embodiments, a therapeutically effective dose is about 1, 3 or 10 mg/kg of an anti-TIM-3 antibody. In embodiments, a therapeutically effective dose is about 100-1500 mg of an anti-TIM-3 antibody In embodiments, a therapeutically effective dose is a flat dose about 100 mg; a flat dose about 200 mg; a flat dose about 300 mg; a flat dose about 400 mg; a flat dose about 500 mg; a flat dose about 600 mg; a flat dose about 700 mg; a flat dose about 800 mg; a flat dose about 900 mg; a flat dose about 1000 mg; a flat dose about 1100 mg; a flat dose about 1200 mg; a flat dose about 1300 mg; a flat dose about 1400 mg; or a flat dose about 1500 mg of an anti-TIM-3 antibody. In embodiments, a therapeutically effective dose is about 1 mg/kg of an anti-TIM-3 antibody. In embodiments, a therapeutically effective dose is about 3 mg/kg of an anti-TIM-3 antibody. In embodiments, a therapeutically effective dose is about 10 mg/kg of an anti-TIM-3 antibody. In embodiments, a therapeutically effective dose is a flat dose about 100 mg of an anti-TIM-3 antibody. In embodiments, a therapeutically effective dose is a flat dose about 300 mg of an anti-TIM-3 antibody. In embodiments, a therapeutically effective dose is a flat dose about 500 mg of a TIM-3 inhibitor. In embodiments, a therapeutically effective dose is a flat dose about 900 mg of a TIM-3 inhibitor. In embodiments, a therapeutically effective dose is a flat dose about 1200 mg of an anti-TIM-3 antibody.

In any of the methods described herein, a therapeutically effective dose is about 1 mg/kg of a TIM-3 inhibitor. In any of the methods described herein, a therapeutically effective dose is about 3 mg/kg of a TIM-3 inhibitor. In any of the methods described herein, a therapeutically effective dose is about 5 mg/kg of a TIM-3 inhibitor. In embodiments, a TIM-3 inhibitor is any anti-TIM-3 antibody agent described herein.

In any of the methods described herein, a therapeutically effective dose is about 100 mg of a TIM-3 inhibitor. In any of the methods described herein, a therapeutically effective dose is about 200 mg of a TIM-3 inhibitor. In any of the methods described herein, a therapeutically effective dose is about 300 mg of a TIM-3 inhibitor. In any of the methods described herein, a therapeutically effective dose is about 400 mg of a TIM-3 inhibitor. In any of the methods described herein, a therapeutically effective dose is about 500 mg of a TIM-3 inhibitor. In any of the methods described herein, a therapeutically effective dose is about 600 mg of a TIM-3 inhibitor. In any of the methods described herein, a therapeutically effective dose is about 700 mg of a TIM-3 inhibitor. In any of the methods described herein, a therapeutically effective dose is about 800 mg of a TIM-3 inhibitor. In any of the methods described herein, a therapeutically effective dose is about 900 mg of a TIM-3 inhibitor. In any of the methods described herein, a therapeutically effective dose is about 1000 mg of a TIM-3 inhibitor. In any of the methods described herein, a therapeutically effective dose is about 1100 mg of a TIM-3 inhibitor. In any of the methods described herein, a therapeutically effective dose is about 1200 mg of a TIM-3 inhibitor. In any of the methods described herein, a therapeutically effective dose is about 1300 mg of a TIM-3 inhibitor. In any of the methods described herein, a therapeutically effective dose is about 1400 mg of a TIM-3 inhibitor. In any of the methods described herein, a therapeutically effective dose is about 1500 mg of a TIM-3 inhibitor. In embodiments, a TIM-3 inhibitor is any anti-TIM-3 antibody agent described herein.

In embodiments, a TIM-3 inhibitor is administered at an administration interval (or treatment cycle) of once a week (Q1W), once every 2 weeks (Q2W), once every 3 weeks (Q3W), once every 4 weeks (Q4W), once every 5 weeks (Q5W), or once every 6 weeks (Q6W). In embodiments, a TIM-3 inhibitor is administered for a period of at least about 2, 3, 4, 5, 6, 7, 8, 9, 10, 11, 12, 13, 14, 15, 16, 17, 18, 19, 20 weeks, or more. In embodiments, a TIM-3 inhibitor is administered at an administration interval (or treatment cycle) of once a week (Q1W). In embodiments, a TIM-3 inhibitor is administered at an administration interval (or treatment cycle) of once every 2 weeks (Q2W). In embodiments, a TIM-3 inhibitor is administered at an administration interval (or treatment cycle) of once every three weeks (Q3W). In embodiments, a TIM-3 inhibitor is administered at an administration interval (or treatment cycle) of once every 4 weeks (Q4W). In embodiments, a TIM-3 inhibitor is administered at an administration interval (or treatment cycle) of once every 5 weeks (Q5W). In embodiments, a TIM-3 inhibitor is administered at an administration interval (or treatment cycle) of once every 6 weeks (Q6W).

In embodiments, a TIM-3 inhibitor (e.g., a therapeutically effective dose of about 100 mg, 300 mg, 500 mg, or 900 mg) is administered at an administration interval (or treatment cycle) of once every 3 weeks. In embodiments, a therapeutically effective dose of about 100 mg is administered at an administration interval (or treatment cycle) of once every 3 weeks. In embodiments, a therapeutically effective dose of about 300 mg is administered at an administration interval (or treatment cycle) of once every 3 weeks. In embodiments, a therapeutically effective dose of about 500 mg is administered at an administration interval (or treatment cycle) of once every 3 weeks. In embodiments, a therapeutically effective dose of about 900 mg is administered at an administration interval (or treatment cycle) of once every 3 weeks.

In embodiments, a TIM-3 inhibitor is administered on the first day of a treatment cycle or within 1, 2, or 3 days of the first day of a treatment cycle. In embodiments, a TIM-3 inhibitor is any anti-TIM-3 antibody agent described herein.

In embodiments, a TIM-3 inhibitor described herein is administered according to dosing regimens demonstrated to achieve a clinical benefit in some patients (for example, according to a regimen as determined by a physician, including dosing modifications). In embodiments, a TIM-3 inhibitor described herein is administered until treatment is discontinued due to, e.g., disease progression or an adverse reaction or as determined by a physician. In embodiments, a clinical benefit is stable disease ("SD"), a partial response ("PR") and/or a complete response ("CR"). In embodiments, a clinical benefit is stable disease ("SD"). In embodiments, a clinical benefit is a partial response ("PR"). In embodiments, a clinical benefit is a complete response ("CR"). In embodiments, PR or CR is determined in accordance with Response Evaluation Criteria in Solid Tumors (RECIST). In embodiments, a TIM-3 inhibitor is administered for a longer period to maintain clinical benefit. In embodiments, a TIM-3 inhibitor is any anti-TIM-3 antibody agent described herein.

In embodiments, a TIM-3 inhibitor is administered periodically to a subject at a dose of about 100 mg, about 300 mg, or about 1200 mg. In embodiments, a TIM-3 inhibitor is administered periodically to a subject at a dose of about 100 mg (e.g., once every three weeks (Q3W) and/or for 2, 3, 4, 5, 6, or more cycles). In embodiments, a TIM-3 inhibitor is administered periodically to a subject at a dose of about 300 mg (e.g., once every three weeks (Q3W) and/or for 2, 3, 4, 5, 6, or more cycles). In embodiments, a TIM-3 inhibitor is administered periodically to a subject at a dose of about 1200 mg (e.g., once every three weeks (Q3W) and/or for 2, 3, 4, 5, 6, or more cycles). In embodiments, a TIM-3 inhibitor is any anti-TIM-3 antibody agent described herein.

In embodiments, a subject has been further administered or will be administered a further therapeutic agent, such that the subject receives a TIM-3 inhibitor (e.g., any anti-TIM-3 antibody agent described herein) and a further therapeutic agent (e.g., one, two, three, four, or more further therapeutic agents).

In embodiments, a subject has been further administered or will be administered an immune checkpoint inhibitor, such that the subject receives a TIM-3 inhibitor (e.g., any anti-TIM-3 antibody agent described herein) and an immune checkpoint inhibitor. That is, a subject can be administered a TIM-3 inhibitor in combination with at least one immune checkpoint inhibitor.

In embodiments, a checkpoint inhibitor is an agent capable of inhibiting any of the following: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, IDO, or CSF-1R. In embodiments, a checkpoint inhibitor is a small molecule, a nucleic acid, a polypeptide (e.g., an antibody), a carbohydrate, a lipid, a metal, or a toxin. In embodiments, a checkpoint inhibitor is an antibody, an antibody conjugate, or an antigen-binding fragment thereof.

In embodiments, an immune checkpoint inhibitor is an agent that inhibits programmed death-1 protein (PD-1) signaling, cytotoxic T-lymphocyte-associated protein 4 (CTLA-4), lymphocyte activation gene-3 (LAG-3), T cell immunoglobulin and ITIM domain (TIGIT), indoleamine 2,3-dioxygenase (IDO), or colony stimulating factor 1 receptor (CSF1R).

In embodiments, an immune checkpoint inhibitor is a PD-1 inhibitor. In embodiments, a PD-1 inhibitor is a PD-1 binding agent (e.g., an antibody, an antibody conjugate, or an antigen-binding fragment thereof). In embodiments, a PD-1 binding agent is nivolumab, pembrolizumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, AMP-514/MEDI-0680, AGEN-2034, CS1001, TSR-042, Sym-021, PF-06801591, LZM009, KN-035, AB122, genolimzumab (CBT-501), AK 104, or GLS-010, or derivatives thereof. In embodiments, a PD-1 inhibitor is a PD-L1 or PD-L2 binding agent (e.g., an antibody, an antibody conjugate, or an antigen-binding fragment thereof). In embodiments, a PD-1 inhibitor is a PD-L1 or PD-L2 binding agent is durvalumab, atezolizumab, avelumab, BGB-A333, SHR-1316, FAZ-053, CK-301, or, PD-L1 millamolecule, or derivatives thereof. In embodiments, PD-1 inhibitor (e.g., TSR-042) is administered to the subject periodically at a dose of about 500 mg or 1000 mg. In embodiments, a PD-1 inhibitor (e.g., TSR-042) is administered to the subject periodically at a dose of about 500 mg or 1000 mg. In embodiments, a PD-1 inhibitor (e.g., TSR-042) is administered to the subject periodically at a dose of about 500 mg. In embodiments, a PD-1 inhibitor (e.g., TSR-042) is administered to the subject once every 3 weeks. In embodiments, a PD-1 inhibitor (e.g., TSR-042) is administered for 2, 3, 4, 5, 6, or more cycles. In embodiments, a PD-1 inhibitor (e.g., TSR-042) is administered for 4 cycles. In embodiments, a PD-1 inhibitor (e.g., TSR-042) is administered to the subject periodically at a dose of about 1000 mg. In embodiments, a PD-1 inhibitor (e.g., TSR-042) is administered to the subject once every 6 weeks. In embodiments, a PD-1 inhibitor (e.g., TSR-042) is administered at a first dose of about 500 mg once every 3 weeks for 4 cycles followed by a second dose of about 1000 mg once every 6 weeks (e.g., until treatment is discontinued).

In embodiments, an immune checkpoint inhibitor is a CTLA-4 inhibitor (e.g., an antibody, an antibody conjugate, or an antigen-binding fragment thereof). In embodiments, a CTLA-4 inhibitor is a small molecule, a nucleic acid, a polypeptide (e.g., an antibody), a carbohydrate, a lipid, a metal, or a toxin. In embodiments, a CTLA-4 inhibitor is a small molecule. In embodiments, a CTLA-4 inhibitor is a CTLA-4 binding agent. In embodiments, a CTLA-4 inhibitor is an antibody, an antibody conjugate, or an antigen-binding fragment thereof. In embodiments, a CTLA-4 inhibitor is ipilimumab (Yervoy), AGEN1884, or tremelimumab.

In embodiments, an immune checkpoint inhibitor is a LAG-3 inhibitor (e.g., an antibody, an antibody conjugate, or an antigen-binding fragment thereof). In embodiments, a LAG-3 inhibitor is a small molecule, a nucleic acid, a polypeptide (e.g., an antibody), a carbohydrate, a lipid, a metal, or a toxin. In embodiments, a LAG-3 inhibitor is a small molecule. In embodiments, a LAG-3 inhibitor is a LAG-3 binding agent. In embodiments, a LAG-3 inhibitor is an antibody, an antibody conjugate, or an antigen-binding fragment thereof. In embodiments, a LAG-3 inhibitor is a IMP321, BMS-986016, GSK2831781, Novartis LAG525, or a LAG-3 inhibitor described in WO 2016/126858, WO 2017/019894, or WO 2015/138920, each of which is hereby incorporated by reference in its entirety.

In embodiments, an immune checkpoint inhibitor is a TIGIT inhibitor (e.g., an antibody, an antibody conjugate, or an antigen-binding fragment thereof). In embodiments, a TIGIT inhibitor is a small molecule, a nucleic acid, a polypeptide (e.g., an antibody), a carbohydrate, a lipid, a metal, or a toxin. In embodiments, a TIGIT inhibitor is small molecule. In embodiments, a TIGIT inhibitor is a TIGIT binding agent. In embodiments, a TIGIT inhibitor is an antibody, an antibody conjugate, or an antigen-binding fragment thereof. In embodiments, a TIGIT inhibitor is MTIG7192A, BMS-986207, or OMP-31M32.

In embodiments, an immune checkpoint inhibitor is an IDO inhibitor. In embodiments, an IDO inhibitor is a small molecule, a nucleic acid, a polypeptide (e.g., an antibody), a carbohydrate, a lipid, a metal, or a toxin. In embodiments, an IDO inhibitor is small molecule. In embodiments, an IDO inhibitor is an IDO binding agent. In embodiments, an IDO inhibitor is an antibody, an antibody conjugate, or an antigen-binding fragment thereof.

In embodiments, an immune checkpoint inhibitor is a CSF1R inhibitor. In embodiments, a CSF1R inhibitor is a small molecule, a nucleic acid, a polypeptide (e.g., an antibody), a carbohydrate, a lipid, a metal, or a toxin. In embodiments, a CSF1R inhibitor is small molecule. In embodiments, a CSF1R inhibitor is a CSF1R binding agent. In embodiments, a CSF1R inhibitor is an antibody, an antibody conjugate, or an antigen-binding fragment thereof.

In embodiments, a method comprises administering a TIM-3 inhibitor (e.g., any anti-TIM-3 antibody agent described herein) with at least two of the immune checkpoint inhibitors. In embodiments, a method comprises administering a third checkpoint inhibitor. In embodiments, a method comprises administering a TIM-3 inhibitor with a PD-1 inhibitor, and a LAG-3 inhibitor, such that the subject receives all three. In embodiments, a method comprises administering a TIM-3 inhibitor with a PD-1 inhibitor, a LAG-3 inhibitor, and a CTLA-4 inhibitor, such that the subject receives all four.

In embodiments, a subject has been further administered or will be administered an agent that inhibits poly (ADP-ribose) polymerase (PARP), such that the subject receives treatment with a TIM-3 inhibitor and a PARP inhibitor.

In embodiments, a PARP inhibitor is a small molecule, a nucleic acid, a polypeptide (e.g., an antibody), a carbohydrate, a lipid, a metal, or a toxin. In embodiments, a PARP inhibitor is selected from the group consisting of: ABT-767, AZD 2461, BGB-290, BGP 15, CEP 8983, CEP 9722, DR 2313, E7016, E7449, fluzoparib, IMP 4297, INO1001, JPI 289, JPI 547, monoclonal antibody B3-LysPE40 conjugate, MP 124, niraparib, NU 1025, NU 1064, NU 1076, NU1085, olaparib, ONO2231, PD 128763, R 503, R554, rucaparib, SBP 101, SC 101914, simmiparib, talazoparib, veliparib, WW 46, 2-(4-(trifluoromethyl)phenyl)-7,8-dihydro-5H-thiopyrano[4,3-d]pyrimidin-4-ol, and salts or derivatives thereof. In embodiments, a PARP inhibitor is niraparib, olaparib, rucaparib, talazoparib, or veliparib. In embodiments, a PARP inhibitor is niraparib (e.g., niraparib free base, niraparib tosylate, or niraparib tosylate monohydrate, or any combination thereof).

In embodiments, a subject is further administered or will be administered one or more immune checkpoint inhibitors (e.g., a PD-1 inhibitor and/or a LAG-3 inhibitor) such that the subject receives treatment with a TIM-3 inhibitor, a PARP inhibitor (e.g., niraparib), and the one or more immune checkpoint inhibitors. In embodiments, a subject is administered a TIM-3 inhibitor, a PD-1 inhibitor (e.g., TSR-042) and a PARP inhibitor (e.g., niraparib). In embodiments, a subject is administered a TIM-3 inhibitor, a PD-1 inhibitor (e.g., TSR-042), a LAG-3 inhibitor, and a PARP inhibitor (e.g., niraparib).

In embodiments, a patient has a disorder that is a T-cell dysfunctional disorder.

In embodiments, a patient has a disorder that is cancer.

In embodiments, a cancer is associated with a high tumor mutation burden (TMB).

In embodiments, a cancer is microsatellite stable (MSS).

In embodiments a cancer is characterized by microsatellite instability.

In embodiments, a cancer has a high microsatellite instability status (MSI-H).

In embodiments, a cancer has a low microsatellite instability status (MSI-L).

In embodiments, a cancer is associated with high TMB and MSI-H.

In embodiments, a cancer is associated with high TMB and MSI-L or MSS. In embodiments, a cancer is associated with high TMB and MSI-L. In embodiments, a cancer is associated with high TMB and MSS.

In embodiments, a cancer has a defective DNA mismatch repair system.

In embodiments, a cancer has a defect in a DNA mismatch repair gene.

In embodiments, a cancer is a hypermutated cancer.

In embodiments, a cancer has homologous recombination repair deficiency/homologous repair deficiency ("HRD").

In embodiments, a cancer comprises a mutation in polymerase delta (POLD).

In embodiments, a cancer comprises a mutation in polymerase epsilon (POLE).

In embodiments, a cancer is adenocarcinoma, endometrial cancer, breast cancer, ovarian cancer, cervical cancer, fallopian tube cancer, testicular cancer, primary peritoneal cancer, colon cancer, colorectal cancer, stomach cancer, small intestine cancer, squamous cell carcinoma of the anogenital region (e.g., squamous cell carcinoma of the anus, penis, cervix, vagina, or vulva), soft tissue sarcoma (e.g., leiomyosarcoma), melanoma, renal cell carcinoma, lung cancer, non-small cell lung cancer, adenocarcinoma of the lung, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma (HL)/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor. In embodiments, a cancer is MSS or MSI-L, is characterized by microsatellite instability, is MSI-H, has high TMB, has high TMB and is MSS or MSI-L, has high TMB and is MSI-H, has a defective DNA mismatch repair system, has a defect in a DNA mismatch repair gene, is a hypermutated cancer, is an HRD cancer, comprises a mutation in polymerase delta (POLD) or comprises a mutation in polymerase epsilon (POLE).

In embodiments, a cancer is endometrial cancer (e.g., MSI-H or MSS/MSI-L endometrial cancer). In embodiments, a cancer is a MSI-H cancer comprising a mutation in POLE or POLD (e.g., a MSI-H non-endometrial cancer comprising a mutation in POLE or POLD). In embodiments, a cancer is breast cancer (triple negative breast cancer (TNBC)). In embodiments, a cancer is lung cancer (e.g., non-small cell lung cancer). In embodiments, a cancer is melanoma. In embodiments, a cancer is colorectal cancer. In embodiments, a cancer is squamous cell carcinoma of the anus, squamous cell carcinoma of the penis, squamous cell carcinoma of the cervix, squamous cell carcinoma of the vagina, or squamous cell carcinoma of the vulva.

In embodiments, a cancer has homologous recombination repair deficiency/homologous repair deficiency ("HRD"). In embodiments, a cancer is acute myeloid leukemia. In embodiments, a cancer is acute lymphoblastic leukemia. In embodiments, a cancer is non-Hodgkin's lymphoma. In embodiments, a cancer is Hodgkin's lymphoma. In embodiments, a cancer is neuroblastoma. In embodiments, a cancer is a CNS tumor. In embodiments, a cancer is diffuse intrinsic pontine glioma (DIPG). In embodiments, a cancer is Ewing's sarcoma. In embodiments, a cancer is embryonal rhabdomyosarcoma. In embodiments, a cancer is osteosarcoma. In embodiments, a cancer is Wilms tumor. In embodiments, a cancer is a soft tissue sarcoma (e.g., leiomyosarcoma).

In some embodiments, a patient has cancer, such as: a non-small cell lung cancer (NSCLC), a hepatocellular cancer, a renal cancer, a melanoma, a cervical cancer, a colorectal cancer, a squamous cell carcinoma of the anogenital region, a head and neck cancer, a triple negative breast cancer, an ovarian cancer or an endometrial cancer. In some embodiments, a patient has a cancer with microsatellite instability. In some embodiments, the microsatellite instability is considered high, wherein the instability is significantly higher than that observed in a control cell (e.g., MSI-H status). In some embodiments, the patient has a solid tumor. In some embodiments, the patient has an advanced stage solid tumor. In some embodiments, a patient has an advanced stage solid tumor, such as a non-small cell lung cancer (NSCLC), a hepatocellular cancer, a renal cancer, a melanoma, a cervical cancer, a colorectal cancer, a squamous cell carcinoma of the anogenital region, a head and neck cancer, a triple negative breast cancer, an ovarian cancer or a endometrial cancer. In some embodiments, a patient has an advanced stage solid tumor with microsatellite instability.

In some embodiments, the patient has a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In some embodiments, a patient has a hematological cancer with microsatellite instability.

In some embodiments, a patient has a cancer characterized by PD-1 and/or PD-L1 expression. In some embodiments, a cancer has high PD-1 and/or PD-L1 expression (e.g., by high PD-1 and/or high PD-L1 expression). In some embodiment, a cancer characterized by PD-1 and/or PD-L1 expression is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some certain embodiments, a cancer characterized by PD-1 and/or PD-L1 expression is an anal cancer, a fallopian tube cancer, an ovarian cancer, or a lung cancer.

In some embodiments, the patient has a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, an endometrial cancer, an ovarian cancer, a fallopian tube cancer, a breast cancer, a prostate cancer, a salivary gland tumor, a thymoma, an adrenocortical carcinoma, an esophageal cancer, a gastric cancer, a colorectal cancer, an appendiceal cancer, a urothelial cell carcinoma, or a squamous cell carcinoma.

In embodiments, a cancer is an advanced cancer. In embodiments, a cancer is a metastatic cancer. In embodiments, a cancer is a MSI-H cancer. In embodiments, a cancer is a MSS cancer. In embodiments, a cancer is a POLE-mutant cancer. In embodiments, a cancer is a POLD-mutant cancer. In embodiments, a cancer is a high TMB cancer. In embodiments, a cancer is associated with homologous recombination repair deficiency/homologous repair deficiency ("HRD").

In embodiments, a cancer is a solid tumor. In embodiments, a solid tumor is advanced. In embodiments, a solid tumor is a metastatic solid tumor. In embodiments, a solid tumor is a MSI-H solid tumor. In embodiments, a solid tumor is a MSS solid tumor. In embodiments, a solid tumor is a POLE-mutant solid tumor. In embodiments, a solid tumor is a POLD-mutant solid tumor. In embodiments, a solid tumor is a high TMB solid tumor. In embodiments, a solid tumor is associated with homologous recombination repair deficiency/homologous repair deficiency ("HRD").

In embodiments, a cancer is a non-endometrial cancer (e.g., a non-endometrial solid tumor). In embodiments, a non-endometrial cancer is an advanced cancer. In embodiments, a non-endometrial cancer is a metastatic cancer. In embodiments, a non-endometrial cancer is a MSI-H cancer. In embodiments, a non-endometrial cancer is a MSS cancer. In embodiments, a non-endometrial cancer is a POLE-mutant cancer. In embodiments, a non-endometrial cancer is a solid tumor (e.g., a MSS solid tumor, a MSI-H solid tumor, a POLD mutant solid tumor, or a POLE-mutant solid tumor). In embodiments, a non-endometrial cancer is a high TMB cancer. In embodiments, a non-endometrial cancer is associated with homologous recombination repair deficiency/homologous repair deficiency ("HRD").

In embodiments, a cancer is endometrial cancer (e.g., a solid tumor). In embodiments, an endometrial cancer is an advanced cancer. In embodiments, an endometrial cancer is a metastatic cancer. In embodiments, an endometrial cancer is a MSI-H endometrial cancer. In embodiments, an endometrial cancer is a MSS endometrial cancer. In embodiments, an endometrial cancer is a POLE-mutant endometrial cancer. In embodiments, an endometrial cancer is a POLD-mutant endometrial cancer. In embodiments, an endometrial cancer is a high TMB endometrial cancer. In embodiments, an endometrial cancer is associated with homologous recombination repair deficiency/homologous repair deficiency ("HRD").

In embodiments, a cancer is a lung cancer (e.g., a solid tumor). In embodiments, a lung cancer is an advanced lung cancer. In embodiments, a lung cancer is a metastatic lung cancer. In embodiments, a lung cancer is squamous cell carcinoma of the lung. In embodiments, a lung cancer is small cell lung cancer (SCLC). In embodiments, a lung cancer is non-small cell lung cancer (NSCLC). In embodiments, a lung cancer is an ALK-translocated lung cancer (e.g., a lung cancer with a known ALK-translocation). In embodiments, a lung cancer is an EGFR-mutant lung cancer (e.g., a lung cancer with a known EGFR mutation). In embodiments, a lung cancer is a MSI-H lung cancer. In embodiments, a lung cancer is a MSS lung cancer. In embodiments, a lung cancer is a POLE-mutant lung cancer. In embodiments, a lung cancer is a POLD-mutant lung cancer. In embodiments, a lung cancer is a high TMB lung cancer. In embodiments, a lung cancer is associated with homologous recombination repair deficiency/homologous repair deficiency ("HRD").

In embodiments, a cancer is a colorectal (CRC) cancer (e.g., a solid tumor). In embodiments, a colorectal cancer is an advanced colorectal cancer. In embodiments, a colorectal cancer is a metastatic colorectal cancer. In embodiments, a colorectal cancer is a MSI-H colorectal cancer. In embodiments, a colorectal cancer is a MSS colorectal cancer. In embodiments, a colorectal cancer is a POLE-mutant colorectal cancer. In embodiments, a colorectal cancer is a POLD-mutant colorectal cancer. In embodiments, a colorectal cancer is a high TMB colorectal cancer. In embodiments, a colorectal cancer is associated with homologous recombination repair deficiency/homologous repair deficiency ("HRD").

In embodiments, a cancer is a melanoma. In embodiments, a melanoma is an advanced melanoma. In embodiments, a melanoma is a metastatic melanoma. In embodiments, a melanoma is a MSI-H melanoma. In embodiments, a melanoma is a MSS melanoma. In embodiments, a melanoma is a POLE-mutant melanoma. In embodiments, a melanoma is a POLD-mutant melanoma. In embodiments, a melanoma is a high TMB melanoma. In embodiments, a melanoma is associated with homologous recombination repair deficiency/homologous repair deficiency ("HRD").

In embodiments, a cancer is squamous cell carcinoma of the anogenital region (e.g., of the anus, penis, cervix, vagina, or vulva). In embodiments, a squamous cell carcinoma of the anogenital region (e.g., of the anus, penis, cervix, vagina, or vulva) is an advanced cancer. In embodiments, a squamous cell carcinoma of the anogenital region (e.g., of the anus, penis, cervix, vagina, or vulva) is a metastatic cancer. In embodiments, a squamous cell carcinoma of the anogenital region (e.g., of the anus, penis, cervix, vagina, or vulva) is MSI-H. In embodiments, a squamous cell carcinoma of the anogenital region (e.g., of the anus, penis, cervix, vagina, or vulva) is MSS. In embodiments, a lung cancer is a POLE-mutant cancer. In embodiments, a squamous cell carcinoma of the anogenital region (e.g., of the anus, penis, cervix, vagina, or vulva) is associated with homologous recombination repair deficiency/homologous repair deficiency ("HRD").

In embodiments, a cancer is an ovarian cancer. In embodiments, an ovarian cancer is an advanced ovarian cancer. In embodiments, an ovarian cancer is a metastatic ovarian cancer. In embodiments, an ovarian cancer is a MSI-H ovarian cancer. In embodiments, an ovarian cancer is a MSS ovarian cancer. In embodiments, an ovarian cancer is a POLE-mutant ovarian cancer. In embodiments, an ovarian cancer is a POLD-mutant ovarian cancer. In embodiments, an ovarian cancer is a high TMB ovarian cancer. In embodiments, an ovarian cancer is associated with homologous recombination repair deficiency/homologous repair deficiency ("HRD"). In embodiments, an ovarian cancer is a serous cell ovarian cancer. In embodiments, an ovarian cancer is a clear cell ovarian cancer.

In embodiments, a cancer is a fallopian cancer. In embodiments, a fallopian cancer is an advanced fallopian cancer. In embodiments, a fallopian cancer is a metastatic fallopian cancer. In embodiments, a fallopian cancer is a MSI-H fallopian cancer. In embodiments, a fallopian cancer is a MSS fallopian cancer. In embodiments, a fallopian cancer is a POLE-mutant fallopian cancer. In embodiments, a fallopian cancer is a POLD-mutant fallopian cancer. In embodiments, a fallopian cancer is a high TMB fallopian cancer. In embodiments, a fallopian cancer is associated with homologous recombination repair deficiency/homologous repair deficiency ("HRD"). In embodiments, a fallopian cancer is a serous cell fallopian cancer. In embodiments, a fallopian cancer is a clear cell fallopian cancer.

In embodiments, a cancer is a primary peritoneal cancer. In embodiments, a primary peritoneal cancer is an advanced primary peritoneal cancer. In embodiments, a primary peritoneal cancer is a metastatic primary peritoneal cancer. In embodiments, a primary peritoneal cancer is a MSI-H primary peritoneal cancer. In embodiments, a primary peritoneal cancer is a MSS primary peritoneal cancer. In embodiments, a primary peritoneal cancer is a POLE-mutant primary peritoneal cancer. In embodiments, a primary peritoneal cancer is a POLD-mutant primary peritoneal cancer. In embodiments, a primary peritoneal cancer is a high TMB primary peritoneal cancer. In embodiments, a primary peritoneal cancer is associated with homologous recombination repair deficiency/homologous repair deficiency ("HRD"). In embodiments, a primary peritoneal cancer is a serous cell primary peritoneal cancer. In embodiments, a primary peritoneal cancer is a clear cell primary peritoneal cancer.

In embodiments, a cancer is acute lymphoblastic leukemia ("ALL"). In embodiments, acute lymphoblastic leukemia is advanced acute lymphoblastic leukemia. In embodiments, acute lymphoblastic leukemia is metastatic acute lymphoblastic leukemia. In embodiments, acute lymphoblastic leukemia is MSI-H acute lymphoblastic leukemia. In embodiments, acute lymphoblastic leukemia is MSS acute lymphoblastic leukemia. In embodiments, acute lymphoblastic leukemia is POLE-mutant acute lymphoblastic leukemia. In embodiments, acute lymphoblastic leukemia is POLD-mutant acute lymphoblastic leukemia. In embodiments, an acute lymphoblastic leukemia is associated with homologous recombination repair deficiency/homologous repair deficiency ("HRD").

In embodiments, a cancer is acute myeloid leukemia ("AML"). In embodiments, acute myeloid leukemia is advanced acute myeloid leukemia. In embodiments, acute myeloid leukemia is metastatic acute myeloid leukemia. In embodiments, acute myeloid leukemia is MSI-H acute myeloid leukemia. In embodiments, acute myeloid leukemia is MSS acute myeloid leukemia. In embodiments, acute myeloid leukemia is POLE-mutant acute myeloid leukemia. In embodiments, acute myeloid leukemia is POLD-mutant acute myeloid leukemia. In embodiments, an acute myeloid leukemia is associated with homologous recombination repair deficiency/homologous repair deficiency ("HRD").

In embodiments, a cancer is non-Hodgkin's lymphoma (NHL). In embodiments, non-Hodgkin's lymphoma is advanced non-Hodgkin's lymphoma. In embodiments, non-Hodgkin's lymphoma is metastatic non-Hodgkin's lymphoma. In embodiments, non-Hodgkin's lymphoma is MSI-H non-Hodgkin's lymphoma. In embodiments, non-Hodgkin's lymphoma is MSS non-Hodgkin's lymphoma In embodiments, non-Hodgkin's lymphoma is POLE-mutant non-Hodgkin's lymphoma. In embodiments, non-Hodgkin's lymphoma is POLD-mutant non-Hodgkin's lymphoma. In embodiments, non-Hodgkin's lymphoma is associated with homologous recombination repair deficiency/homologous repair deficiency ("HRD").

In embodiments, a cancer is Hodgkin's lymphoma (HL). In embodiments, Hodgkin's lymphoma is advanced Hodgkin's lymphoma. In embodiments, Hodgkin's lymphoma is metastatic Hodgkin's lymphoma. In embodiments, Hodgkin's lymphoma is MSI-H Hodgkin's lymphoma. In embodiments, Hodgkin's lymphoma is MSS Hodgkin's lymphoma In embodiments, Hodgkin's lymphoma is POLE-mutant Hodgkin's lymphoma. In embodiments, Hodgkin's lymphoma is POLD-mutant Hodgkin's lymphoma. In embodiments, Hodgkin's lymphoma is associated with homologous recombination repair deficiency/homologous repair deficiency ("HRD").

In embodiments, a cancer is a neuroblastoma (NB). In embodiments, a neuroblastoma is an advanced neuroblastoma. In embodiments, a neuroblastoma is a metastatic neuroblastoma. In embodiments, neuroblastoma is a MSI-H neuroblastoma. In embodiments, a neuroblastoma is a MSS neuroblastoma. In embodiments, a neuroblastoma is a POLE-mutant neuroblastoma. In embodiments, a neuroblastoma is a POLD-mutant neuroblastoma. In embodiments, a neuroblastoma is a high TMB neuroblastoma. In embodiments, a neuroblastoma is associated with homologous recombination repair deficiency/homologous repair deficiency ("HRD").

In embodiments, a cancer is a CNS tumor. In embodiments, a CNS tumor is advanced. In embodiments, a CNS tumor is a metastatic CNS tumor. In embodiments, a CNS tumor is a MSI-H CNS tumor. In embodiments, a CNS tumor is a MSS CNS tumor. In embodiments, a CNS tumor is a POLE-mutant CNS tumor. In embodiments, a CNS tumor is a POLD-mutant CNS tumor. In embodiments, a CNS tumor is a high TMB CNS tumor. In embodiments, a CNS tumor is associated with homologous recombination repair deficiency/homologous repair deficiency ("HRD").

In embodiments, a cancer is diffuse intrinsic pontine glioma (DIPG). In embodiments, a DIPG is an advanced DIPG. In embodiments, a DIPG is a metastatic DIPG. In embodiments, DIPG is a MSI-H DIPG. In embodiments, a DIPG is a MSS DIPG. In embodiments, a DIPG is a POLE-mutant DIPG. In embodiments, a DIPG is a POLD-mutant DIPG. In embodiments, a DIPG is a high TMB DIPG. In embodiments, a DIPG is associated with homologous recombination repair deficiency/homologous repair deficiency ("HRD").

In embodiments, a cancer is Ewing's sarcoma. In embodiments, Ewing's sarcoma is an advanced Ewing's sarcoma. In embodiments, Ewing's sarcoma is a metastatic Ewing's sarcoma. In embodiments, Ewing's sarcoma is a MSI-H Ewing's sarcoma. In embodiments, Ewing's sarcoma is a MSS Ewing's sarcoma. In embodiments, Ewing's sarcoma is a POLE-mutant Ewing's sarcoma. In embodiments, Ewing's sarcoma is a POLD-mutant Ewing's sarcoma. In embodiments, Ewing's sarcoma is a high TMB Ewing's sarcoma. In embodiments, Ewing's sarcoma is associated with homologous recombination repair deficiency/homologous repair deficiency ("HRD").

In embodiments, a cancer is an embryonal rhabdomyosarcoma (ERS). In embodiments, an embryonal rhabdomyosarcoma is an advanced embryonal rhabdomyosarcoma. In embodiments, an embryonal rhabdomyosarcoma is a metastatic embryonal rhabdomyosarcoma. In embodiments, an embryonal rhabdomyosarcoma is a MSI-H embryonal rhabdomyosarcoma. In embodiments, an embryonal rhabdomyosarcoma is a MSS embryonal rhabdomyosarcoma. In embodiments, an embryonal rhabdomyosarcoma is a POLE-mutant embryonal rhabdomyosarcoma. In embodiments, an embryonal rhabdomyosarcoma is a POLD-mutant embryonal rhabdomyosarcoma. In embodiments, an embryonal rhabdomyosarcoma is a high TMB embryonal rhabdomyosarcoma. In embodiments, an embryonal rhabdomyosarcoma is associated with homologous recombination repair deficiency/homologous repair deficiency ("HRD").

In embodiments, a cancer is an osteosarcoma (OS). In embodiments, an osteosarcoma is an advanced osteosarcoma. In embodiments, an osteosarcoma is a metastatic osteosarcoma. In embodiments, an osteosarcoma is a MSI-H osteosarcoma. In embodiments, an osteosarcoma is a MSS osteosarcoma. In embodiments, an osteosarcoma is a POLE-mutant osteosarcoma. In embodiments, an osteosarcoma is a POLD-mutant osteosarcoma. In embodiments, an osteosarcoma is a high TMB osteosarcoma. In embodiments, an osteosarcoma is associated with homologous recombination repair deficiency/homologous repair deficiency ("HRD").

In embodiments, a cancer is a soft tissue sarcoma. In embodiments, a soft tissue sarcoma is an advanced soft tissue sarcoma. In embodiments, a soft tissue sarcoma is a metastatic soft tissue sarcoma. In embodiments, a soft tissue sarcoma is a MSI-H soft tissue sarcoma. In embodiments, a soft tissue sarcoma is a MSS soft tissue sarcoma. In embodiments, a soft tissue sarcoma is a POLE-mutant soft tissue sarcoma. In embodiments, a soft tissue sarcoma is a POLD-mutant soft tissue sarcoma. In embodiments, a soft tissue sarcoma is a high TMB soft tissue sarcoma. In embodiments, a soft tissue sarcoma is associated with homologous recombination repair deficiency/homologous repair deficiency ("HRD"). In embodiments, a soft tissue sarcoma is leiomyosarcoma.

In embodiments, a cancer is Wilms tumor. In embodiments, Wilms tumor is an advanced Wilms tumor. In embodiments, Wilms tumor is a metastatic Wilms tumor. In embodiments, Wilms tumor is a MSI-H Wilms tumor. In embodiments, Wilms tumor is a MSS Wilms tumor. In embodiments, Wilms tumor is a POLE-mutant Wilms tumor. In embodiments, Wilms tumor is a POLD-mutant Wilms tumor. In embodiments, Wilms tumor is a high TMB Wilms tumor. In embodiments, Wilms tumor is associated with homologous recombination repair deficiency/homologous repair deficiency ("HRD").

In embodiments, a subject has previously been treated with one or more different cancer treatment modalities (e.g., one or more of surgery, radiotherapy, chemotherapy, or immunotherapy).

In embodiments, a subject has previously been treated with one different cancer treatment modalities (e.g., one or more of surgery, radiotherapy, chemotherapy, or immunotherapy). In embodiments, a subject has previously been treated with two or more different cancer treatment modalities (e.g., one or more of surgery, radiotherapy, chemotherapy, or immunotherapy). In embodiments, a subject has been previously treated with a cytotoxic therapy. In embodiments, a subject has been previously treated with chemotherapy. In embodiments, a subject has previously been treated with two different cancer treatment modalities (e.g., one or more of surgery, radiotherapy, chemotherapy, or immunotherapy). In embodiments, a subject has previously been treated with three different cancer treatment modalities (e.g., one or more of surgery, radiotherapy, chemotherapy, or immunotherapy).

In embodiments of methods described herein, a method further comprises administering one or more of surgery, a radiotherapy, a chemotherapy, an immunotherapy, an anti-angiogenic agent, or an anti-inflammatory. In embodiments, a method further comprises administering a chemotherapy.

In some embodiments, at least some of the patients in the cancer patient population have previously been treated with chemotherapy (e.g., platinum-based chemotherapy). For example, a patient who has received two lines of cancer treatment can be identified as a 2L cancer patient (e.g., a 2L NSCLC patient). In embodiments, a patient has received two lines or more lines of cancer treatment (e.g., a 2L+ cancer patient such as a 2L+ endometrial cancer patient). In embodiments, a patient has not been previously treated with an anti-PD-1 therapy. In embodiments, a patient previously received at least one line of cancer treatment (e.g., a patient previously received at least one line or at least two lines of cancer treatment). In embodiments, a patient previously received at least one line of treatment for metastatic cancer (e.g., a patient previously received one or two lines of treatment for metastatic cancer).

In embodiments, a subject is resistant to treatment with an agent that inhibits PD-1.

In embodiments, a subject is refractory to treatment with an agent that inhibits PD-1.

In embodiments, a method described herein sensitizes a subject to treatment with an agent that inhibits PD-1.

In embodiments, a subject comprises an exhausted immune cell (e.g., an exhausted immune cell that is an exhausted T cell).

In embodiments of methods described herein, a subject is an animal (e.g., a mammal). In embodiments, a subject is a human. In embodiments, a subject is a non-human mammal (e.g., mice, rats, rabbits, or non-human primates). Accordingly, methods described herein can be useful in both treatment of humans and in veterinary medicine.

In embodiments, a TIM-3 inhibitor is administered intravenously (e.g., by intravenous infusion).

The present disclosure provides, in some embodiments, methods of treating cancer in a patient in need thereof, the method comprising administering a composition that delivers an anti-TIM-3 antibody agent.

In some embodiments, the patient has not previously been treated with a cancer treatment modality.

In some embodiments, the patient has previously been treated with one or more different cancer treatment modalities. In some embodiments, the patient has previously been treated with one or more of radiotherapy, chemotherapy or immunotherapy. In some embodiments, the patient has previously been treated with chemotherapy (e.g., platinum-based chemotherapy).

In some embodiments, a composition that delivers a TIM-3 inhibitor (e.g., an anti-TIM-3 antibody agent) is administered at a dose of 1, 3 or 10 mg/kg. In some embodiments, the composition that delivers an anti-TIM-3 antibody agent is administered according to a regimen that includes a dose of 1, 3 or 10 mg/kg every two weeks. In some embodiments, the composition that delivers an anti-TIM-3 antibody agent is administered according to a regimen that includes a dose of 1, 3 or 10 mg/kg every three weeks. In some embodiments, the composition that delivers an anti-TIM-3 antibody agent is administered according to a regimen that includes a dose of 1, 3 or 10 mg/kg every four weeks.

In some embodiments, a composition that delivers an anti-TIM-3 antibody agent at a fixed dose within a range of about 100 mg to about 1500 mg (e.g., about 100 mg to 1500 mg). In some embodiments, a composition that delivers an anti-TIM-3 antibody agent at a fixed dose within a range of about 100 mg to about 300 mg, about 300 mg to about 1,000 mg, or about 1000 mg to about 1200 mg. In embodiments, the fixed dose is about 100 mg. In embodiments, the fixed dose is about 300 mg. In embodiments, the fixed dose is about 500 mg. In embodiments, the fixed dose is about 900 mg. In embodiments, the fixed dose is about 1200 mg. In some embodiments, the composition that delivers an anti-TIM-3 antibody agent is administered according to a regimen that includes a fixed dose every two weeks (Q2W). In some embodiments, the composition that delivers an anti-TIM-3 antibody agent is administered according to a regimen that includes a fixed dose every three weeks (Q3W). In some embodiments, the composition that delivers an anti-TIM-3 antibody agent is administered according to a regimen that includes a fixed dose every four weeks (Q4W). In embodiments, the anti-TIM-3 antibody is administered at the administration interval of once a week (Q1W), once every 2 weeks (Q2W), once every 3 weeks (S3W), once every 4 weeks (Q4W), once every 5 weeks (Q5W), or once every 6 weeks (Q6W). In embodiments, the anti-TIM-3 antibody is administered for the period of at least 2, 4, 6, 8, 10, 12, 14, 16, 18, or 20 weeks. In embodiments, a dose is administered as a monotherapy (e.g., a therapeutically effective amount of 1200 mg of an anti-TIM-3 antibody administered Q2W or Q3W) or a dose is administered in combination with one or more other therapies. For example, 100 mg, 300 mg, 500 mg, or 900 mg (e.g., 100 mg or 300 mg) of an anti-TIM-3 antibody can be administered in combination with an anti-PD-1 antibody according to regiments described herein (e.g., 500 mg of an anti-PD-1 antibody administered Q3W for four treatment cycles followed by administration of 1000 mg of the anti-PD-1 antibody Q6W until treatment is discontinued (e.g., due to disease progression)).

In some embodiments, the composition is administered intravenously. In some embodiments, the composition is administered by intravenous infusion.

In some embodiments, a clinical benefit is a complete response ("CR"), a partial response ("PR") or a stable disease ("SD"). In some embodiments, a clinical benefit corresponds to at least SD. In some embodiments, a clinical benefit corresponds to at least a PR. In some embodiments, a clinical benefit corresponds to a CR. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, at least 5% of patients achieve a clinical benefit. In some embodiments, at least 5% of patients achieve SD. In some embodiments, at least 5% of patients achieve at least a PR. In some embodiments, at least 5% of patients achieve CR. In some embodiments, at least 20% of patients achieve a clinical benefit. In some embodiments, at least 20% of patients achieve SD.

In some embodiments, the clinical benefit (e.g., SD, PR and/or CR) is determined in accordance with Response Evaluation Criteria in Solid Tumors (RECIST). In some embodiments, the clinical benefit (e.g., SD, PR and/or CR) is determined in accordance RECIST guidelines. In some embodiments, the clinical benefit (e.g., SD, PR and/or CR) is determined in accordance RECIST guidelines (version 1.1). In some embodiments, the clinical benefit (e.g., SD, PR and/or CR) is determined in accordance immune-related RECIST (irRECIST) guidelines. In some embodiments, tumor response can be assessed by either irRECIST or RECIST version 1.1. In some embodiments, tumor response can be assessed by both irRECIST and RECIST version 1.1. When used herein, the term "RECIST guidelines" can refer to RECIST 1.0, RECIST 1.1 or it RECIST interchangeably.

In some embodiments, the patient is receiving or will receive an additional therapy in combination with the anti-TIM-3 antibody agent. In some embodiments, the additional therapy is radiotherapy, chemotherapy or immunotherapy. In some embodiments, the additional therapy includes treatment with a composition that delivers a PD-1 inhibitor (e.g., a PD-1-binding agent) and/or a LAG-3-binding agent. In some embodiments, the additional PD-1 inhibitor is nivolumab, pembrolizumab, atezolizumab, durvalumab, avelumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZM009, KN-035, AB122, genolimzumab (CBT-501), FAZ-053, CK-301, AK 104, GLS-010, PD-1VR or PD-1FL, or any of the PD-1 antibodies disclosed in WO2014/179664. In some embodiments, the additional therapy is a PARP inhibitor. In some embodiments, the PARP inhibitor is niraparib, olaparib, rucaparib, talazoparib, and veliparib. In some embodiments, the PARP inhibitor is niraparib.

The present disclosure provides, in some embodiments, methods of treating cancer in a patient in need thereof, the method comprising administering a one or more compositions that deliver an anti-TIM-3 antibody agent in combination with a PD-1-binding agent. In some embodiments, a patient or patient population is receiving a combination therapy that comprises administration of an anti-TIM-3 antibody agent and a PD-1-binding agent (e.g., an anti-PD-1 antibody).

In some embodiments, an anti-TIM-3 antibody agent comprises an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, an anti-TIM-3 antibody agent comprises an immunoglobulin heavy chain whose amino acid sequence comprises SEQ ID NO: 3 and an immunoglobulin light chain whose amino acid sequence comprises SEQ ID NO: 4.

In some embodiments, a PD-1-binding agent comprises an immunoglobulin heavy chain variable domain whose amino acid sequence comprises SEQ ID NO: 11 or SEQ ID NO: 17 and an immunoglobulin light chain variable domain whose amino acid sequence comprises SEQ ID NO: 12 or SEQ ID NO: 18 ("PD-1VR"). In some embodiments, a PD-1-binding agent comprises an immunoglobulin heavy chain whose amino acid sequence comprises SEQ ID NO: 13 and an immunoglobulin light chain whose amino acid sequence comprises SEQ ID NO: 14 ("PD1-FL").

In some embodiments, an anti-TIM-3 antibody agent (e.g., an anti-TIM-3 antibody) is administered at a dose of about 1, 3 or 10 mg/kg. In some embodiments, an anti-TIM-3 antibody agent is administered according to a regimen that includes a dose of 1, 3 or 10 mg/kg every two weeks. In some embodiments, an anti-TIM-3 antibody agent is administered according to a regimen that includes a dose of about 1, 3 or 10 mg/kg every three weeks. In some embodiments, an anti-TIM-3 antibody agent is administered according to a regimen that includes a dose of 1, 3 or 10 mg/kg every four weeks. In some embodiments, an anti-TIM-3 antibody agent is administered at a fixed dose within a range of about 100 mg to 1,500 mg. In some embodiments, an anti-TIM-3 antibody agent is administered at a fixed dose within a range of about 300 mg to 1,000 mg, about 100 mg to about 500 mg, about 100 mg to about 1200 mg, or about 1000 mg to about 1500 mg. In some embodiments, an anti-TIM-3 antibody agent is administered at a fixed dose of about 100, 200 mg, 300 mg, 400 mg, 500 mg, 600 mg, 700 mg, 800 mg, 900 mg, 1000 mg, 1100 mg, 1200 mg, 1300 mg, 1400 mg, or 1500 mg. In some embodiments, an anti-TIM-3 antibody agent is administered at a fixed dose of about 100 mg. In some embodiments, an anti-TIM-3 antibody agent is administered at a fixed dose of about 300 mg. In some embodiments, an anti-TIM-3 antibody agent is administered at a fixed dose of about 500 mg. In some embodiments, an anti-TIM-3 antibody agent is administered at a fixed dose of about 900 mg. In some embodiments, an anti-TIM-3 antibody agent is administered at a fixed dose of about 1200 mg. In some embodiments, an anti-TIM-3 antibody agent is administered according to a regimen that includes a fixed dose every two weeks (Q2W). In some embodiments, an anti-TIM-3 antibody agent is administered according to a regimen that includes a fixed dose every three weeks (Q3W). In some embodiments, an anti-TIM-3 antibody agent is administered according to a regimen that includes a fixed dose every four weeks (Q4W).

In some embodiments, a therapeutically effective dose is a dose of an anti-TIM-3 antibody of about 100 mg to about 1500 mg such as a dose that is about 100, 200, 300, 400, 500, 600, 700, 800, 900, 1000, 1100, 1200 mg, 1300 mg, 1400 mg, or 1500 mg. In embodiments, a therapeutically effective dose is about 100 mg (e.g., administered Q2W or Q3W). In embodiments, a therapeutically effective dose is about 300 mg (e.g., administered Q2W or Q3W). In embodiments, a therapeutically effective dose is about 500 mg (e.g., administered Q2W or Q3W). In embodiments, a therapeutically effective dose is about 900 mg (e.g., administered Q2W or Q3W). In embodiments, a therapeutically effective dose is about 1200 mg (e.g., administered Q2W or Q3W). In embodiments, the anti-TIM-3 antibody is administered at the administration interval of once a week (Q1W), once every 2 weeks (Q2W), once every 3 weeks (S3W), once every 4 weeks (Q4W), once every 5 weeks (Q5W), or once every 6 weeks (Q6W). In embodiments, the anti-TIM-3 antibody is administered for the period of at least 2, 4, 6, 8, 10, 12, 14, 16, 18, or 20 weeks.

In embodiments, a therapeutically effective dose is about 100 mg, and the agent is administered at an administration interval of once every 2 weeks. In embodiments, a therapeutically effective dose is about 100 mg, and the agent is administered at an administration interval of once every 3 weeks.

In embodiments, a therapeutically effective dose is about 300 mg, and the agent is administered at an administration interval of once every 2 weeks. In embodiments, a therapeutically effective dose is about 300 mg, and the agent is administered at an administration interval of once every 3 weeks.

In embodiments, a therapeutically effective dose is about 500 mg, and the agent is administered at an administration interval of once every 2 weeks. In embodiments, a therapeutically effective dose is about 500 mg, and the agent is administered at an administration interval of once every 3 weeks.

In embodiments, a therapeutically effective dose is about 900 mg, and the agent is administered at an administration interval of once every 2 weeks. In embodiments, a therapeutically effective dose is about 900 mg, and the agent is administered at an administration interval of once every 3 weeks.

In embodiments, a therapeutically effective dose is about 1200 mg, and the agent is administered at an administration interval of once every 2 weeks. In embodiments, a therapeutically effective dose is about 1200 mg, and the agent is administered at an administration interval of once every 3 weeks.

In embodiments, a dose is administered as a monotherapy (e.g., a therapeutically effective amount of 1200 mg of an anti-TIM-3 antibody administered Q2W or Q3W) or a dose is administered in combination with one or more other therapies. For example, 100 mg or 300 mg of an anti-TIM-3 antibody can be administered in combination with an anti-PD-1 antibody according to regiments described herein (e.g., 500 mg of an anti-PD-1 antibody administered Q3W for four treatment cycles followed by administration of 1000 mg of the anti-PD-1 antibody Q6W until treatment is discontinued (e.g., due to disease progression)).

In some embodiments, a PD-1-binding agent (e.g., an anti-PD-1 antibody) is administered at a dose of 0.1, 1, 3 10, or 20 mg/kg. In some embodiments, a PD-1-binding agent (e.g., an anti-PD-1 antibody) is administered according to a regimen that includes a dose of 1, 3 or 10 mg/kg every two weeks. In some embodiments, a PD-1-binding agent (e.g., an anti-PD-1 antibody) is administered according to a regimen that includes a dose of 1, 3 or 10 mg/kg every three weeks. In some embodiments, a PD-1-binding agent (e.g., an anti-PD-1 antibody) is administered according to a regimen that includes a dose of 1, 3 or 10 mg/kg every four weeks. In some embodiments, a PD-1-binding agent (e.g., an anti-PD-1 antibody) at a dose of 500 mg. In some embodiments, a PD-1-binding agent (e.g., an anti-PD-1 antibody) is administered according to a regimen that includes a dose of 500 mg every two weeks. In some embodiments, a PD-1-binding agent (e.g., an anti-PD-1 antibody) is administered according to a regimen that includes a dose of 500 mg every three weeks. In some embodiments, a PD-1-binding agent (e.g., an anti-PD-1 antibody) is administered according to a regimen that includes a dose of 500 mg every four weeks. In some embodiments, a PD-1-binding agent (e.g., an anti-PD-1 antibody) is administered according to a regimen that includes a dose of 500 mg every three weeks for at least one treatment cycle (e.g., for at least one, two, three, or four treatment cycles), followed by administration. In some embodiments, a PD-1-binding agent (e.g., an anti-PD-1 antibody) is administered according to a regimen that includes a dose of 1000 mg every three weeks. In some embodiments, a PD-1-binding agent (e.g., an anti-PD-1 antibody) is administered according to a regimen that includes a dose of 1000 mg every four weeks. In some embodiments, a PD-1-binding agent (e.g., an anti-PD-1 antibody) is administered according to a regimen that includes a dose of 1000 mg every five weeks. In some embodiments, a PD-1-binding agent (e.g., an anti-PD-1 antibody) is administered according to a regimen that includes a dose of 1000 mg every six weeks. In embodiments, a PD-1-binding agent (e.g., an anti-PD-1 antibody) is administered according to a regimen that includes a dose of 500 mg every three weeks for four treatment cycles, followed by administration of a dose of 1000 mg every six weeks until treatment is discontinued (e.g., due to disease progression). In embodiments, an anti-TIM-3 antibody agent is administered Q2W or Q3W in a dose that is about 100, 200, 300, 400, 500, 600, 700, 800, 900, 1000, 1100, or 1200 mg or in a dose that is about 1-10 mg/kg (e.g, a dose that is about 1, about 3, or about 10 mg/kg). In embodiments, an anti-TIM-3 antibody agent is administered Q2W or Q3W in a dose that is about 100 mg. In embodiments, an anti-TIM-3 antibody agent is administered Q2W or Q3W in a dose that is about 300 mg.

In embodiments, a PD-1 inhibitor (e.g., any anti-PD-1 antibody described herein) is administered at a first dose of about 500 mg once every 3 weeks for 3, 4, or 5 cycles followed by a second dose of about 1000 mg once every 6 weeks or more (e.g., a second dose of about 1000 mg once every 6 weeks). In embodiments, a therapeutically effective dose of the agent (e.g., an anti-TIM-3 antibody) is a flat dose about 100 mg. In embodiments, a therapeutically effective dose of the agent (e.g., an anti-TIM-3 antibody) is a flat dose about 300 mg. In embodiments, a therapeutically effective dose of the agent (e.g., an anti-TIM-3 antibody) is a flat dose about 500 mg. In embodiments, a therapeutically effective dose of the agent (e.g., an anti-TIM-3 antibody) is a flat dose about 900 mg. In embodiments, a therapeutically effective dose of the agent (e.g., an anti-TIM-3 antibody) is administered once every three weeks.

In embodiments, a PD-1 inhibitor (e.g., any anti-PD-1 antibody described herein) is administered at a first dose of about 500 mg once every 3 weeks for 3 cycles followed by a second dose of about 1000 mg once every 6 weeks or more (e.g., a second dose of about 1000 mg once every 6 weeks). In embodiments, a therapeutically effective dose of the agent (e.g., an anti-TIM-3 antibody) is a flat dose about 100 mg. In embodiments, a therapeutically effective dose of the agent (e.g., an anti-TIM-3 antibody) is a flat dose about 300 mg. In embodiments, a therapeutically effective dose of the agent (e.g., an anti-TIM-3 antibody) is a flat dose about 500 mg. In embodiments, a therapeutically effective dose of the agent (e.g., an anti-TIM-3 antibody) is a flat dose about 900 mg. In embodiments, a therapeutically effective dose of the agent (e.g., an anti-TIM-3 antibody) is administered once every three weeks.

In embodiments, a PD-1 inhibitor (e.g., any anti-PD-1 antibody described herein) is administered at a first dose of about 500 mg once every 3 weeks for 4 cycles followed by a second dose of about 1000 mg once every 6 weeks or more (e.g., a second dose of about 1000 mg once every 6 weeks). In embodiments, a therapeutically effective dose of the agent (e.g., an anti-TIM-3 antibody) is a flat dose about 100 mg. In embodiments, a therapeutically effective dose of the agent (e.g., an anti-TIM-3 antibody) is a flat dose about 300 mg. In embodiments, a therapeutically effective dose of the agent (e.g., an anti-TIM-3 antibody) is a flat dose about 500 mg. In embodiments, a therapeutically effective dose of the agent (e.g., an anti-TIM-3 antibody) is a flat dose about 900 mg. In embodiments, a therapeutically effective dose of the agent (e.g., an anti-TIM-3 antibody) is administered once every three weeks.

In embodiments, a PD-1 inhibitor (e.g., any anti-PD-1 antibody described herein) is administered at a first dose of about 500 mg once every 3 weeks for 5 cycles followed by a second dose of about 1000 mg once every 6 weeks or more (e.g., a second dose of about 1000 mg once every 6 weeks). In embodiments, a therapeutically effective dose of the agent (e.g., an anti-TIM-3 antibody) is a flat dose about 100 mg.

In embodiments, a therapeutically effective dose of the agent (e.g., an anti-TIM-3 antibody) is a flat dose about 300 mg. In embodiments, a therapeutically effective dose of the agent (e.g., an anti-TIM-3 antibody) is a flat dose about 500 mg. In embodiments, a therapeutically effective dose of the agent (e.g., an anti-TIM-3 antibody) is a flat dose about 900 mg. In embodiments, a therapeutically effective dose of the agent (e.g., an anti-TIM-3 antibody) is administered once every three weeks.

The present disclosure provides, in some embodiments, compositions comprising an anti-TIM-3 antibody agent for use in treatment of cancer in a selected cancer patient population. In some embodiments, an anti-TIM-3 antibody agent comprises a heavy chain comprising three CDRs that have sequences of SEQ ID NOs: 21, 22, or 23. In some embodiments, an anti-TIM-3 antibody agent comprises a light chain comprising three CDRs that have sequences of SED ID NOs: 24, 25, or 26. In some embodiments, an anti-TIM-3 antibody agent comprises a heavy chain comprising three CDRs that have sequences of SEQ ID NOs: 21, 22, or 23; and a light chain comprising three CDRs that have sequences of SED ID NOs: 24, 25, or 26. In some embodiments, an anti-TIM-3 antibody agent comprises an immunoglobulin heavy chain variable domain whose amino acid sequence comprises SEQ ID NO: 1 or SEQ ID NO:7. In some embodiments, an anti-TIM-3 antibody agent comprises an immunoglobulin light chain variable domain whose amino acid sequence comprises SEQ ID NO: 2 or SEQ ID NO: 8. In some embodiments, an anti-TIM-3 antibody agent comprises an immunoglobulin heavy chain variable domain whose amino acid sequence comprises SEQ ID NO: 1 or SEQ ID NO:7 and an immunoglobulin light chain variable domain whose amino acid sequence comprises SEQ ID NO: 2 or SEQ ID NO: 8. In some embodiments, an anti-TIM-3 antibody agent comprises an immunoglobulin heavy chain whose amino acid sequence comprises SEQ ID NO: 3. In some embodiments, an anti-TIM-3 antibody agent comprises an immunoglobulin light chain whose amino acid sequence comprises SEQ ID NO: 4. In some embodiments, an anti-TIM-3 antibody agent comprises an immunoglobulin heavy chain whose amino acid sequence comprises SEQ ID NO: 3 and an immunoglobulin light chain whose amino acid sequence comprises SEQ ID NO: 4.

In some embodiments, the patients in the cancer patient population each have a tumor. In some embodiments, the patients in the cancer patient population each have a solid tumor. In some embodiments, at least some of the patients in the cancer patient population have an advanced stage solid tumor. In some embodiments, at least some of the patients in the cancer patient population have a metastatic solid tumor. In some embodiments, the patient has a MSI-H solid tumor. In some embodiments, the patients in the cancer patient population each have a cancer such as a non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer.

In embodiments, the patient has a lung cancer (e.g., non-small cell lung cancer (NSCLC). In embodiments, the patient has a melanoma.

In some embodiments, the patient has a cancer associated with a POLE (DNA polymerase epsilon) or a POLD (DNA polymerase delta) mutation. In some embodiments, the POLE or POLD mutation is in an exonuclease domain. In some embodiments, the POLE or POLD mutation is a germline mutation. In some embodiments, the POLE or POLD mutation is a sporadic mutation. In some embodiments, a method described herein further comprises a step of first identifying the patient having the cancer with the POLE or POLD mutation. In some embodiments, a POLE or POLD mutation is identified using sequencing.

In some embodiments, the patients in the cancer patient population each have a cancer with microsatellite instability. In some embodiments, the microsatellite instability is considered high, wherein the instability is significantly higher than that observed in a control cell (e.g., MSI-H status). In some embodiments, the microsatellite instability is MSI-Low (MSI-L). In some embodiments, the microsatellite instability is microsatellite stable (e.g., MSS status). In some embodiments, a patient has an advanced stage solid tumor with microsatellite instability.

In some embodiments, the patients in the cancer patient population each have a hematological cancer. In some embodiments, the patients in the cancer patient population each have a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In some embodiments, the patients in the cancer patient population each have a hematological cancer with microsatellite instability.

In some embodiments, at least some of the patients in the cancer patient population have previously been treated with one or more different cancer treatment modalities. In some embodiments, at least some of the patients in the cancer patient population have previously been treated with one or more of radiotherapy, chemotherapy or immunotherapy. In some embodiments, at least some of the patients in the cancer patient population have previously been treated with chemotherapy (e.g., platinum-based chemotherapy).

In some embodiments, at least some of the patients in the cancer patient population have not previously been treated with one or more different cancer treatment modalities.

The present disclosure provides, in some embodiments, a combination therapy for use in treatment of cancer in a selected cancer patient population, wherein the combination therapy comprises administering an anti-TIM-3 antibody agent and a PD-1-binding agent.

BRIEF DESCRIPTION OF THE DRAWINGS

FIG. 5 describes patient demographics and baseline characteristics for participants in the dose-escalation study.

DETAILED DESCRIPTION OF CERTAIN EMBODIMENTS

Definitions

Figure 1:
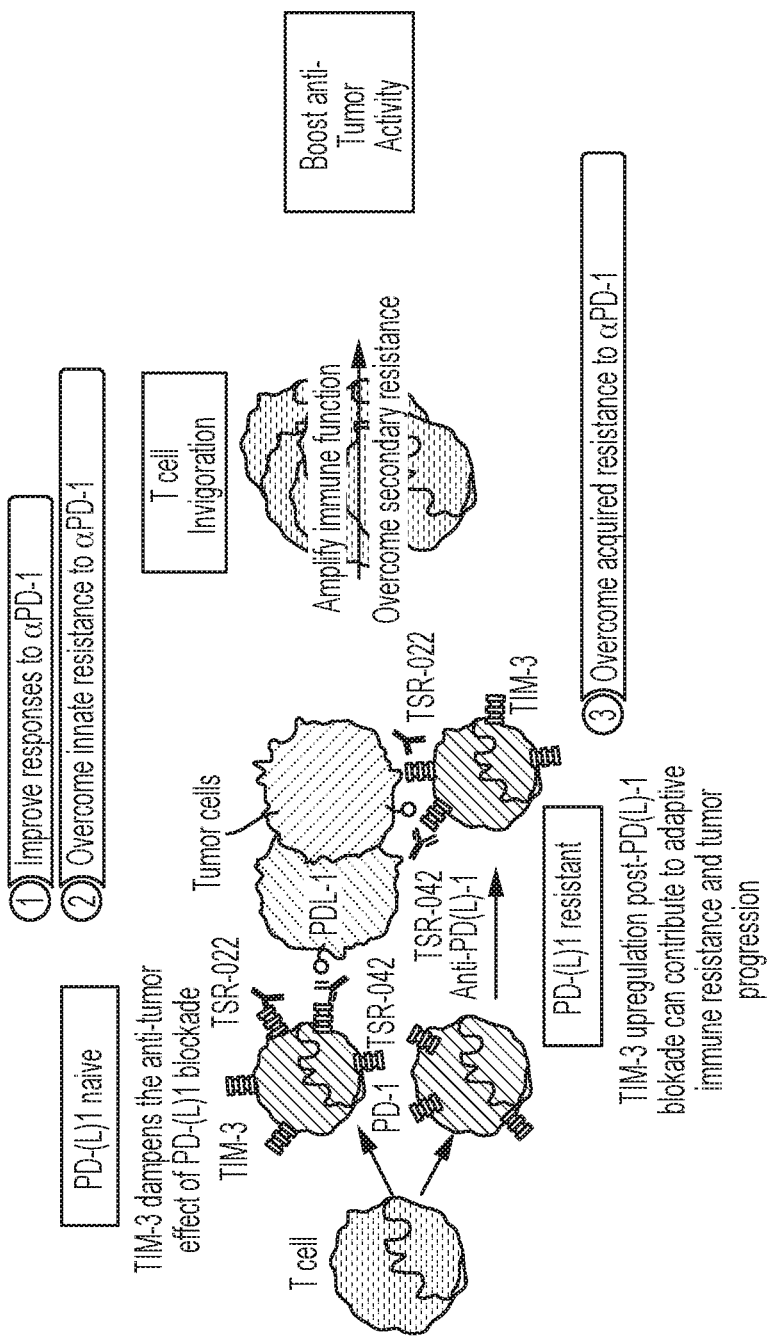
FIG. 1 depicts a schematic illustration, not to scale, of enhancement of immune cell activation by anti-TIM-3 and anti-PD1.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. Examples of routes of administration include parenteral, e.g., intravenous, intradermal, subcutaneous, oral (e.g., inhalation), transdermal (i.e., topical), transmucosal, and rectal administration. For example, in some embodiments, administration may be ocular, oral, parenteral, topical, etc. In embodiments, administration is parenteral (e.g., intravenous administration). In embodiments, intravenous administration is intravenous infusion. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complementarity determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR® s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.].

Antibodies include antibody fragments. Antibodies also include, but are not limited to, polyclonal monoclonal, chimeric dAb (domain antibody), single chain, $F_{ab}$, $F_{ab'}$, $F_{(ab')2}$ fragments, scFvs, and $F_{ab}$ expression libraries. An antibody may be a whole antibody, or immunoglobulin, or an antibody fragment.

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR® s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]. In many embodiments, an antibody agent is or comprises a polypeptide whose amino acid sequence includes one or more structural elements recognized by those skilled in the art as a complementarity determining region (CDR); in some embodiments, an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell). In some embodiments, "binding" refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

Binding agent: In general, the term "binding agent" is used herein to refer to any entity that binds to a target of interest as described herein. In many embodiments, a binding agent of interest is one that binds specifically with its target in that it discriminates its target from other potential binding partners in a particular interaction context. In general, a binding agent may be or comprise an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding moiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise nucleic acids, such as DNA or RNA.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components. In some embodiments, the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Combination therapy: As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Complete Response: As used herein, the term "complete response" or "CR" is used to mean the disappearance of all or substantially all target lesions. In some embodiments, CR refers to an about 80%, 85%, 90%, 91%, 92%, 93%, 94%, 95%, 96%, 97%, 98%, 99% or 100% decrease in the sum of the diameters of the target lesions (i.e., loss of lesions), taking as reference the baseline sum diameters. In some embodiments, CR indicates that less than about 10%, 9%, 8%, 7%, 6%, 5%, 4%, 3%, 2%, 1% or less of the total lesion diameter remains after treatment. Exemplary methods for evaluating complete response are identified by RECIST guidelines. See, e.g., E. A. Eisenhauer, et al., "New response evaluation criteria in solid tumors: Revised RECIST guideline (version 1.1)," *Eur. J. of Cancer,* 45: 228-247 (2009).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or regimen: Those skilled in the art will appreciate that the term "regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen). In some embodiments, a regimen comprises at least one dose, wherein the dose comprises one unit dose of a therapeutic agent (e.g., an anti-TIM-3 antibody agent). In some embodiments, a regimen comprises at least one dose, wherein the dose comprises two or more unit doses of a therapeutic agent. For example, a dose of 500 mg can be administered as a single 500 mg unit dose or as two 250 mg unit doses. In some embodiments, a regimen is correlated with or result in a desired or beneficial outcome when administered across a relevant population (i.e., is a therapeutic regimen).

Hazard Ratio: As used herein, a "hazard ratio" is the expression of the hazard or chance of events occurring in the treatment arm as a ratio of the events occurring in the control arm. Hazard ratios may be determined by the Cox model, a regression method for survival data, which provides an estimate of the hazard ratio and its confidence interval. The hazard ratio is an estimate of the ratio of the hazard rate in the treated versus the control group. The hazard rate is the probability that if the event in question has not already occurred, it will occur in the next time interval, divided by the length of that interval. An assumption of proportional hazards regression is that the hazard ratio is constant over time.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix $K_D$: as used herein, refers to the dissociation constant of a binding agent (e.g., an antibody or binding component thereof) from a complex with its partner (e.g., the epitope to which the antibody or binding component thereof binds).

$K_{off}$: as used herein, refers to the off rate constant for dissociation of a binding agent (e.g., an antibody or binding component thereof) from a complex with its partner (e.g., the epitope to which the antibody or binding component thereof binds).

$K_{on}$: as used herein, refers to the on rate constant for association of a binding agent (e.g., an antibody or binding component thereof) with its partner (e.g., the epitope to which the antibody or binding component thereof binds).

Patient or subject: As used herein, the term "patient" or "subject" refers to any organism to which provided compound or compounds described herein are administered in accordance with the present invention e.g., for experimental, diagnostic, prophylactic, and/or therapeutic purposes. Typical subjects include animals. The term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone. In embodiments, animals are mammals such as mice, rats, rabbits, non-human primates, and humans; insects; worms; etc. In a preferred embodiment, a subject is a human. In some embodiments, a subject may be suffering from, and/or susceptible to a disease, disorder, and/or condition (e.g., cancer). As used herein, a "patient population" or "population of subjects" refers to a plurality of patients or subjects.

Partial Response: As used herein, the term "partial response" ("PR") refers to a decrease in tumor progression in a subject as indicated by a decrease in the sum of the diameters of the target lesions, taking as reference the baseline sum diameters. In some embodiments, PR refers to at least a 30% decrease in the sum of diameters or target lesions, taking as reference the baseline sum diameters. Exemplary methods for evaluating partial response are identified by RECIST guidelines. See e.g, E. A. Eisenhauer, et al., "New response evaluation criteria in solid tumors: Revised RECIST guideline (version 1.1)," *Eur. J. of Cancer*, 45: 228-247 (2009).

Pharmaceutical composition: As used herein, the term "pharmaceutical composition" refers to a composition in which an active agent (e.g., an anti-TIM-3 antibody agent and/or a PD-1-binding agent) is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some preferred embodiments, an active agent (e.g., an anti-TIM-3 antibody agent and/or a PD-1-binding agent) is formulated for parenteral administration.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Progression Free Survival: As used herein, the term "progression free survival" means the time period for which a subject having a disease (e.g., cancer) survives, without a significant worsening of the disease state. Progression free survival may be assessed as a period of time in which there is no progression of tumor growth and/or wherein the disease status of a patient is not determined to be a progressive disease. In some embodiments, progression free survival of a subject having cancer is assessed by evaluating tumor (lesion) size, tumor (lesion) number, and/or metastasis.

Progression or Progressive Disease: The term "progression" of tumor growth or a "progressive disease" ("PD") as used herein in reference to cancer status indicates an increase in the sum of the diameters of the target lesions (tumors). In some embodiments, progression of tumor growth refers to at least a 20% increase in the sum of diameters of target lesions, taking as reference the smallest sum on study (this includes the baseline sum if that is the smallest on study). In some embodiments, in addition to a relative increase of 20%, the sum of diameters of target lesions must also demonstrate an absolute increase of at least 5 mm. An appearance of one or more new lesions may also be factored into the determination of progression of tumor growth. Progression for the purposes of determining progression free survival may also be determined if at least one of the following criteria is met: 1) tumor assessment by CT/MRI unequivocally shows progressive disease according to RECIST 1.1 or irRECIST criteria; or 2) additional diagnostic tests (e.g., histology/cytology, ultrasound techniques, endoscopy, positron emission tomography) identify new lesions or determine existing lesions qualify for unequivocal progressive disease AND CA-125-progression according to Gynecologic Cancer Intergroup (GCIG)-criteria (see Rustin et al., Int J Gynecol Cancer 2011; 21: 419-423 which is incorporated herein in its entirety); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion) AND CA-125-progression according to GCIG-criteria.

Solid Tumor: As used herein, the term "solid tumor" refers to an abnormal mass of tissue that usually does not contain cysts or liquid areas. In some embodiments, a solid tumor may be benign; in some embodiments, a solid tumor may be malignant. Those skilled in the art will appreciate that different types of solid tumors are typically named for the type of cells that form them. Examples of solid tumors are carcinomas, lymphomas, and sarcomas. In some embodiments, solid tumors may be or comprise adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stabilization or Stable Disease: As used herein, "stabilization" of tumor growth or a "stable disease" ("SD") refers to neither sufficient shrinkage to qualify for PR nor sufficient increase to qualify for PD. In some embodiments, stabilization refers to a less than 30%, 25%, 20%, 15%, 10% or 5% change (increase or decrease) in the sum of the diameters of the target lesions, taking as reference the baseline sum diameters. Exemplary methods for evaluating stabilization of tumor growth or a stable disease are identified by RECIST guidelines. See e.g., E. A. Eisenhauer, et al., "New response evaluation criteria in solid tumors: Revised RECIST guideline (version 1.1)," *Eur. J. of Cancer*, 45: 228-247 (2009).

Therapeutically Effective Amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Methods of Treatment, Including Methods of Treating Cancer

Described herein are methods of treating disorders in a subject (e.g., disorders that benefit from administration of an anti-TIM-3 therapy). For example, an anti-TIM-3 therapy described herein can agent is administered e.g., as a monotherapy or in combination therapy, for a period sufficient to achieve clinical benefit or according to a regimen as determined by a physician (e.g., an anti-TIM-3 therapy is administered in dosage amounts and number of treatment cycles as determined by a physician).

In embodiments, methods described herein are useful for increasing T cell activation or T cell effector function in a subject.

In embodiments, methods described herein are useful for inducing an immune response in a subject.

In embodiments, methods described herein are useful for enhancing an immune response or increasing the activity of an immune cell in a subject.

The inventive methods can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)). When the inventive method treats an infectious disease, an anti-TIM-3 antibody agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

The inventive methods can be used to treat any type of autoimmune disease (i.e., as disease or disorder caused by immune system over-activity in which the body attacks and damages its own tissues), such as those described in, for example, MacKay I. R. and Rose N. R., eds., *The Autoimmune Diseases, Fifth Edition*, Academic Press, Waltham, MA (2014). Examples of autoimmune diseases that can be treated by the inventive method include, but are not limited to, multiple sclerosis, type 1 diabetes mellitus, rheumatoid arthritis, scleroderma, Crohn's disease, psoriasis, systemic lupus erythematosus (SLE), and ulcerative colitis. When the inventive method treats an autoimmune disease, an anti-TIM-3 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In embodiments, methods described herein are useful for treating T-cell dysfunctional disorders (e.g., cancer).

In embodiments, methods described herein are useful for reducing tumors or inhibiting the growth of tumor cells in a subject.

The inventive methods can be used to treat any type of cancer known in the art.

In embodiments, a cancer is adenocarcinoma, adenocarcinoma of the lung, acute myeloid leukemia ("AML"), acute lymphoblastic leukemia ("ALL"), adrenocortical carcinoma, anal cancer, appendiceal cancer, B-cell derived leukemia, B-cell derived lymphoma, bladder cancer, brain cancer, breast cancer (e.g., triple negative breast cancer (TNBC)), cancer of the fallopian tube(s), cancer of the testes, cerebral cancer, cervical cancer, choriocarcinoma, chronic myelogenous leukemia, a CNS tumor, colon adenocarcinoma, colon cancer, colorectal cancer, diffuse intrinsic pontine glioma (DIPG), diffuse large B cell lymphoma ("DLBCL"), embryonal rhabdomyosarcoma (ERMS), endometrial cancer, epithelial cancer, esophageal cancer, Ewing's sarcoma, follicular lymphoma ("FL"), gall bladder cancer, gastric cancer, gastrointestinal cancer, glioma, head and neck cancer, a hematological cancer, hepatocellular cancer, Hodgkin's lymphoma (HL)/primary mediastinal B-cell lymphoma, kidney cancer, kidney clear cell cancer, laryngeal cancer, leukemia, liver cancer, lung cancer, lymphoma, melanoma, Merkel cell carcinoma, mesothelioma, monocytic leukemia, multiple myeloma, myeloma, a neuroblastic-derived CNS tumor (e.g., neuroblastoma (NB)), non-Hodgkin's lymphoma (NHL), non-small cell lung cancer (NSCLC), oral cancer, osteosarcoma, ovarian cancer, ovarian carcinoma, pancreatic cancer, peritoneal cancer, primary peritoneal cancer, prostate cancer, relapsed or refractory classic Hodgkin's Lymphoma (cHL), renal cell carcinoma, rectal cancer, salivary gland cancer (e.g., a salivary gland tumor), sarcoma, skin cancer, small cell lung cancer, small intestine cancer, squamous cell carcinoma of the anogenital region (e.g., squamous cell carcinoma of the anus, penis, cervix, vagina, or vulva), squamous cell carcinoma of the esophagus, squamous cell carcinoma of the head and neck (SCHNC), squamous cell carcinoma of the lung, stomach cancer, T-cell derived leukemia, T-cell derived lymphoma, thymic cancer, a thymoma, thyroid cancer, uveal melanoma, urothelial cell carcinoma, uterine cancer, uterine endometrial cancer, uterine sarcoma, vaginal cancer, vulvar cancer, or Wilms tumor.

In other embodiments, a cancer is a head and neck cancer, a lung cancer (e.g., a non-small cell lung cancer (NSCLC)), a renal cancer, a bladder cancer, a melanoma, Merkel cell carcinoma (see, e.g., Bhatia et al., Curr. Oncol. Rep., 13(6): 488-497 (2011), a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some embodiments, a cancer for treatment in the context of the present disclosure is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

In embodiments a cancer is a lymphoma such as Hodgkin's disease, non-Hodgkin's Lymphoma, Multiple myeloma, Waldenstrom's macroglobulinemia, Heavy chain disease and Polycythemia vera.

In embodiments, a cancer is a squamous cell carcinoma. In embodiments, a cancer is squamous cell carcinoma of the lung. In embodiments, a cancer is squamous cell carcinoma of the esophagus. In embodiments, a cancer is squamous cell carcinoma of the anogenital region (e.g., of the anus, penis, cervix, vagina, or vulva). In embodiments, a cancer is head and neck squamous cell carcinoma (HNSCC).

In embodiments, a cancer is bladder cancer, breast cancer (e.g., triple negative breast cancer (TNBC)), cancer of the fallopian tube(s), cholagiocarcinoma, colon adenocarcinoma, endometrial cancer, esophageal cancer, Ewing's sarcoma, gastric cancer, kidney clear cell cancer, lung cancer (e.g., lung adenocarcinoma or lung squamous cell cancer), mesothelioma, ovarian cancer, pancreatic cancer, peritoneal cancer, prostate cancer, uterine endometrial cancer, or uveal melanoma. In embodiments, a cancer is ovarian cancer, cancer of the fallopian tube(s), or peritoneal cancer. In embodiments, a cancer is breast cancer (e.g., TNBC). In embodiments, a cancer is lung cancer (e.g., non-small cell lung cancer). In embodiments, a cancer is prostate cancer.

In embodiments, a cancer is a CNS or brain cancer such as neuroblastoma (NB), glioma, diffuse intrinsic pontine glioma (DIPG), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor, or medulloblastoma. In embodiments, a cancer is a CNS tumor.

In other embodiments, a cancer is melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma (see, e.g., Bhatia et al., Curr. Oncol. Rep., 13(6): 488-497 (2011)).

In some embodiments, a patient or population of patients have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), acute lymphoblastic leukemia ("ALL"), or Multiple myeloma ("MM"). In embodiments, a cancer is a blood-borne cancer such as acute lymphoblastic leukemia("ALL"), acute lymphoblastic B-cell leukemia, acute lymphoblastic T-cell leukemia, acute myeloblastic leukemia ("AML"), acute lymphoblastic leukemia ("ALL"), acute promyelocytic leukemia("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia("CLL"), hairy cell leukemia and multiple myeloma; acute and chronic leukemias such as lymphoblastic, myelogenous, lymphocytic, and myelocytic leukemias.

In some embodiments, a patient or population of patients have a solid tumor. In embodiments, a cancer is a solid tumor such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, osteosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, non small cell lung cancer (NSCLC), small cell lung carcinoma, bladder carcinoma, lung cancer, epithelial carcinoma, skin cancer, melanoma, neuroblastoma (NB), or retinoblastoma. In some embodiments, the tumor is an advanced stage solid tumor. In some embodiments, the tumor is a metastatic solid tumor. In some embodiments, the patient has a MSI-H solid tumor.

In some embodiments, a patient or population of patients to be treated by the methods of the present invention have or are susceptible to cancer, such as a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some embodiments, a patient or population of patients to be treated by the methods of the present invention have or are susceptible to lung cancer (e.g., NSCLC), renal cancer, melanoma, cervical cancer, colorectal cancer, or endometrial cancer (e.g., MSS endometrial cancer or MSI-H endometrial cancer).

In some embodiments, a patient or population of patients to be treated by the methods of the present invention have or are susceptible to non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer. In some embodiments, a patient has an advanced stage solid tumor, such as a non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer. In some embodiments, a patient has an advanced stage solid tumor with microsatellite instability.

In some embodiments, a cancer is a gynecologic cancer (i.e., a cancer of the female reproductive system such as ovarian cancer, fallopian tube cancer, cervical cancer, vaginal cancer, vulvar cancer, uterine cancer, or primary peritoneal cancer, or breast cancer). In some embodiments, cancers of the female reproductive system include, but are not limited to, ovarian cancer, cancer of the fallopian tube(s), peritoneal cancer, and breast cancer.

In embodiments, a cancer is ovarian cancer (e.g., serous or clear cell ovarian cancer). In embodiments, a cancer is fallopian tube cancer (e.g., serous or clear cell fallopian tube cancer). In embodiments, a cancer is primary peritoneal cancer (e.g., serous or clear cell primary peritoneal cancer).

In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, call the peritoneum. In some embodiments, the cancer is or comprises a germ cell tumor. Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis. In some embodiments, a gynecologic cancer is associated with homologous recombination repair deficiency/homologous repair deficiency ("HRD") and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy (e.g., a partial or complete response to the last platinum-based therapy or to the penultimate platinum-based therapy). In some embodiments, a gynecologic cancer is now resistant to platinum-based therapy.

In embodiments, a cancer is a breast cancer. Usually breast cancer either begins in the cells of the milk producing glands, known as the lobules, or in the ducts. Less commonly breast cancer can begin in the stromal tissues. These include the fatty and fibrous connective tissues of the breast. Over time the breast cancer cells can invade nearby tissues such the underarm lymph nodes or the lungs in a process known as metastasis. The stage of a breast cancer, the size of the tumor and its rate of growth are all factors which determine the type of treatment that is offered. Treatment options include surgery to remove the tumor, drug treatment which includes chemotherapy and hormonal therapy, radiation therapy and immunotherapy. The prognosis and survival rate varies widely; the five year relative survival rates vary from 98% to 23% depending on the type of breast cancer that occurs. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2. In some embodiments, triple negative breast cancer (TNBC) is characterized as breast cancer cells that are estrogen receptor expression negative (<1% of cells), progesterone receptor expression negative (<1% of cells), and HER2-negative.

In embodiments, a cancer is ER-positive breast cancer, ER-negative breast cancer, PR-positive breast cancer, PR-negative breast cancer, HER2-positive breast cancer, HER2-negative breast cancer, BRCA1/2-positive breast cancer, BRCA1/2-negative cancer, or triple negative breast cancer (TNBC). In embodiments, a cancer is triple negative breast cancer (TNBC). In some embodiments, a breast cancer is a metastatic breast cancer. In some embodiments, a breast cancer is an advanced breast cancer. In some embodiments, a cancer is a stage II, stage III or stage IV breast cancer. In some embodiments, a cancer is a stage IV breast cancer. In some embodiments, a breast cancer is a triple negative breast cancer.

In some embodiments, a patient or a population of patients to be treated by the methods of the present disclosure have or are susceptible to endometrial cancer ("EC"). Endometrial carcinoma is the most common cancer of the female genital, tract accounting for 10-20 per 100,000 person-years. The annual number of new cases of endometrial cancer (EC) is estimated at about 325 thousand worldwide. Further, EC is the most commonly occurring cancer in post-menopausal women. About 53% of endometrial cancer cases occur in developed countries. In 2015, approximately 55,000 cases of EC were diagnosed in the U.S. and no targeted therapies are currently approved for use in EC. There is a need for agents and regimens that improve survival for advanced and recurrent EC in 1L and 2L settings. Approximately 10,170 people are predicted to die from EC in the U.S. in 2016. The most common histologic form is endometrioid adenocarcinoma, representing about 75-80% of diagnosed cases. Other histologic forms include uterine papillary serous (less than 10%), clear cell 4%, mucinous 1%, squamous less than 1% and mixed about 10%.

From the pathogenetic point of view, EC falls into two different types, so-called types I and II. Type I tumors are low-grade and estrogen-related endometrioid carcinomas (EEC) while type II are non-endometrioid (NEEC) (mainly serous and clear cell) carcinomas. The World Health Organization has recently updated the pathologic classification of EC, recognizing nine different subtypes of EC, but EEC and serous carcinoma (SC) account for the vast majority of cases. EECs are estrogen-related carcinomas, which occur in perimenopausal patients, and are preceded by precursor lesions (endometrial hyperplasia/endometrioid intraepithelial neoplasia). Microscopically, lowgrade EEC (EEC 1-2) contains tubular glands, somewhat resembling the proliferative endometrium, with architectural complexity with fusion of the glands and cribriform pattern. High-grade EEC shows solid pattern of growth. In contrast, SC occurs in postmenopausal patients in absence of hyperestrogenism. At the microscope, SC shows thick, fibrotic or edematous papillae with prominent stratification of tumor cells, cellular budding, and anaplastic cells with large, eosinophilic cytoplasms. The vast majority of EEC are low grade tumors (grades 1 and 2), and are associated with good prognosis when they are restricted to the uterus. Grade 3 EEC (EEC3) is an aggressive tumor, with increased frequency of lymph node metastasis. SCs are very aggressive, unrelated to estrogen stimulation, mainly occurring in older women. EEC 3 and SC are considered high-grade tumors. SC and EEC3 have been compared using the surveillance, epidemiology and End Results (SEER) program data from 1988 to 2001. They represented 10% and 15% of EC respectively, but accounted for 39% and 27% of cancer death respectively. Endometrial cancers can also be classified into four molecular subgroups: (1) ultramutated/POLE-mutant; (2) hypermutated MSI+ (e.g., MSI-H or MSI-L); (3) copy number low/microsatellite stable (MSS); and (4) copy number high/serous-like. Approximately 28% of cases are MSI-high. (Murali, *Lancet Oncol.* (2014). In some embodiments, a patient has a mismatch repair deficient subset of 2L endometrial cancer. In embodiments, an endometrial cancer is metastatic endometrial cancer. In embodiments, a patient has a MSS endometrial cancer. In embodiments, a patient has a MSI-H endometrial cancer.

In embodiments, a cancer is a lung cancer. In embodiments, a lung cancer is a squamous cell carcinoma of the lung. In embodiments, a lung cancer is small cell lung cancer (SCLC). In embodiments, a lung cancer is non-small cell lung cancer (NSCLC) such as squamous NSCLC. In embodiments, a lung cancer is an ALK-translocated lung cancer (e.g., ALK-translocated NSCLC). In embodiments, a cancer is NSCLC with an identified ALK translocation. In embodiments, a lung cancer is an EGFR-mutant lung cancer (e.g., EGFR-mutant NSCLC). In embodiments, a cancer is NSCLC with an identified EGFR mutation.

In embodiments, a cancer is a colorectal (CRC) cancer (e.g., a solid tumor). In embodiments, a colorectal cancer is an advanced colorectal cancer. In embodiments, a colorectal cancer is a metastatic colorectal cancer. In embodiments, a colorectal cancer is a MSI-H colorectal cancer. In embodiments, a colorectal cancer is a MSS colorectal cancer. In embodiments, a colorectal cancer is a POLE-mutant colorectal cancer. In embodiments, a colorectal cancer is a POLD-mutant colorectal cancer. In embodiments, a colorectal cancer is a high TMB colorectal cancer.

In embodiments, a cancer is a melanoma. In embodiments, a melanoma is an advanced melanoma. In embodiments, a melanoma is a metastatic melanoma. In embodiments, a melanoma is a MSI-H melanoma. In embodiments, a melanoma is a MSS melanoma. In embodiments, a melanoma is a POLE-mutant melanoma. In embodiments, a melanoma is a POLD-mutant melanoma. In embodiments, a melanoma is a high TMB melanoma.

In embodiments, a cancer is an advanced cancer.

In embodiments, a cancer is a metastatic cancer.

In embodiments, a cancer is a recurrent cancer (e.g., a recurrent gynecological cancer such as recurrent epithelial ovarian cancer, recurrent fallopian tube cancer, recurrent primary peritoneal cancer, or recurrent endometrial cancer).

Cancers that can be treated with methods described herein include cancers associated with a high tumor mutation burden (TMB), cancers that microsatellite stable (MSS), cancers that are characterized by microsatellite instability, cancers that have a high microsatellite instability status (MSI-H), cancers that have low microsatellite instability status (MSI-L), cancers associated with high TMB and MSI-H (e.g., cancers associated with high TMB and MSI-L or MSS), cancers having a defective DNA mismatch repair system, cancers having a defect in a DNA mismatch repair gene, hypermutated cancers, cancers having homologous recombination repair deficiency/homologous repair deficiency ("HRD"), cancers comprising a mutation in polymerase delta (POLD), and cancers comprising a mutation in polymerase epsilon (POLE).

In some embodiments, a tumor to be treated is characterized by microsatellite instability. In some embodiments, a tumor is characterized by microsatellite instability high status (MSI-H). Microsatellite instability ("MSI") is or comprises a change that in the DNA of certain cells (such as tumor cells) in which the number of repeats of microsatellites (short, repeated sequences of DNA) is different than the number of repeats that was contained in the DNA from which it was inherited. About 15% of sporadic colorectal cancers (CRC) harbor widespread alterations in the length of microsatellite (MS) sequences, known as microsatellite instability (MSI) (Boland and Goel, 2010). Sporadic MSI CRC tumors display unique clinicopathological features including near-diploid karyotype, higher frequency in older populations and in females, and a better prognosis (de la Chapelle and Hampel, 2010; Popat et al., 2005). MSI is also present in other tumors, such as in endometrial cancer (EC) of the uterus, the most common gynecological malignancy (Duggan et al., 1994). The same reference Bethesda panel originally developed to screen an inherited genetic disorder (Lynch syndrome) (Umar et al., 2004) is currently applied to test MSI for CRCs and ECs. However, the genes frequently targeted by MSI in CRC genomes rarely harbor DNA slippage events in EC genomes (Gurin et al., 1999).

Microsatellite instability arises from a failure to repair replication-associated errors due to a defective DNA mismatch repair (MMR) system. This failure allows persistence of mismatch mutations all over the genome, but especially in regions of repetitive DNA known as microsatellites, leading to increased mutational load. It has been demonstrated that at least some tumors characterized by MSI-H have improved responses to certain anti-PD-1 agents (Le et al., (2015) *N. Engl. J. Med.* 372(26):2509-2520; Westdorp et al., (2016) *Cancer Immunol. Immunother.* 65(10):1249-1259). In some embodiments, a cancer has a microsatellite instability of high microsatellite instability (e.g., MSI-H status). In some embodiments, a cancer has a microsatellite instability status of low microsatellite instability (e.g., MSI-Low). In some embodiments, a cancer has a microsatellite instability status of microsatellite stable (e.g., MSS status). In some embodiments microsatellite instability status is assessed by a next generation sequencing (NGS)-based assay, an immunohistochemistry (IHC)-based assay, and/or a PCR-based assay. In some embodiments, microsatellite instability is detected by NGS. In some embodiments, microsatellite instability is detected by IHC. In some embodiments, microsatellite instability is detected by PCR.

In embodiments, a patient has a MSI-L cancer.

In embodiments, a patient has a MSI-H cancer. In some embodiments, a patient has a MSI-H solid tumor. In embodiments, a MSI-H cancer is MSI-H endometrial cancer. In embodiments, a MSI-H cancer is a solid tumor. In embodiments, a MSI-H cancer is a metastatic tumor. In embodiments, a MSI-H cancer is endometrial cancer. In embodiments, a MSI-H cancer is a non-endometrial cancer. In embodiments, a MSI-H cancer is colorectal cancer.

In embodiments, a patient has a MSS cancer. In embodiments, a MSS cancer is MSS endometrial cancer.

In embodiments, a cancer is associated with a POLE (DNA polymerase epsilon) mutation (i.e., a cancer is a POLE-mutant cancer). In embodiments, a POLE mutation is a mutation in the exonuclease domain. In embodiments, a POLE mutation is a germline mutation. In embodiments, a POLE mutation is a sporadic mutation. In embodiments, a MSI cancer also is associated with a POLE mutation. In embodiments, a MSS cancer also is associated with a POLE mutation. In embodiments, a POLE mutation is identified using sequencing. In embodiments, a POLE-mutant cancer is endometrial cancer. In embodiments, a POLE-mutant cancer is colon cancer. In embodiments, a POLE-mutant cancer is pancreatic cancer, ovarian cancer, or cancer of the small intestine.

In embodiments, a cancer is associated with a POLD (DNA polymerase delta) mutation (i.e., a cancer is a POLD-mutant cancer). In embodiments, a POLD mutation is a mutation in the exonuclease domain. In embodiments, a POLD mutation is a somatic mutation. In embodiments, a POLD mutation is a germline mutation. In embodiments, a POLD-mutant cancer is identified using sequencing. In embodiments, a POLD-mutant cancer is endometrial cancer. In embodiments, a POLD-mutant cancer is colorectal cancer. In embodiments, a POLD-mutant cancer is brain cancer.

In some embodiments, a patient has a mismatch repair deficient cancer.

In embodiments, a MMRd cancer is colorectal cancer.

Microsatellite instability may arise from a failure to repair replication-associated errors due to a defective DNA mismatch repair (MMR) system. This failure allows persistence of mismatch mutations all over the genome, but especially in regions of repetitive DNA known as microsatellites, leading to increased mutational load that may improve responses to certain anti-PD-1 agents. Id. In some embodiments, MSI-H status is assessed by a NGS-based assay and/or a PCR-based MSI assay. In some embodiments, microsatellite instability is detected by next generation sequencing. In embodiments, microsatellite instability is detected using immunohistochemistry (IHC) testing.

In embodiments, a cancer (e.g., a MMRd cancer) is characterized by a high tumor mutation burden (i.e., a cancer is a high TMB cancer). In some embodiments, the cancer is associated with high TMB and MSI-H. In some embodiments, the cancer is associated with high TMB and MSI-L or MSS. In some embodiments, the cancer is endometrial cancer associated with high TMB. In some related embodiments, the endometrial cancer is associated with high TMB and MSI-H. In some related embodiments, the endometrial cancer is associated with high TMB and MSI-L or MSS. In embodiments, a high TMB cancer is colorectal cancer. In embodiments, a high TMB cancer is lung cancer (e.g., small cell lung cancer (SCLC) or non-small cell lung cancer (NSCLC) such as squamous NSCLC or non-squamous NSCLC). In embodiments, a high TMB cancer is melanoma. In embodiments, a high TMB cancer is urothelial cancer.

In embodiments, a patient has a cancer with elevated expression of tumor-infiltrating lymphocytes (TILs), i.e., a patient has a high-TIL cancer. In embodiments, a high-TIL cancer is breast cancer (e.g., triple negative breast cancer (TNBC) or HER2-positive breast cancer). In embodiments, a high-TIL cancer is a metastatic cancer (e.g., a metastatic breast cancer).

In embodiments, immune-related gene expression signatures can be predictive of a response to an anti-PD-1 therapy for cancer as described herein. For example, a gene panel that includes genes associated with IFN-γ signaling can be useful in identifying cancer patients who would benefit from anti-PD-1 therapy. Exemplary gene panels are described in Ayers et al., J. Clin. Invest., 127(8):2930-2940, 2017. In embodiments, a cancer patient has a cancer that is breast cancer (e.g., TNBC) or ovarian cancer. In embodiments, a cancer patient has a cancer that is bladder cancer, gastric cancer, bilary cancer, esophageal cancer, or head and neck squamous cell carcinoma (HNSCC). In embodiments, a cancer patient has a cancer that is anal cancer or colorectal cancer.

In some embodiments, a patient has a tumor that expresses PD-L1. In some embodiments, PD-L1 status is evaluated in a patient or patient population. In some embodiments, mutational load and baseline gene expression profiles in archival or fresh pre-treatment biopsies are evaluated before, during and/or after treatment with an anti-PD-1 antibody agent. In some embodiments, the status and/or expression of TIM-3 and/or LAG-3 are evaluated in patients.

In some embodiments, a patient has previously been treated with one or more different cancer treatment modalities. In some embodiments, at least some of the patients in the cancer patient population have previously been treated with one or more of surgery, radiotherapy, chemotherapy or immunotherapy. In some embodiments, at least some of the patients in the cancer patient population have previously been treated with chemotherapy (e.g., platinum-based chemotherapy). For example, a patient who has received two lines of cancer treatment can be identified as a 2L cancer patient (e.g., a 2L NSCLC patient). In embodiments, a patient has received two lines or more lines of cancer treatment (e.g., a 2L+ cancer patient such as a 2L+ endometrial cancer patient). In embodiments, a patient has not been previously treated with an anti-PD-1 therapy. In embodiments, a patient previously received at least one line of cancer treatment (e.g., a patient previously received at least one line or at least two lines of cancer treatment). In embodiments, a patient previously received at least one line of treatment for metastatic cancer (e.g., a patient previously received one or two lines of treatment for metastatic cancer). In embodiments, a subject is resistant to treatment with an agent that inhibits PD-1. In embodiments, a subject is refractory to treatment with an agent that inhibits PD-1. In embodiments, a method described herein sensitizes the subject to treatment with an agent that inhibits PD-1.

T Cell Immunoglobulin and Mucin Domain-3 (TIM-3)

The protein T Cell Immunoglobulin and Mucin Domain-3 (TIM-3), also known as Hepatitis A Virus Cellular Receptor 2 (HAVCR2), is a Th1-specific cell surface protein that regulates macrophage activation and enhances the severity of experimental autoimmune encephalomyelitis in mice. TIM-3 is highly expressed on the surface of multiple immune cell types, including, for example, Th1 IFN-γ+ cells, Th17 cells, natural killer (NK) cells, monocytes, and tumor-associated dendritic cells (DCs) (see, e.g., Clayton et al., J. Immunol., 192(2): 782-791 (2014); Jones et al., J. Exp. Med., 205: 2763-2779 (2008); Monney et al., Nature, 415: 536-541 (2002); Hastings et al., Eur. J. Immunol., 39: 2492-2501 (2009); Seki et al., Clin. Immunol., 127: 78-88 (2008); Ju et al., B. J. Hepatol., 52: 322-329 (2010); Anderson et al., Science, 318: 1141-1143 (2007); Baitsch et al., PLoS ONE, 7: e30852 (2012); Ndhlovu et al., Blood, 119: 3734-3743 (2012). TIM-3 also is highly expressed on "exhausted" or impaired CD8+ T-cells in a variety of chronic viral infections (e.g., HIV, HCV, and HBV) and in certain cancers (see, e.g., McMahan et al., J. Clin. Invest., 120(12): 4546-4557 (2010); Jin et al., Proc Natl Acad Sci USA, 107(33): 14733-14738 (2010); Golden-Mason et al., J. Virol., 83(18): 9122-9130 (2009); Jones et al., supra; Fourcade et al., J. Exp. Med., 207(10): 2175-2186 (2010); Sakuishi et al., J. Exp. Med., 207(10):2187-2194 (2010); Zhou et al., Blood, 117(17): 4501-4510 (2011); Ngiow et al., Cancer Res., 71(10): 3540-3551 (2011)).

Putative ligands for TIM-3 include phosphatidylserine (Nakayama et al., Blood, 113: 3821-3830 (2009)), galectin-9 (Zhu et al., Nat. Immunol., 6: 1245-1252 (2005)), high-mobility group protein 1 (HMGB1) (Chiba et al., Nature Immunology, 13: 832-842 (2012)), and carcinoembryonic antigen cell adhesion molecule 1 (CEACAM1) (Huang et al., Nature, 517(7534): 386-90 (2015)).

TIM-3 functions to regulate various aspects of the immune response. The interaction of TIM-3 and galectin-9 (Gal-9) induces cell death and in vivo blockade of this interaction exacerbates autoimmunity and abrogates tolerance in experimental models, strongly suggesting that TIM-3 is a negative regulatory molecule. In contrast to its effect on T-cells, the TIM-3-Gal-9 interaction exhibits antimicrobial effects by promoting macrophage clearance of intracellular pathogens (see, e.g., Sakuishi et al., Trends in Immunology, 32(8): 345-349 (2011)). In vivo, suppression of TIM-3 has been shown to enhance the pathological severity of experimental autoimmune encephalomyelitis (Monney et al., supra; and Anderson, A. C. and Anderson, D. E., Curr. Opin. Immunol., 18: 665-669 (2006)). Studies also suggest that dysregulation of the TIM-3-galectin-9 pathway could play a role in chronic autoimmune diseases, such as multiple sclerosis (Anderson and Anderson, supra). TIM-3 promotes clearance of apoptotic cells by binding phosphatidyl serine through its unique binding cleft (see, e.g., DeKruyff et al., J. Immunol., 184(4):1918-1930 (2010)).

Inhibition of TIM-3 activity, such as through use of monoclonal antibodies, is currently under investigation as an immunotherapy for tumors based on preclinical studies (see, e.g., Ngiow et al., Cancer Res., 71(21): 1-5 (2011); Guo et al., Journal of Translational Medicine, 11: 215 (2013); and Ngiow et al., Cancer Res., 71(21): 6567-6571 (2011)).

The present disclosure provides particular antibody agents and methods relating thereto for the treatment of cancer.

Anti-TIM-3 Antibody Agents

The present disclosure provides methods of treating cancer that include administering compositions that deliver particular anti-TIM-3 antibody agents according to regimens that may achieve clinical benefit(s). The present disclosure describes, at least in part, anti-TIM-3 antibody agents and various compositions and methods relating thereto.

In some embodiments, an anti-TIM-3 antibody agent comprises an immunoglobulin heavy chain variable domain whose amino acid sequence comprises SEQ ID NO: 1 or SEQ ID NO: 7.

```
                                      SEQ ID NO: 1
EVQLLESGGGLVQPGGSLRLSCAAASGFTFSSYDMSWVRQAPGKGLDWVS

TISGGGTYTYYQDSVKGRFTISRDNSKNTLYLQMNSLRAEDTAVYYCASM

DYWGQGTTVTVSSA
```

```
                                      SEQ ID NO: 7
EVQLLESGGGLVQPGGSLRLSCAAASGFTFSSYDMSWVRQAPGKGLDWVS

TISGGGTYTYYQDSVKGRFTISRDNSKNTLYLQMNSLRAEDTAVYYCASM

DYWGQGTTVTVSS
```

In some embodiments, an anti-TIM-3 antibody agent comprises an immunoglobulin light chain variable domain whose amino acid sequence comprises SEQ ID NO: 2 or SEQ ID NO: 8.

```
                                      SEQ ID NO: 2
DIQMTQSPSSLSASVGDRVTITCRASQSIRRYLNWYHQKPGKAPKLLIYG

ASTLQSGVPSRFSGSGSGTDFTLTISSLQPEDFAVYYCQQSHSAPLTFGG

GTKVEIKR
```

```
                                      SEQ ID NO: 8
DIQMTQSPSSLSASVGDRVTITCRASQSIRRYLNWYHQKPGKAPKLLIYG

ASTLQSGVPSRFSGSGSGTDFTLTISSLQPEDFAVYYCQQSHSAPLTFGG

GTKVEIK
```

In some embodiments, an anti-TIM-3 antibody agent comprises an immunoglobulin heavy chain variable domain whose amino acid sequence comprises SEQ ID NO: 1 or SEQ ID NO: 7 and/or an immunoglobulin light chain variable domain whose amino acid sequence comprises SEQ ID NO: 2 or SEQ ID NO: 8.

In some embodiments, an anti-TIM-3 antibody agent comprises a variable heavy chain complementarity determining region 1, 2, and/or 3 (VH-CDR) comprising the amino acid sequences GFTFSSYDMS (SEQ ID NO: 21), TISGGGTYTYYQDSVK (SEQ ID NO: 22), and/or MDY (SEQ ID NO: 23), respectively. In some embodiments an anti-TIM-3 antibody agent comprises a variable light chain complementary determining region 1, 2, and/or 3 (VL-CDR) comprising the amino acid sequences RASQSIRRYLN (SEQ ID NO: 24), GASTLQS (SEQ ID NO: 25), and/or QQSHSAPLT (SEQ ID NO: 26), respectively. In some embodiments, an anti-TIM-3 antibody comprises VH-CDR sequences of SEQ ID NOs: 21, 22, and 23, and VL-CDR sequences of SEQ ID NOs: 24, 25, and 26. See Table 1.

TABLE 1

Amino Acid Sequences of Heavy and Light Chain Complementarity Determining Regions (CDRs)

| Antibody | Variable region | CDR1 | CDR2 | CDR3 |
|---|---|---|---|---|
| Anti-TIM-3 | VH | GFTFSSYDMS (SEQ ID NO: 21) | TISGGGTYTYYQDSVK (SEQ ID NO: 22) | MDY (SEQ ID NO: 23) |
| Anti-TIM-3 | VL | RASQSIRRYLN (SEQ ID NO: 24) | GASTLQS (SEQ ID NO: 25) | QQSHSAPLT (SEQ ID NO: 26) |

In some embodiments, an anti-TIM-3 antibody agent is a monoclonal antibody. Particular antibodies of the present invention bind to TIM-3 with high affinity and effectively neutralize TIM-3 activity. Particular antibody heavy chain polypeptide (SEQ ID NO:3) and light chain polypeptide (SEQ ID NO:4) sequences are explicitly provided.

```
An anti-TIM-3 antibody heavy chain polypeptide
                                      (SEQ ID NO: 3)
EVQLLESGGGLVQPGGSLRLSCAAASGFTFSSYDMSWVRQAPGKGLDW

VSTISGGGTYTYYQDSVKGRFTISRDNSKNTLYLQMNSLRAEDTAVYYC

ASMDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK
```

-continued

An anti-TIM-3 antibody light chain polypeptide
(SEQ ID NO: 4)
DIQMTQSPSSLSASVGDRVTITCRASQSIRRYLNWYHQKPGKAPKLLIYG

ASTLQSGVPSRFSGSGSGTDFTLTISSLQPEDFAVYYCQQSHSAPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The present disclosure provides an isolated immunoglobulin heavy chain polypeptide having an amino acid sequence as set forth in SEQ ID NO:3. The present disclosure further provides an isolated immunoglobulin heavy chain polypeptide having an amino acid sequence that shares at least about 80%, 85%, 90%, 91%, 92%, 93%, 94%, 95%, 96%, 97%, 98% or 99% overall identity with that set forth in SEQ ID NO:3. In some embodiments, sequence differences relative to the sequence set forth in SEQ ID NO:3 are not within the CDRs. In some embodiments, an isolated immunoglobulin heavy chain polypeptide includes all three CDRs of SEQ ID NO:3. In some embodiments, an immunoglobulin heavy chain polypeptide includes a signal peptide. In some embodiments, an immunoglobulin heavy chain polypeptide which includes a signal peptide has an amino acid sequence as set forth in SEQ ID NO:5.

An anti-TIM-3 antibody heavy chain polypeptide
with a signal sequence
(SEQ ID NO: 5)
MEFGLSWLFLVAILKGVQCEVQLLESGGGLVQPGGSLRLSCAAASGFTFS

SYDMSWVRQAPGKGLDWVSTISGGGTYTYYQDSVKGRFTISRDNSKNTLY

LQMNSLRAEDTAVYYCASMDYWGQGTTVTVSSASTKGPSVFPLAPCSRST

SESTAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYTQ

KSLSLSLGK

In some embodiments, a provided immunoglobulin heavy chain polypeptide is or comprises an IgG4 polypeptide. In some embodiments, a provided immunoglobulin heavy chain polypeptide comprises a human IGHG4*01 polypeptide. In some embodiments, a provided immunoglobulin heavy chain polypeptide comprises one or more mutations within the IgG heavy chain region. In some embodiments, a provided immunoglobulin heavy chain polypeptide comprises an IgG4 heavy chain constant region having one or more mutations in the heavy chain constant region. In some embodiments, a provided immunoglobulin heavy chain polypeptide comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include a serine to proline stabilizing mutation that prevents half molecule exchange with other IgG4 molecules. In some embodiments, the one or more mutations in hinge region of IgG4 may include an S228P mutation. See, e.g., J. Biol. Chem. 2015; 290(9):5462-5469.

The present disclosure provides an isolated immunoglobulin light chain polypeptide having an amino acid sequence as set forth in SEQ ID NO:4. The present disclosure further provides an isolated immunoglobulin light chain polypeptide having an amino acid sequence that shares at least about 80%, 85%, 90%, 91%, 92%, 93%, 94%, 95%, 96%, 97%, 98% or 99% overall identity with that set forth in SEQ ID NO:4. In some embodiments, sequence differences relative to the sequence set forth in SEQ ID NO:4 are not within the CDRs. In some embodiments, an isolated immunoglobulin light chain polypeptide includes all three CDRs of SEQ ID NO:4. In some embodiments, a provided immunoglobulin light chain polypeptide is a kappa light chain. In some embodiments, a provided immunoglobulin light chain polypeptide comprises a human IGKC*01 polypeptide. In some embodiments, the immunoglobulin light chain polypeptide includes a signal peptide. In some embodiments, the immunoglobulin light chain polypeptide which includes a signal peptide has an amino acid sequence as set forth in SEQ ID NO:6.

An anti-TIM-3 antibody light chain polypeptide
with a signal sequence
(SEQ ID NO: 6)
MDMRVPAQLLGLLLLWLRGARCDIQMTQSPSSLSASVGDRVTITCRASQS

IRRYLNWYHQKPGKAPKLLIYGASTLQSGVPSRFSGSGSGTDFTLTISSL

QPEDFAVYYCQQSHSAPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC

In some embodiments, the present disclosure provides an anti-TIM-3 antibody agent comprising at least one immunoglobulin heavy chain having an amino acid sequence as set forth in SEQ ID NO:3 and at least one immunoglobulin light chain having an amino acid sequence as set forth in SEQ ID NO:4. In some embodiments an anti-TIM-3 antibody agent comprises two immunoglobulin heavy chains, each having an amino acid sequence as set forth in SEQ ID NO:3. Alternatively or additionally, in some embodiments an anti-TIM-3 antibody agent comprises two immunoglobulin light chains, each having an amino acid sequence as set forth in SEQ ID NO:4. In some embodiments, an anti-TIM-3 antibody agent has a canonical antibody format.

In some embodiments, a provided heavy chain, light chain and/or antibody agent is glycosylated and one or more sites. In some embodiments, a glycan is N-linked to an Fc region. In some embodiments, an antibody agent is glycosylated at Asn297 (Kabat numbering). In some embodiments, present disclosure provides a composition comprising one or more glycoforms of an heavy chain, light chain, and/or antibody agent as described herein. In some embodiments, a provided composition comprises plurality of such glycoforms, present in specified absolute and/or relative amounts. In some embodiments, the present disclosure provides compositions that may be substantially free of one or more particular glycoforms of an heavy chain, light chain, and/or antibody agent as described herein.

In embodiments, a TIM-3 binding agent is an anti-TIM-3 antibody that is TSR-022, which comprises a humanized monoclonal anti-TIM-3 antibody comprising a heavy chain whose amino acid sequence comprises SEQ ID NO: 3 and a light chain whose amino acid sequence comprises SEQ ID NO:4. This anti-TIM-3 antibody utilizes a human IGHG4*01 heavy chain gene, and a human IGKC*01 kappa light chain gene, as scaffolds. Further, there is a single Ser to Pro point mutation in the hinge region of the IgG4 heavy chain at the canonical S228 position, corresponding to residue 240 in SEQ ID NO: 5, which includes the signal sequence. Without wishing to be bound by theory, it is envisioned that this point mutation serves to stabilize the hinge of the antibody heavy chain.

Additional biophysical and biochemical characterization of this exemplary humanized monoclonal anti-TIM-3 antibody is also provided regarding observed disulfide linkages and glycosylation. Lys-C and trypsin digested peptides were well separated and detected by on-line LC-MS analysis. The disulfide bond linkages were confirmed by comparison of total ion chromatograms in the non-reduced (NR) condition with the reduced condition. Disulfide linkages are consistent with the expected disulfide linkage pattern for an IgG4 molecule. The residues involved in the expected inter- and intrachain disulfide linkages are tabulated below (Tables 2, 3, and 4).

TABLE 2

Expected residues involved in disulfide linkages of an exemplary anti-TIM-3 antibody agent heavy chain having an amino acid sequence as set forth in SEQ ID NO: 1.

| Cysteine residue ID | anti-TIM-3 mAb HC Residue (position in SEQ ID NO: 1) |
|---|---|
| I | 22 |
| II | 96 |

TABLE 2-continued

Expected residues involved in disulfide linkages of an exemplary anti-TIM-3 antibody agent heavy chain having an amino acid sequence as set forth in SEQ ID NO: 1.

| Cysteine residue ID | anti-TIM-3 mAb HC Residue (position in SEQ ID NO: 1) |
|---|---|
| III | 127 |
| IV | 140 |
| V | 196 |
| VI | 219 |
| VII | 222 |
| VIII | 254 |
| IX | 314 |
| X | 360 |
| XI | 418 |

TABLE 3

Expected residues involved in disulfide linkages of an exemplary anti-TIM-3 antibody agent light chain having an amino acid sequence as set forth in SEQ ID NO: 2.

| Cysteine residue ID | anti-TIM-3 mAb LC Residue (position in SEQ ID NO: 2) |
|---|---|
| I | 23 |
| II | 88 |
| III | 134 |
| IV | 194 |
| V | 214 |

TABLE 4

Exemplary disulfide bond assignments for an anti-TIM-3 antibody

| Disulfide bond NO. | Disulfide-containing peptides | Linkage site on HC (position in SEQ ID NO: 1) | Linkage site on LC (position in SEQ ID NO: 2) |
|---|---|---|---|
| DS1 | VTITCR=FSGSGSGTDFTLTISSLQPEDF  AVYYCQQSHSAPLTFGGGTK | | 23  88 |
| DS2 | SGTASVVCLLNNFYPR=VYACEVTHQGLS  SPVTK | | 134  194 |
| DS3 | SFNRGEC=GPSVFPLAPCSR  GEC=GPSVFPLAPCSR | 127 | 214 |
| DS4 | LSCAAASGFTFSSYDMSWVR=AEDTA  VYYCASMDYWGQGTTVTVSSASTK | 22  97 | |
| DS5 | STSESTAALGCLVK=TYTCNVDHK  STSESTAALGCLVK=TYTCNVDHKPSNTK | 140  196 | |
| DS6 | YGPPCPPCPAPEFLGGPSVFLFPPK=YGPPC PPCPAPEFLGGPSVFLFPPK  YGPPCPPCPAPEFLGGPSVFLFPPK=YGPPC PPCPAPEFLGGPSVFLFPPKPK | 219  222 | |
| DS7 | TPEVTCVVVDVSQEDPEVQFNWYVDGVE  VHNAK=CK | 254  314 | |
| DS8 | NQVSLTCLVK=WQEGNVFSCSVMHEALH  NHYTQK | 360  418 | |

LC: light chain; HC: heavy chain

This exemplary anti-TIM-3 antibody exhibits an occupied N-glycosylation site at asparagine residue 290 in the CH2 domain of each heavy chain in the mature protein sequence (SEQ ID NO:1). The expressed N-glycosylation at this site is a mixture of oligosaccharide species typically observed on IgGs expressed in mammalian cell culture, for example, shown below is the relative abundance of glycan species from a preparation of this exemplary anti-TIM-3 antibody cultured in Chinese Hamster Ovary (CHO) cells (Table 5).

TABLE 5

Glycan Analysis of an anti-TIM-3 antibody binding agent

| Species | Abundance (% of total oligosaccharide) | Description of Glycan |
| --- | --- | --- |
| G0F | 20.1% | Core fucosylated agalactobiantennary complex-type oligosaccharide |
| G1F | 41.9% | Core fucosylated monogalactosylated biantennary complex type oligosaccharide |
| G2F | 29.0% | Core-fucosylated galactosylated biantennary complex type oligosaccharide |
| G2FS1 | 3.2% | Monosialylated core fucosylated galactosylated biantennary complex type oligosaccharide |
| G2FS2 | 1.2% | Disialylated core fucosylated galactosylated biantennary complex type oligosaccharide |
| M5 | 0.4% | Oligomannosidic N-linked oligosaccharide, $Man_5GlcNAc_2$ |

PD-1-Binding Agents

The present disclosure provides methods of treating cancer that further include administering compositions that deliver particular programmed death-1 protein (PD-1)-binding agents according to regimens that may achieve clinical benefit(s). The present disclosure describes, at least in part, PD-1-binding agents (e.g., anti-PD-1 antibody agents) and various compositions and methods relating thereto. In some embodiments, a PD-1-binding agent is a monoclonal antibody.

In some embodiments, a PD-1-binding agent comprises an immunoglobulin heavy chain variable domain whose amino acid sequence comprises SEQ ID NO: 11 or SEQ ID NO: 17.

```
                                        SEQ ID NO: 11
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTVSSA

SEQ ID NO: 17
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTVSS
```

In some embodiments, a PD-1-binding agent comprises an immunoglobulin light chain variable domain whose amino acid sequence comprises SEQ ID NO: 12 or SEQ ID NO: 18.

```
                                        SEQ ID NO: 12
DIQLTQSPSFLSAYVGDRVTITCKASQDVGTAVAWYQQKPGKAPKLLIYW

ASTLHTGVPSRFSGSGSGTEFTLTISSLQPEDFATYYCQHYSSYPWTFGQ

GTKLEIKR

SEQ ID NO: 18
DIQLTQSPSFLSAYVGDRVTITCKASQDVGTAVAWYQQKPGKAPKLLIYW

ASTLHTGVPSRFSGSGSGTEFTLTISSLQPEDFATYYCQHYSSYPWTFGQ

GTKLEIK
```

In some embodiments, a PD-1-binding agent comprises an immunoglobulin heavy chain variable domain whose amino acid sequence comprises SEQ ID NO: 11 or SEQ ID NO: 17 and/or an immunoglobulin light chain variable domain whose amino acid sequence comprises SEQ ID NO: 12 or SEQ ID NO: 18. In some embodiments a PD-1-binding agent is or comprises an immunoglobulin G4 (IgG4) humanized monoclonal antibody (mAb). In some embodiments, a PD-1-binding agent comprises a human IGHG4*01 polypeptide. In some embodiments, a PD-1-binding agent comprises one or more mutations within the IgG heavy chain region. In some embodiments, a PD-1-binding agent comprises an IgG4 heavy chain constant region having one or more mutations in the heavy chain constant region. In some embodiments, a PD-1-binding agent comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include a serine to proline stabilizing mutation that prevents half molecule exchange with other IgG4 molecules. In some embodiments, the one or more mutations in hinge region of IgG4 may include an S228P mutation. See, e.g., J. Biol. Chem. 2015; 290(9):5462-5469.

In some embodiments, a PD-1-binding agent comprises an immunoglobulin heavy chain polypeptide whose amino acid sequence comprises SEQ ID NO: 13.

```
An anti-PD-1 antibody heavy chain polypeptide
(CDR sequences)
                                        SEQ ID NO: 13
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK
```

In some embodiments, a PD-1-binding agent comprises an immunoglobulin light chain polypeptide whose amino acid sequence comprises SEQ ID NO: 14.

An anti-PD-1 antibody light chain polypeptide
(CDR sequences)

SEQ ID NO: 14

DIQLTQSPSFLSAYVGDRVTITC<u>KASQDVGTAVAWY</u>QQKPGKAPKLLIY<u>W</u>

<u>ASTLHT</u>GVPSRFSGSGSGTEFTLTISSLQPEDFATYYC<u>QHYSSYPWT</u>FGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The present disclosure provides an isolated immunoglobulin heavy chain polypeptide having an amino acid sequence as set forth in SEQ ID NO:13. The present disclosure further provides an isolated immunoglobulin heavy chain polypeptide having an amino acid sequence that shares at least about 90%, 91%, 92%, 93%, 94%, 95%, 96%, 97%, 98% or 99% overall identity with that set forth in SEQ ID NO:13. In some embodiments, sequence differences relative to the sequence set forth in SEQ ID NO:13 are not within the CDRs. In some embodiments, an isolated immunoglobulin heavy chain polypeptide includes all three CDRs of SEQ ID NO:13. In some embodiments, an immunoglobulin heavy chain polypeptide includes a signal peptide. In some embodiments, an immunoglobulin heavy chain polypeptide which includes a signal peptide has an amino acid sequence as set forth in SEQ ID NO:15.

An anti-PD-1 antibody heavy chain polypeptide
with a signal sequence (SEQ ID NO: 15)

<u>MEFGLSWLFLVAILKGVQC</u>EVQLLESGGGLVQPGGSLRLSCAASGFTFSS

YDMSWVRQAPGKGLEWVSTISGGGSYTYYQDSVKGRFTISRDNSKNTLYL

QMNSLRAEDTAVYYCASPYYAMDYWGQGTTVTVSSASTKGPSVFPLAPCS

RSTSESTAALGCLVKDYFPEPVTVSWNSGALTSGVHTFPAVLQSSGLYSL

SSVVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNH

YTQKSLSLSLGK

The present disclosure provides an isolated immunoglobulin light chain polypeptide having an amino acid sequence as set forth in SEQ ID NO:14. The present disclosure further provides an isolated immunoglobulin light chain polypeptide having an amino acid sequence that shares at least about 90%, 91%, 92%, 93%, 94%, 95%, 96%, 97%, 98% or 99% overall identity with that set forth in SEQ ID NO:14. In some embodiments, sequence differences relative to the sequence set forth in SEQ ID NO:14 are not within the CDRs. In some embodiments, an isolated immunoglobulin light chain polypeptide includes all three CDRs of SEQ ID NO:14. In some embodiments, a provided immunoglobulin light chain polypeptide is a kappa light chain. In some embodiments, a provided immunoglobulin light chain polypeptide comprises a human IGKC*01 polypeptide. In some embodiments, the immunoglobulin light chain polypeptide includes a signal peptide. In some embodiments, the immunoglobulin light chain polypeptide which includes a signal peptide has an amino acid sequence as set forth in SEQ ID NO:16.

An anti-PD-1 antibody light chain polypeptide
with a signal sequence (SEQ ID NO: 16)

<u>MDMRVPAQLLGLLLLWLPGARC</u>DIQLTQSPSFLSAYVGDRVTITCKASQD

VGTAVAWYQQKPGKAPKLLIYWASTLHTGVPSRFSGSGSGTEFTLTISSL

QPEDFATYYCQHYSSYPWTFGQGTKLEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC

SEQ ID NOs: 13 and 14 describe an exemplary humanized monoclonal anti-PD-1 antibody (TSR-042) utilizing a human IGHG4*01 heavy chain gene, and a human IGKC*01 kappa light chain gene, as scaffolds. There is a single Ser to Pro point mutation in the hinge region of the IgG4 heavy chain. This mutation is at the canonical S228 position. Without wishing to be bound by theory, it is envisioned that this point mutation serves to stabilize the hinge of the antibody heavy chain.

Additional biophysical and biochemical characterization of this exemplary humanized monoclonal anti-PD-1 antibody is provided herein, which is consistent with the expected disulfide linkage pattern for an IgG4 molecule. The residues involved in the expected inter- and intrachain disulfide linkages are tabulated below (Tables 6 and 7).

TABLE 6

Expected residues involved in disulfide linkages of an exemplary anti-PD-1 antibody agent heavy chain having an amino acid sequence as set forth in SEQ ID NO: 13.

| Cysteine residue ID after Edelman[a] | anti-PD-1 mAb HC Residue (position in SEQ ID NO: 13) |
|---|---|
| I | 22 |
| II | 96 |
| III | 130 |
| IV | 143 |
| V | 199 |
| VI | 222 |
| VII | 225 |
| VIII | 257 |
| IX | 317 |
| X | 363 |
| XI | 421 |

TABLE 7

Expected residues involved in disulfide linkages of an exemplary anti-PD-1 antibody agent light chain having an amino acid sequence as set forth in SEQ ID NO: 14.

| Cysteine residue ID after Edelman[a] | anti-PD-1 mAb LC Residue (position in SEQ ID NO: 14) |
|---|---|
| I | 23 |
| II | 88 |
| III | 134 |
| IV | 194 |
| V | 214 |

This exemplary anti-PD-1 antibody exhibits an occupied N-glycosylation site at asparagine residue 293 in the CH2 domain of each heavy chain in the mature protein sequence (SEQ ID NO:13). The expressed N-glycosylation at this site is a mixture of oligosaccharide species typically observed on IgGs expressed in mammalian cell culture, for example, shown below is the relative abundance of glycan species from a preparation of this exemplary anti-PD-1 antibody cultured in Chinese Hamster Ovary (CHO) cells (Table 8).

TABLE 8

Glycan Analysis of an anti-PD-1 antibody binding agent

| Species | Abundance (% of total oligosaccharide) | Description of Glycan |
|---|---|---|
| G0 | <0.1% | Nonfucosylated agalactobiantennary complex-type oligosaccharide |
| G0F | 19.5% | Core fucosylated agalactobiantennary complex type oligosaccharide |
| G1 | 0.1% | Nonfucosylated monogalactosylated biantennary complex type oligosaccharide |
| G1F | 45.6% | Core fucosylated monogalactosylated biantennary complex type oligosaccharide |
| G2F | 27.4% | Core fucosylated galactosylated biantennary complex type oligosaccharide |
| M5 | 0.5% | Oligomannosidic N-glycan, Man$_5$GlcNAc$_2$ |

In some embodiments, the present disclosure provides an anti-PD-1 antibody agent comprising at least one immunoglobulin heavy chain having an amino acid sequence as set forth in SEQ ID NO: 13 and at least one immunoglobulin light chain having an amino acid sequence as set forth in SEQ ID NO: 14. In some embodiments an anti-PD-1 antibody agent comprises two immunoglobulin heavy chains, each having an amino acid sequence as set forth in SEQ ID NO: 13. Alternatively or additionally, in some embodiments an anti-PD-1 antibody agent comprises two immunoglobulin light chains, each having an amino acid sequence as set forth in SEQ ID NO: 14. In some embodiments, an anti-PD-1 antibody agent has a canonical antibody format.

In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin.

In some embodiments, a PD-1-binding agent is glycosylated and one or more sites. As used herein, "glycan" is a sugar polymer (moiety) component of a glycoprotein. The term "glycan" encompasses free glycans, including glycans that have been cleaved or otherwise released from a glycoprotein. In some embodiments, present disclosure provides a composition comprising one or more glycoforms of a heavy chain, light chain, and/or antibody agent as described herein. In some embodiments, a glycan is N-linked to an Fc region. In some embodiments, a PD-1-binding agent is glycosylated at Asn297 (Kabat numbering).

The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform." In some embodiments, a provided composition comprises a plurality of glycoforms of one or more of an heavy chain, light chain, and/or antibody agent as described herein.

In some embodiments, antagonist activity of a PD-1-binding agent in blocking the PD-1/PD-L1 or PD-L2 interaction may be confirmed or determined using a flow cytometry-based assay that measured binding of labeled PD-L1 and PD-L2 expressed as a mouse IgG1 Fc fusion proteins (PD-L1 mFc or PD-L2 mFc) to PD-1-expressing cells. In some embodiments, a PD-1-binding agent can efficiently block PD-1/PD-L1 and PD-1/PD-L2 binding compared to an IgG4 isotype control.

In some embodiments, a PD-1-binding agent can effectively neutralize PD-1 activity (e.g., can inhibit binding of PD-1 to PD-L1 and PD-L2). In some embodiments, functional antagonist activity of a PD-1-binding agent may be confirmed or determined in a mixed lymphocyte reaction (MLR) demonstrating enhanced interleukin (IL)-2 production upon addition of a PD-1-binding agent. In some embodiments, a MLR assay may be carried out using primary human CD4+ T cells as responders and human dendritic cells as stimulators.

Expression and Formulation

In some embodiments, an anti-TIM-3 antibody agent and/or a PD-1-binding agent is expressed from a vector comprising one or more nucleic acid sequences.

In some embodiments, anti-TIM-3 antibody agent comprises an immunoglobulin heavy chain polypeptide that is encoded by a nucleotide sequence which comprises SEQ ID NO: 9.

```
Nucleotide sequence encoding anti-TIM-3
antibody heavy chain polypeptide
                                    (SEQ ID NO: 9)
GAG GTG CAG CTG TTG GAG TCT GGG GGA GGC TTG GTA

CAG CCT GGG GGG TCC CTG AGA CTC TCC TGT GCA GCA

GCC TCT GGA TTC ACT TTC AGT AGC TAT GAC ATG TCT

TGG GTC CGC CAG GCT CCA GGG AAG GGG CTG GAC TGG

GTC TCA ACC ATT AGT GGT GGT GGT ACT TAC ACC TAC

TAT CAA GAC AGT GTG AAG GGG CGG TTC ACC ATC TCC

AGA GAC AAT TCC AAG AAC ACG CTG TAT CTG CAA ATG

AAC AGC CTG AGA GCC GAG GAC ACG GCC GTA TAT TAC

TGT GCG TCC ATG GAC TAC TGG GGG CAA GGG ACC ACG

GTC ACC GTC TCC TCA GCA TCC ACC AAG GGC CCA TCG

GTC TTC CCG CTA GCA CCC TGC TCC AGG AGC ACC TCC

GAG AGC ACA GCC GCC CTG GGC TGC CTG GTC AAG GAC

TAC TTC CCC GAA CCA GTG ACG GTG TCG TGG AAC TCA

GGC GCC CTG ACC AGC GGC GTG CAC ACC TTC CCG GCT

GTC CTA CAG TCC TCA GGA CTC TAC TCC CTC AGC AGC

GTG GTG ACC GTG CCC TCC AGC AGC TTG GGC ACG AAG

ACC TAC ACC TGC AAC GTA GAT CAC AAG CCC AGC AAC

ACC AAG GTG GAC AAG AGA GTT GAG TCC AAA TAT GGT

CCC CCA TGC CCA CCA TGC CCA GCA CCT GAG TTC CTG

GGG GGA CCA TCA GTC TTC CTG TTC CCC CCA AAA CCC

AAG GAC ACT CTC ATG ATC TCC CGG ACC CCT GAG GTC

ACG TGC GTG GTG GTG GAC GTG AGC CAG GAA GAC CCC

GAG GTC CAG TTC AAC TGG TAC GTG GAT GGC GTG GAG

GTG CAT AAT GCC AAG ACA AAG CCG CGG GAG GAG CAG

TTC AAC AGC ACG TAC CGT GTG GTC AGC GTC CTC ACC
```

-continued
```
GTC CTG CAC CAG GAC TGG CTG AAC GGC AAG GAG TAC

AAG TGC AAG GTC TCC AAC AAA GGC CTC CCG TCC TCC

ATC GAG AAA ACC ATC TCC AAA GCC AAA GGG CAG CCC

CGA GAG CCA CAG GTG TAC ACC CTG CCC CCA TCC CAG

GAG GAG ATG ACC AAG AAC CAG GTC AGC CTG ACC TGC

CTG GTC AAA GGC TTC TAC CCC AGC GAC ATC GCC GTG

GAG TGG GAG AGC AAT GGG CAG CCG GAG AAC AAC TAC

AAG ACC ACG CCT CCC GTG CTG GAC TCC GAC GGC TCC

TTC TTC CTC TAC AGC AGG CTA ACC GTG GAC AAG AGC

AGG TGG CAG GAG GGG AAT GTC TTC TCA TGC TCC GTG

ATG CAT GAG GCT CTG CAC AAC CAC TAC ACA CAG AAG

AGC CTC TCC CTG TCT CTG GGT AAA
```

In some embodiments, anti-TIM-3 antibody agent comprises an immunoglobulin light chain polypeptide that is encoded by a nucleotide sequence which comprises SEQ ID NO: 10.

```
Nucleotide sequence encoding anti-TIM-3
antibody light chain polypeptide
                                    (SEQ ID NO: 10)
GAC ATC CAG ATG ACC CAG TCT CCA TCC TCC CTG TCT

GCA TCT GTA GGA GAC AGA GTC ACC ATC ACT TGC CGG

GCA AGT CAG AGC ATT AGG AGG TAT TTA AAT TGG TAT

CAC CAG AAA CCA GGG AAA GCC CCT AAG CTC CTG ATC

TAT GGT GCA TCC ACC TTG CAA AGT GGG GTC CCA TCA

AGG TTC AGT GGT AGT GGA TCT GGG ACA GAT TTC ACT

CTC ACC ATC AGC AGT CTG CAA CCT GAA GAT TTT GCA

GTG TAT TAC TGT CAA CAG AGT CAC AGT GCC CCC CTC

ACT TTC GGC GGA GGG ACC AAG GTG GAG ATC AAA CGA

ACT GTG GCT GCA CCA TCT GTC TTC ATC TTC CCG CCA

TCT GAT GAG CAA TTG AAA TCT GGA ACT GCC TCT GTT

GTG TGC CTG CTG AAT AAC TTC TAT CCC AGA GAG GCC

AAA GTA CAG TGG AAG GTG GAT AAC GCC CTC CAA TCG

GGT AAC TCC CAG GAG AGT GTC ACA GAG CAG GAC AGC

AAG GAC AGC ACC TAC AGC CTC AGC AGC ACC CTG ACG

CTG AGC AAA GCA GAC TAC GAG AAA CAC AAA GTC TAC

GCC TGC GAA GTC ACC CAT CAG GGC CTC AGC TCG CCC

GTC ACA AAG AGC TTC AAC AGG GGA GAG TGT
```

In some embodiments, PD-1 binding agent comprises an immunoglobulin heavy chain polypeptide that is encoded by a nucleotide sequence which comprises SEQ ID NO: 19.

```
Nucleotide sequence encoding a immunoglobulin
heavy chain polypeptide of a PD-1 binding agent
                                    SEQ ID NO: 19
GAG GTG CAG CTG TTG GAG TCT GGG GGA GGC TTG GTA

CAG CCT GGG GGG TCC CTG AGA CTC TCC TGT GCA GCC

TCT GGA TTC ACT TTC AGT AGC TAT GAC ATG TCT TGG

GTC CGC CAG GCT CCA GGG AAG GGG CTG GAG TGG GTC

TCA ACC ATT AGT GGT GGT GGT AGT TAC ACC TAC TAT

CAA GAC AGT GTG AAG GGG CGG TTC ACC ATC TCC AGA

GAC AAT TCC AAG AAC ACG CTG TAT CTG CAA ATG AAC

AGC CTG AGA GCC GAG GAC ACG GCC GTA TAT TAC TGT

GCG TCC CCT TAC TAT GCT ATG GAC TAC TGG GGG CAA

GGG ACC ACG GTC ACC GTC TCC TCA GCA TCC ACC AAG

GGC CCA TCG GTC TTC CCG CTA GCA CCC TGC TCC AGG

AGC ACC TCC GAG AGC ACA GCC GCC CTG GGC TGC CTG

GTC AAG GAC TAC TTC CCC GAA CCA GTG ACG GTG TCG

TGG AAC TCA GGC GCC CTG ACC AGC GGC GTG CAC ACC

TTC CCG GCT GTC CTA CAG TCC TCA GGA CTC TAC TCC

CTC AGC AGC GTG GTG ACC GTG CCC TCC AGC AGC TTG

GGC ACG AAG ACC TAC ACC TGC AAC GTA GAT CAC AAG

CCC AGC AAC ACC AAG GTG GAC AAG AGA GTT GAG TCC

AAA TAT GGT CCC CCA TGC CCA CCA TGC CCA GCA CCT

GAG TTC CTG GGG GGA CCA TCA GTC TTC CTG TTC CCC

CCA AAA CCC AAG GAC ACT CTC ATG ATC TCC CGG ACC

CCT GAG GTC ACG TGC GTG GTG GTG GAC GTG AGC CAG

GAA GAC CCC GAG GTC CAG TTC AAC TGG TAC GTG GAT

GGC GTG GAG GTG CAT AAT GCC AAG ACA AAG CCG CGG

GAG GAG CAG TTC AAC AGC ACG TAC CGT GTG GTC AGC

GTC CTC ACC GTC CTG CAC CAG GAC TGG CTG AAC GGC

AAG GAG TAC AAG TGC AAG GTC TCC AAC AAA GGC CTC

CCG TCC TCC ATC GAG AAA ACC ATC TCC AAA GCC AAA

GGG CAG CCC CGA GAG CCA CAG GTG TAC ACC CTG CCC

CCA TCC CAG GAG GAG ATG ACC AAG AAC CAG GTC AGC

CTG ACC TGC CTG GTC AAA GGC TTC TAC CCC AGC GAC

ATC GCC GTG GAG TGG GAG AGC AAT GGG CAG CCG GAG

AAC AAC TAC AAG ACC ACG CCT CCC GTG CTG GAC TCC

GAC GGC TCC TTC TTC CTC TAC AGC AGG CTA ACC GTG

GAC AAG AGC AGG TGG CAG GAG GGG AAT GTC TTC TCA

TGC TCC GTG ATG CAT GAG GCT CTG CAC AAC CAC TAC

ACA CAG AAG AGC CTC TCC CTG TCT CTG GGT AAA
```

In some embodiments, a PD-1-binding agent comprises an immunoglobulin light chain polypeptide that is encoded by a nucleotide sequence which comprises SEQ ID NO: 20.

```
Nucleotide sequence encoding a immunoglobulin
light chain polypeptide of a PD-1 binding agent
                                       SEQ ID NO: 20
GAC ATC CAG TTG ACC CAG TCT CCA TCC TTC CTG TCT

GCA TAT GTA GGA GAC AGA GTC ACC ATC ACT TGC AAG

GCC AGT CAG GAT GTG GGT ACT GCT GTA GCC TGG TAT

CAG CAA AAA CCA GGG AAA GCC CCT AAG CTC CTG ATC

TAT TGG GCA TCC ACC CTG CAC ACT GGG GTC CCA TCA

AGG TTC AGC GGC AGT GGA TCT GGG ACA GAA TTC ACT

CTC ACA ATC AGC AGC CTG CAG CCT GAA GAT TTT GCA

ACT TAT TAC TGT CAG CAT TAT AGC AGC TAT CCG TGG

ACG TTT GGC CAG GGG ACC AAG CTG GAG ATC AAA CGG

ACT GTG GCT GCA CCA TCT GTC TTC ATC TTC CCG CCA

TCT GAT GAG CAA TTG AAA TCT GGA ACT GCC TCT GTT

GTG TGC CTG CTG AAT AAC TTC TAT CCC AGA GAG GCC

AAA GTA CAG TGG AAG GTG GAT AAC GCC CTC CAA TCG

GGT AAC TCC CAG GAG AGT GTC ACA GAG CAG GAC AGC

AAG GAC AGC ACC TAC AGC CTC AGC AGC ACC CTG ACG

CTG AGC AAA GCA GAC TAC GAG AAA CAC AAA GTC TAC

GCC TGC GAA GTC ACC CAT CAG GGC CTC AGC TCG CCC

GTC ACA AAG AGC TTC AAC AGG GGA GAG TGT
```

In some embodiments, an anti-TIM-3 antibody agent and/or a PD-1-binding agent is expressed from a vector comprising one or more nucleic acid sequences encoding an immunoglobulin heavy chain variable domain polypeptide and/or an immunoglobulin light chain variable domain polypeptide. In some embodiments, an anti-TIM-3 antibody agent and/or a PD-1-binding agent is expressed from a vector comprising one or more nucleic acid sequences encoding an immunoglobulin heavy chain polypeptide and/or an immunoglobulin light chain polypeptide. The vector can be, for example, a plasmid, episome, cosmid, viral vector (e.g., retroviral or adenoviral), or phage. Suitable vectors and methods of vector preparation are well known in the art (see, e.g., Sambrook et al., Molecular Cloning, a Laboratory Manual, 3rd edition, Cold Spring Harbor Press, Cold Spring Harbor, N.Y. (2001), and Ausubel et al, Current Protocols in Molecular Biology, Greene Publishing Associates and John Wiley & Sons, New York, N.Y. (1994)).

In some embodiments, vector(s) for expression of an anti-TIM-3 antibody agent and/or a PD-1-binding agent further comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, Gene Expression Technology: Methods in Enzymology, Vol. 185, Academic Press, San Diego, Calif. (1990).

The vector(s) comprising the nucleic acid(s) encoding an anti-TIM-3 antibody agent and/or a PD-1-binding agent of the present disclosure can be introduced into a host cell that is capable of expressing the polypeptides encoded thereby, including any suitable prokaryotic or eukaryotic cell. Some preferable qualities of host cells include easy and reliable growth, a reasonably fast growth rate, having well-characterized expression systems, and/or ease/efficient transformation or transfection.

In some embodiments, mammalian cells are utilized. A number of suitable mammalian host cells are known in the art, and many are available from the American Type Culture Collection (ATCC, Manassas, VA). Examples of suitable mammalian cells include, but are not limited to, Chinese hamster ovary cells (CHO) (ATCC No. CCL61), CHO DHFR-cells (Urlaub et al, Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70).

Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al, Proc. Natl. Acad. Sci. USA, 85: 1581-1585 (1988)), Raji cells (CCL-86), and derivatives thereof.

In some embodiments, an anti-TIM-3 antibody agent is formulated as a pharmaceutical composition, containing one or a combination of monoclonal antibodies, or antigen-binding portion(s) thereof, formulated with a pharmaceutically acceptable carrier. An anti-TIM-3 antibody agent may be formulated alone or in combination with other drugs (e.g., as an adjuvant). For example, an anti-TIM-3 antibody agent can be administered in combination with other agents for the treatment or prevention of the diseases disclosed herein (e.g., cancer).

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the ease of sterile powders is the preparation of sterile injectable solutions, the preferred methods of preparation are vacuum drying and freeze-drying (lyophilization) that yield a powder of the active ingredient plus any additional desired ingredient from a previously sterile-filtered solution thereof.

In some embodiments, a therapeutic composition is formulated as a sterile liquid. In some embodiments, the composition is free from visible particles. In some embodiments, the composition is formulated in a buffer. In some embodiments, an anti-TIM-3 antibody agent is stored at 2-8° C. In some embodiments, a drug product of the present disclosure is free of preservatives.

General Protocol

As described herein, provided methods comprise administering an anti-TIM-3 antibody agent to a patient, a subject, or a population of subjects (e.g., according to a regimen that achieves clinical benefit).

Provided methods can provide various benefits (e.g., a clinical benefit). In embodiments, a method described herein achieves a clinical benefit. In embodiments, a clinical benefit is stable disease (SD). In embodiments, a clinical benefit is a partial response (PR). IN embodiments, a clinical benefit is a complete response (CR).

In embodiments, a combination therapy achieves a clinical benefit for each therapy administered to a patient. For example, a subject may be resistant to treatment with an agent that inhibits PD-1 or a subject may be refractory to treatment with an agent that inhibits PD-1. In embodiments, a method described herein sensitizes the subject to treatment with an agent that inhibits PD-1. Therefore, in embodiments, a benefit of a combination therapy comprising administration of a TIM-3 inhibitor (e.g., any anti-TIM-3 antibody described herein) and a PD-1 inhibitor (e.g., any anti-PD-1 antibody described herein) is to achieve a clinical benefit with a PD-1 inhibitor (e.g., any anti-PD-1 antibody described herein) or to improve a clinical benefit.

In embodiments, a patient or subject is an animal. In embodiments, a patient or subject is a human.

In embodiments, administration of an anti-TIM-3 antibody agent is parenteral administration. In embodiments, parenteral administration is intravenous administration. In embodiments, intravenous administration is intravenous infusion.

In some embodiments, the regimen comprises at least one parenteral dose of an anti-TIM-3 antibody agent. In some embodiments, the regimen comprises a plurality of parenteral doses.

In some embodiments, the parenteral dose is an amount of an anti-TIM-3 antibody agent is within a range of about 5 to about 5000 mg (e.g., about 5 mg, about 10 mg, about 50 mg, about 100 mg, about 500 mg, about 600 mg, about 700 mg, about 800 mg, about 900 mg, about 1000 mg, about 1100 mg, about 1200 mg, about 1300 mg, about 1400 mg, about 1500 mg, about 2000 mg, about 3000 mg, about 4000 mg, about 5000 mg, or a range defined by any two of the foregoing values). In some embodiments, the parenteral dose of an anti-TIM-3 antibody agent is 500 mg or 1000 mg. In some embodiments, the parenteral dose of an anti-TIM-3 antibody agent is about 100 mg, about 300 mg, or about 1200 mg.

In some embodiments, the dose is in an amount relative to body weight. In some embodiments, the parenteral dose of an anti-TIM-3 antibody agent is within a range of about 0.01 mg/kg to 100 mg/kg of animal or human body weight; however, doses below or above this exemplary range are within the scope of the invention. The dose (e.g., a daily parenteral dose) can be about 0.01 mg/kg to about 50 mg/kg of total body weight (e.g., about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 12 mg/kg, about 15 mg/kg, about 20 mg/kg, or a range defined by any two of the foregoing values).

In some embodiments, a composition that delivers an anti-TIM-3 antibody agent is administered to a patient at a dose of 0.1, 1, 3 or 10 mg/kg. In some embodiments, the composition that delivers an anti-TIM-3 antibody agent is administered according to a regimen that includes a dose of 0.1, 1, 3 or 10 mg/kg every two weeks. In some embodiments, the composition that delivers an anti-TIM-3 antibody agent is administered according to a regimen that includes a dose of 0.1, 1, 3 or 10 mg/kg every three weeks. In some embodiments, the composition that delivers an anti-TIM-3 antibody agent is administered according to a regimen that includes a dose of 0.1, 1, 3 or 10 mg/kg every four weeks.

In some embodiments, a composition that delivers an anti-TIM-3 antibody agent is administered to a patient at a dose of about 100 to about 500 mg (e.g., 200 to 500 mg). In some embodiments, the composition that delivers an anti-TIM-3 antibody agent is administered according to a regimen that includes a dose of about 100 to about 500 mg (e.g., 200 mg, 300 mg, 400 mg, 500 mg) every two weeks. In some embodiments, the composition that delivers an anti-TIM-3 antibody agent is administered according to a regimen that includes a dose of about 100 to about 500 mg (e.g., 200 mg, 300 mg, 400 mg, 500 mg) every three weeks. In some embodiments, the composition that delivers an anti-TIM-3 antibody agent is administered according to a regimen that includes a dose of about 100 to about 500 mg (e.g., 200 mg, 300 mg, 400 mg, 500 mg) mg every four weeks.

In some embodiments, a composition that delivers an anti-TIM-3 antibody agent is administered to a patient at a dose of about 800 to about 1500 mg (e.g., 800 mg, 900 mg, 1000 mg, 1100 mg, 1200 mg, 1300 mg, 1400 mg, 1500 mg). In some embodiments, the composition that delivers an anti-TIM-3 antibody agent is administered according to a regimen that includes a dose of about 800 to about 1500 mg (e.g., 800 mg, 900 mg, 1000 mg, 1100 mg, 1200 mg, 1300 mg, 1400 mg, 1500 mg) mg every four weeks. In some embodiments, the composition that delivers an anti-TIM-3 antibody agent is administered according to a regimen that includes a dose of about 800 to about 1500 mg (e.g., 800 mg, 900 mg, 1000 mg, 1100 mg, 1200 mg, 1300 mg, 1400 mg, 1500 mg) every six weeks. In some embodiments, the composition that delivers an anti-TIM-3 antibody agent is administered according to a regimen that includes a dose of about 800 to about 1500 mg (e.g., 800 mg, 900 mg, 1000 mg, 1100 mg, 1200 mg, 1300 mg, 1400 mg, 1500 mg) every eight weeks.

In embodiments, a dose (e e.g., a therapeutically effective dose, a dose administered by a composition that delivers an anti-TIM-3 antibody agent, or a parenteral dose) is about 1 mg/kg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, an anti-TIM-3 antibody agent is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In embodiments, a dose (e e.g., a therapeutically effective dose, a dose administered by a composition that delivers an anti-TIM-3 antibody agent, or a parenteral dose) is about 3 mg/kg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In embodiments, a dose (e e.g., a therapeutically effective dose, a dose administered by a composition that delivers an anti-TIM-3 antibody agent, or a parenteral dose) is about 10 mg/kg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In embodiments, a dose (e.g., a therapeutically effective dose, a dose administered by a composition that delivers an anti-TIM-3 antibody agent, or a parenteral dose) is about 100-1500 mg of a TIM-3 inhibitor (e.g., an anti-TIM-3 antibody agent). In embodiments, administration of a dose (e.g., intravenous administration such as intravenous infusion) is once every week (Q1W). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In embodiments, a dose (e e.g., a therapeutically effective dose, a dose administered by a composition that delivers an anti-TIM-3 antibody agent, or a parenteral dose) is about 100 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 200 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 300 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 400 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 500 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 600 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 700 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 800 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 900 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1000 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1100 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1200 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1300 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1400 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

In any of the methods described herein, a dose (e.g., a therapeutically effective dose, a dose administered by a composition that delivers an anti-TIM-3 antibody agent, or a parenteral dose) is about 1500 mg of a TIM-3 inhibitor (e.g., an anti-TIM-3 antibody agent). In embodiments, administration of a dose (e.g., intravenous administration such as intravenous infusion) is once every two weeks (Q2W). In embodiments, administration of a dose (e.g., intravenous administration such as intravenous infusion) is once every three weeks (Q3W). In embodiments, administration of a dose (e.g., intravenous administration such as intravenous infusion) is once every four weeks (Q4W). In embodiments, administration of a dose (e.g., intravenous administration such as intravenous infusion) is once every five weeks (Q5W). In embodiments, administration of a dose (e.g., intravenous administration such as intravenous infusion) is once every six weeks (Q6W). In embodiments, administration of a TIM-3 inhibitor (e.g., an anti-TIM-3 antibody agent) is intravenous. In embodiments, administration of a TIM-3 inhibitor (e.g., an anti-TIM-3 antibody agent) is intravenous infusion. In embodiments, administration of a TIM-3 inhibitor (e.g., an anti-TIM-3 antibody agent) is for monotherapy. In embodiments, administration of a TIM-3 inhibitor (e.g., an anti-TIM-3 antibody agent) is for combination therapy (e.g., in combination with an immune checkpoint inhibitor (e.g., an anti-PD-1 antibody such as TSR-042). In embodiments, a TIM-3 inhibitor is an anti-TIM-3 antibody agent. In embodiments, a TIM-3 inhibitor is TSR-022. In embodiments, an anti-TIM-3 antibody agent comprises an immunoglobulin heavy chain comprising an amino acid sequence having at least about 90%, 91%, 92%, 93%, 94%, 95%, 96%, 97%, 98% or 99% overall identity with SEQ ID NO:3 and an immunoglobulin light chain comprising an amino acid sequence having at least about 90%, 91%, 92%, 93%, 94%, 95%, 96%, 97%, 98% or 99% overall identity with SEQ ID NO:4.

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

In some embodiments, an anti-TIM-3 antibody agent is administered to a patient or population of subjects who has exhibited response to prior therapy. In some embodiments, the patient or population of subjects has exhibited response to a prior cancer therapy.

In some embodiments, an anti-TIM-3 antibody agent is administered to a patient or population of subjects who has not exhibited response to prior therapy. In some embodiments, the patient or population of subjects has not received or exhibited response to a prior cancer therapy.

In embodiments, a subject is resistant to treatment with an agent that inhibits PD-1. In embodiments, a subject is refractory to treatment with an agent that inhibits PD-1. In embodiments, a method described herein sensitizes the subject to treatment with an agent that inhibits PD-1.

In embodiments, an anti-TIM-3 antibody agent as described herein is administered in combination with one or more additional therapies (e.g., therapies as described herein). That is, a subject is treated with an anti-TIM-3 antibody agent and one or more additional therapies is administered to a subject such that the subject receives each therapy.

In embodiments, an additional therapy is surgery. In embodiments, an additional therapy is radiotherapy. In embodiments, an additional therapy is chemotherapy. In embodiments, an additional therapy is immunotherapy.

In some embodiments, an anti-TIM-3 antibody agent is administered as a monotherapy.

In some embodiments, an anti-TIM-3 antibody agent is administered in combination therapy. In embodiments, an anti-TIM-3 antibody agent is administered in combination with another treatment modality (e.g., with one or more of surgery, radiotherapy, chemotherapy, or immunotherapy). In embodiments, an anti-TIM-3 antibody agent is administered in combination with surgery. In embodiments, an anti-TIM-3 antibody agent is administered in combination with radiotherapy. In embodiments, an anti-TIM-3 antibody agent is administered in combination with chemotherapy. In embodiments, an anti-TIM-3 antibody agent is administered in combination with immunotherapy.

In some embodiments, an anti-TIM-3 antibody agent is administered simultaneously or sequentially with an additional therapeutic agent, such as, for example, another antibody agent (e.g., an antibody agent that binds to PD-1) and/or a chemotherapeutic agent (e.g., niraparib). In some embodiments, an anti-TIM-3 antibody agent is administered before, during, or after administration of an additional therapeutic agent. In some embodiments, an anti-TIM-3 antibody agent is administered before, during, or after administration of a chemotherapeutic agent (e.g., niraparib).

An anti-TIM-3 antibody agent may be administered alone or in combination with other drugs (e.g., as an adjuvant). For example, the anti-TIM-3 antibody agent can be administered in combination with other agents for the treatment or prevention of the diseases disclosed herein (e.g., cancer). In this respect, the anti-TIM-3 antibody agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery.

Administration of an anti-TIM-3 antibody agent simultaneously or sequentially with an additional therapeutic agent is referred to herein as "combination therapy." In combination therapy, an anti-TIM-3 antibody agent can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional therapeutic agent to a subject in need thereof. In some embodiments an anti-TIM-3 antibody agent and an additional therapeutic agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

PARP Inhibitors

In embodiments, an additional therapy is a poly (ADP-ribose) polymerase (PARP) inhibitor.

In embodiments, a PARP inhibitor inhibits PARP-1 and/or PARP-2. In some embodiments, the agent is a small molecule, a nucleic acid, a polypeptide (e.g., an antibody), a carbohydrate, a lipid, a metal, or a toxin. In related embodiments, the agent is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, simmiparib, talazoparib (BMN-673), veliparib (ABT-888), WW 46, 2-(4-(trifluoromethyl)phenyl)-7,8-dihydro-5H-thiopyrano[4,3-d]pyrimidin-4-ol, and salts or derivatives thereof. In some related embodiments, an agent is niraparib, olaparib, rucaparib, talazoparib, veliparib, or salts or derivatives thereof. In certain embodiments, an agent is niraparib or a salt or derivative thereof. In certain embodiments, an agent is olaparib or a salt or derivative thereof. In certain embodiments, an agent is rucaparib or a salt or derivative thereof. In certain embodiments, an agent is talazoparib or a salt or derivative thereof. In certain embodiments, an agent is veliparib or a salt or derivative thereof.

Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. See WO 2008/084261 (published on Jul. 17, 2008), WO 2009/087381 (published Jul. 16, 2009), and PCT/US17/40039 (filed Jun. 29, 2017), the entirety of each of which is hereby incorporated by reference. Niraparib can be prepared according to Scheme 1 of WO 2008/084261.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate. The molecular structure of the tosylate monohydrate salt of niraparib is shown below:

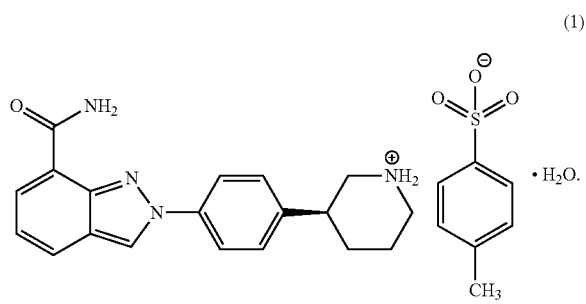

(1)

Niraparib is a potent and selective PARP-1 and PARP-2 inhibitor with inhibitory concentration at 50% of control ($IC_{50}$)=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control ($IC_{90}$) of about 4 and 50 nM, respectively.

In embodiments, niraparib is administered at a dose equivalent to about 100 mg of niraparib free base (e.g., a pharmaceutically acceptable salt of niraparib such as niraparib tosylate monohydrate is administered at a dose equivalent to about 100 mg of niraparib free base). In embodiments, niraparib is administered at a dose equivalent to about 200 mg of niraparib free base (e.g., a pharmaceutically acceptable salt of niraparib such as niraparib tosylate monohydrate is administered at a dose equivalent to about 200 mg of niraparib free base In embodiments, niraparib is administered at a dose equivalent to about 300 mg of niraparib free base (e.g., a pharmaceutically acceptable salt of niraparib such as niraparib tosylate monohydrate is administered at a dose equivalent to about 300 mg of niraparib free base).

Checkpoint Inhibitors

In embodiments, an additional therapy is an immunotherapy. In embodiments, an immunotherapy comprises administration of one or more further immune checkpoint inhibitors (e.g., administration of one, two, three, four, or more further immune checkpoint inhibitors).

Exemplary immune checkpoint targets for inhibition include: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, IDO, and CSF1R. Accordingly, agents that inhibit of any of these molecules can be used in combination with an anti-TIM-3 therapy described herein.

In embodiments, an immune checkpoint inhibitor is an agent that inhibits PD-1, CTLA-4, LAG-3, TIGIT, IDO, or CSF1R.

In embodiments, an immune checkpoint inhibitor is a PD-1 inhibitor. In embodiments, a PD-1 inhibitor is a PD-1 binding agent (e.g., an antibody, an antibody conjugate, or an antigen-binding fragment thereof). In embodiments, a PD-1 inhibitor is a PD-L1 or PD-L2 binding agent (e.g., an antibody, an antibody conjugate, or an antigen-binding fragment thereof). In embodiments, a PD-1 inhibitor is nivolumab, pembrolizumab, atezolizumab, durvalumab, avelumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZM009, KN-035, AB122, genolimzumab (CBT-501), FAZ-053, CK-301, AK 104, or GLS-010, or any of the PD-1 antibodies disclosed in WO2014/179664. In embodiments, a PD-1 inhibitor is TSR-042. In some embodiments, a PD-1-inhibitor (e.g., TSR-042) is administered according to a regimen that comprises administering an about 500 mg dose every 3 weeks for four doses followed by administering at least one about 1,000 mg dose every six weeks after the fourth dose of about 500 mg. In some embodiments, additional about 1,000 mg doses are administered every six weeks after the first about 1000 mg dose until no further clinical benefit is achieved. In some particular embodiments, a PD-1-inhibitor (e.g., TSR-042) is administered according to a dosing regimen that includes 500 mg for 4 cycles Q3W followed by 1000 mg Q6W.

In embodiments, an immune checkpoint inhibitor is a CTLA-4 inhibitor (e.g., an antibody, an antibody conjugate, or an antigen-binding fragment thereof). In embodiments, a CTLA-4 inhibitor is a small molecule, a nucleic acid, a polypeptide (e.g., an antibody), a carbohydrate, a lipid, a metal, or a toxin. In embodiments, a CTLA-4 inhibitor is a small molecule. In embodiments, a CTLA-4 inhibitor is a CTLA-4 binding agent. In embodiments, a CTLA-4 inhibitor is an antibody, an antibody conjugate, or an antigen-binding fragment thereof. In embodiments, a CTLA-4 inhibitor is ipilimumab (Yervoy), AGEN1884, or tremelimumab.

In embodiments, an immune checkpoint inhibitor is a LAG-3 inhibitor (e.g., an antibody, an antibody conjugate, or an antigen-binding fragment thereof). In embodiments, a LAG-3 inhibitor is a small molecule, a nucleic acid, a polypeptide (e.g., an antibody), a carbohydrate, a lipid, a metal, or a toxin. In embodiments, a LAG-3 inhibitor is a small molecule. In embodiments, a LAG-3 inhibitor is a LAG-3 binding agent. In embodiments, a LAG-3 inhibitor is an antibody, an antibody conjugate, or an antigen-binding fragment thereof. In embodiments, a LAG-3 inhibitor is a IMP321, BMS-986016, GSK2831781, Novartis LAG525, or a LAG-3 inhibitor described in WO 2016/126858, WO 2017/019894, or WO 2015/138920, each of which is hereby incorporated by reference in its entirety.

In embodiments, an immune checkpoint inhibitor is a TIGIT inhibitor (e.g., an antibody, an antibody conjugate, or an antigen-binding fragment thereof). In embodiments, a TIGIT inhibitor is a small molecule, a nucleic acid, a polypeptide (e.g., an antibody), a carbohydrate, a lipid, a metal, or a toxin. In embodiments, a TIGIT inhibitor is small molecule. In embodiments, a TIGIT inhibitor is a TIGIT binding agent. In embodiments, a TIGIT inhibitor is an antibody, an antibody conjugate, or an antigen-binding fragment thereof. In embodiments, a TIGIT inhibitor is MTIG7192A, BMS-986207, or OMP-31M32.

In embodiments, an immune checkpoint inhibitor is an IDO inhibitor. In embodiments, an IDO inhibitor is a small molecule, a nucleic acid, a polypeptide (e.g., an antibody), a carbohydrate, a lipid, a metal, or a toxin. In embodiments, an IDO inhibitor is small molecule. In embodiments, an IDO inhibitor is an IDO binding agent. In embodiments, an IDO inhibitor is an antibody, an antibody conjugate, or an antigen-binding fragment thereof.

In embodiments, an immune checkpoint inhibitor is a CSF1R inhibitor. In embodiments, a CSF1R inhibitor is a small molecule, a nucleic acid, a polypeptide (e.g., an antibody), a carbohydrate, a lipid, a metal, or a toxin. In embodiments, a CSF1R inhibitor is small molecule. In embodiments, a CSF1R inhibitor is a CSF1R binding agent. In embodiments, a CSF1R inhibitor is an antibody, an antibody conjugate, or an antigen-binding fragment thereof.

In embodiments, a method comprises administering a TIM-3 inhibitor with at least two of the immune checkpoint inhibitors. In embodiments, a method comprises administering a third checkpoint inhibitor. In embodiments, a method comprises administering a TIM-3 inhibitor with a PD-1 inhibitor, and a LAG-3 inhibitor, such that the subject receives all three. In embodiments, a method comprises administering a TIM-3 inhibitor with a PD-1 inhibitor, a LAG-3 inhibitor, and a CTLA-4 inhibitor, such that the subject receives all four.

In embodiments, a subject has been further administered or will be administered an agent that inhibits poly (ADP-ribose) polymerase (PARP), such that the subject receives treatment with a TIM-3 inhibitor and a PARP inhibitor.

In embodiments, a subject is further administered or will be administered one or more immune checkpoint inhibitors (e.g., a PD-1 inhibitor and/or a LAG-3 inhibitor) such that the subject receives treatment with a TIM-3 inhibitor, a PARP inhibitor (e.g., niraparib), and the one or more immune checkpoint inhibitors. In embodiments, a subject is administered a TIM-3 inhibitor, a PD-1 inhibitor (e.g., TSR-042) and a PARP inhibitor (e.g., niraparib). In embodiments, a subject is administered a TIM-3 inhibitor, a PD-1 inhibitor (e.g., TSR-042), a LAG-3 inhibitor, and a PARP inhibitor (e.g., niraparib).

For female patients of childbearing potential, it is preferable that the patient have a negative serum pregnancy test within 72 hours prior to the date of administration of the first dose of an anti-TIM-3 antibody agent. It is also preferable that female patients of childbearing potential and male patients agree to use 2 adequate methods of contraception with their partner. In some embodiments, a patient agrees to use 2 methods of contraception starting with the screening visit through 150 days after the last dose of study therapy.

The present disclosure provides, in some embodiments, methods of treating cancer in a patient in need thereof, the method comprising administering a one or more compositions that deliver an anti-TIM-3 antibody agent in combination with a PD-1 inhibitor (e.g., a PD-1-binding agent such as an anti-PD-1 antibody). FIG. 1 provides an exemplary schematic of the combination of anti-TIM-3 and anti-PD-1 antibodies in order to enhance anti-tumor efficiency. In some embodiments, a patient or patient population is receiving a combination therapy that comprises administration of an anti-TIM-3 antibody agent and a PD-1-binding agent. In some embodiments, the PD-1 binding agent is nivolumab or pembrolizumab. In embodiments, a PD-1 inhibitor is a PD-1 binding agent (e.g., an antibody, an antibody conjugate, or an antigen-binding fragment thereof). In embodiments, a PD-1 binding agent is nivolumab, pembrolizumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, AMP-514/MEDI-0680, AGEN-2034, CS1001, TSR-042, Sym-021, PF-06801591, LZM009, KN-035, AB122, genolimzumab (CBT-501), AK 104, or GLS-010, or derivatives thereof. In embodiments, a PD-1 inhibitor is a PD-L1 or PD-L2 binding agent (e.g., an antibody, an antibody conjugate, or an antigen-binding fragment thereof). In embodiments, a PD-1 inhibitor is a PD-L1 or PD-L2 binding agent is durvalumab, atezolizumab, avelumab, BGB-A333, SHR-1316, FAZ-053, CK-301, or, PD-L1 millamolecule, or derivatives thereof.

In some embodiments, a patient or patient population is receiving a combination therapy that comprises administration of an anti-TIM-3 antibody agent comprising an immunoglobulin heavy chain variable domain whose amino acid sequence comprises SEQ ID NO: 1 or SEQ ID NO: 7 and an immunoglobulin light chain variable domain whose amino acid sequence comprises SEQ ID NO: 2 or SEQ ID NO: 8. In some embodiments, an anti-TIM-3 antibody agent comprises an immunoglobulin heavy chain whose amino acid sequence comprises SEQ ID NO: 3 and an immunoglobulin light chain whose amino acid sequence comprises SEQ ID NO: 4.

In some embodiments, a patient or patient population is receiving a combination therapy that comprises administration of a PD-1-binding agent comprising an immunoglobulin heavy chain variable domain whose amino acid sequence comprises SEQ ID NO: 11 or SEQ ID NO: 17 and an immunoglobulin light chain variable domain whose amino acid sequence comprises SEQ ID NO: 12 or SEQ ID NO: 18. In some embodiments comprising combinations, the PD-1-binding agent comprises an immunoglobulin heavy chain whose amino acid sequence comprises SEQ ID NO: 13 and an immunoglobulin light chain whose amino acid sequence comprises SEQ ID NO: 14.

In some embodiments, an anti-TIM-3 antibody agent (e.g., an anti-TIM-3 antibody) is administered at a dose of 0.1, 1, 3 or 10 mg/kg. In some embodiments, an anti-TIM-3 antibody agent is administered according to a regimen that includes a dose of 0.1, 1, 3 or 10 mg/kg every two weeks. In some embodiments, an anti-TIM-3 antibody agent is administered according to a regimen that includes a dose of 1, 3 or 10 mg/kg every three weeks.

In some embodiments, an anti-TIM-3 antibody agent is administered according to a regimen that includes a dose of 1, 3 or 10 mg/kg every four weeks. In some embodiments, an anti-TIM-3 antibody agent at a fixed dose within a range of 200 mg to 1,500 mg. In some embodiments, an anti-TIM-3 antibody agent at a fixed dose within a range of 300 mg to 1,000 mg. In some embodiments, an anti-TIM-3 antibody agent is administered according to a regimen that includes a fixed dose every two weeks. In some embodiments, an anti-TIM-3 antibody agent is administered according to a regimen that includes a fixed dose every three weeks. In some embodiments, an anti-TIM-3 antibody agent is administered according to a regimen that includes a fixed dose every four weeks.

In some embodiments, a PD-1-binding agent (e.g., an anti-PD-1 antibody such as TSR-042) is administered at a dose of about 1, 3 or 10 mg/kg. In some embodiments, a PD-1-binding agent (e.g., an anti-PD-1 antibody such as TSR-042) is administered according to a regimen that includes a dose of about 1, 3 or 10 mg/kg every two weeks. In some embodiments, a PD-1-binding agent (e.g., an anti-PD-1 antibody such as TSR-042) is administered according to a regimen that includes a dose of about 1, 3 or 10 mg/kg every three weeks. In some embodiments, a PD-1-binding agent (e.g., an anti-PD-1 antibody) is administered according to a regimen that includes a dose of about 1, 3 or 10 mg/kg every four weeks. In some embodiments, a PD-1-binding agent (e.g., an anti-PD-1 antibody such as TSR-042) at a dose of about 500 mg. In some embodiments, a PD-1-binding agent (e.g., an anti-PD-1 antibody such as TSR-042) is administered according to a regimen that includes a dose of about 500 mg every two weeks. In some embodiments, a PD-1-binding agent (e.g., an anti-PD-1 antibody such as TSR-042) is administered according to a regimen that includes a dose of about 500 mg every three weeks. In some embodiments, a PD-1-binding agent (e.g., an anti-PD-1 antibody such as TSR-042) is administered according to a regimen that includes a dose of about 500 mg every four weeks. In some embodiments, a PD-1-binding agent (e.g., an anti-PD-1 antibody such as TSR-042) is administered according to a regimen that includes a dose of about 1000 mg every six weeks. In some embodiments, a PD-1-binding agent (e.g., an anti-PD-1 antibody such as TSR-042) is administered according to a regimen that includes a first dose of about 500 mg every three weeks (Q3W) for the first 2-6 (e.g., the first 2, 3, 4, 5, or 6) dosage cycles and a second dose of about 1000 mg every six weeks (Q6W) until treatment is discontinued (e.g., due to disease progression, adverse effects, or as determined by a physician). In some embodiments, a PD-1-binding agent (e.g., an anti-PD-1 antibody such as TSR-042) is administered according to a regimen that includes a first dose of about 500 mg every three weeks (Q3W) for the first four dosage cycles and a second dose of about 1000 mg every six weeks (Q6W) until treatment is discontinued (e.g., due to disease progression, adverse effects, or as determined by a physician). In embodiments, a PD-1 binding agent is an anti-PD-1 antibody. In embodiments, a PD-1 binding agent is TSR-042.

In certain methods, an anti-TIM-3 antibody agent can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a PD-1-binding agent to a subject in need thereof.

Measuring Tumor Response

In some embodiments, a clinical benefit is a complete response ("CR"), a partial response ("PR") or a stable disease ("SD"). In some embodiments, a clinical benefit corresponds to at least SD. In some embodiments, a clinical benefit corresponds to at least a PR. In some embodiments, a clinical benefit corresponds to a CR. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, at least 5% of patients achieve a clinical benefit. In some embodiments, at least 5% of patients achieve SD. In some embodiments, at least 5% of patients achieve at least a PR. In some embodiments, at least 5% of patients achieve CR. In some embodiments, at least 20% of patients achieve a clinical benefit. In some embodiments, at least 20% of patients achieve SD.

In some embodiments, the clinical benefit (e.g., SD, PR and/or CR) is determined in accordance with Response Evaluation Criteria in Solid Tumors (RECIST). In some embodiments, the clinical benefit (e.g., SD, PR and/or CR) is determined in accordance RECIST guidelines.

In some embodiments, tumor response can be measured by, for example, the RECIST v 1.1 guidelines. The guidelines are provided by E. A. Eisenhauer, et al., "New response evaluation criteria in solid tumors: Revised RECIST guideline (version 1.1)," *Eur. J. of Cancer*, 45: 228-247 (2009), which is incorporated by reference in its entirety. The guidelines require, first, estimation of the overall tumor burden at baseline, which is used as a comparator for subsequent measurements. Tumors can be measured via use of any imaging system known in the art, for example, by a CT scan, or an X-ray. Measurable disease is defined by the presence of at least one measurable lesion. In studies where the primary endpoint is tumor progression (either time to progression or proportion with progression at a fixed date), the protocol must specify if entry is restricted to those with measurable disease or whether patients having non-measurable disease only are also eligible.

When more than one measurable lesion is present at baseline, all lesions up to a maximum of five lesions total (and a maximum of two lesions per organ) representative of all involved organs should be identified as target lesions and will be recorded and measured at baseline (this means in instances where patients have only one or two organ sites involved a maximum of two and four lesions respectively will be recorded).

Target lesions should be selected on the basis of their size (lesions with the longest diameter), be representative of all involved organs, but in addition should be those that lend themselves to reproducible repeated measurements.

Lymph nodes merit special mention since they are normal anatomical structures which may be visible by imaging even if not involved by tumor. Pathological nodes which are defined as measurable and may be identified as target lesions must meet the criterion of a short axis of P15 mm by CT scan. Only the short axis of these nodes will contribute to the baseline sum. The short axis of the node is the diameter normally used by radiologists to judge if a node is involved by solid tumour. Nodal size is normally reported as two dimensions in the plane in which the image is obtained (for CT scan this is almost always the axial plane; for MRI the plane of acquisition may be axial, saggital or coronal). The smaller of these measures is the short axis.

For example, an abdominal node which is reported as being 20 mm·30 mm has a short axis of 20 mm and qualifies as a malignant, measurable node. In this example, 20 mm should be recorded as the node measurement. All other pathological nodes (those with short axis P10 mm but <15 mm) should be considered non-target lesions. Nodes that have a short axis <10 mm are considered non-pathological and should not be recorded or followed.

A sum of the diameters (longest for non-nodal lesions, short axis for nodal lesions) for all target lesions will be calculated and reported as the baseline sum diameters. If lymph nodes are to be included in the sum, then as noted above, only the short axis is added into the sum. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent', or in rare cases 'unequivocal progression.' In addition, it is possible to record multiple nontarget lesions involving the same organ as a single item on the case record form (e.g., 'multiple enlarged pelvic lymph nodes' or 'multiple liver metastases').

In some embodiments, tumor response can be measured by, for example, the immune-related RECIST (irRECIST) guidelines, which include immune related Response Criteria (irRC). In irRC, measurable lesions are measured that have at least one dimension with a minimum size of 10 mm (in the longest diameter by CT or MRI scan) for nonnodal lesions and greater than or equal to 15 mm for nodal lesions, or at least 20 mm by chest X-ray.

In some embodiments, Immune Related Response Criteria include CR (complete disappearance of all lesions (measurable or not, and no new lesions)); PR (decrease in tumor burden by 50% or more relative to baseline); SD (not meeting criteria for CR or PR in the absence of PD); or PD (an increase in tumor burden of at 25% or more relative to nadir). Detailed description of irRECIST can be found at Bohnsack et al., (2014) ESMO, ABSTRACT 4958 and Nishino et al., (2013) Clin. Cancer Res. 19(14): 3936-43.

In some embodiments, tumor response can be assessed by either irRECIST or RECIST version 1.1. In some embodiments, tumor response can be assessed by both irRECIST and RECIST version 1.1.

Pharmacokinetics

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, a patient population includes one or more subjects ("a population of subjects") suffering from metastatic disease.

In some embodiments, a patient population includes one or more subjects that is suffering from or susceptible to cancer. In some such embodiments, the cancer is non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer. In embodiments, a cancer is a solid tumor (e.g., an advanced solid tumor, a metastatic solid tumor, a MSS solid tumor, a MSI-H solid tumor, or a POLE mutant solid tumor). In embodiments, a cancer is a melanoma (e.g., an advanced melanoma, a metastatic melanoma, a MSS melanoma, a MSI-H melanoma, or a POLE mutant melanoma). In embodiments, a cancer is a lung cancer such as NSCLC (e.g., advanced NSCLC, metastatic NSCLC, MSI-H NSCLC, MSS NSCLC, POLE mutant NSCLC, EGFR-mutant NSCLC, or ALK-translocated NSCLC). In embodiments, a cancer is colorectal cancer (e.g., advanced colorectal cancer, metastatic colorectal cancer, MSS colorectal cancer, MSI-H colorectal cancer, or POLE mutant colorectal cancer). In some embodiments, a patient population includes one or more subjects (e.g., comprises or consists of subjects) suffering from cancer. For example, in some embodiments, a patient population suffering from cancer may have previously been treated with a prior therapy, for example, radiation and/or chemotherapy.

In some embodiments, the pharmacokinetic parameter(s) can be any parameters suitable for describing the present composition.

In some embodiments, the pharmacokinetic parameter(s) can be any parameters suitable for describing the present composition. For example, in some embodiments, the $C_{max}$ is about 1 µg/ml; about 5 µg/ml, about 10 µg/ml, about 15 µg/ml, about 20 µg/ml, about 25 µg/ml, about 30 µg/ml, about 35 µg/ml, about 40 µg/ml, about 45 µg/ml, about 50 µg/ml, about 55 µg/ml, about 60 µg/ml, about 65 µg/ml, about 70 µg/ml, about 75 µg/ml, about 80 µg/ml, about 85 µg/ml, about 90 µg/ml, about 95 µg/ml, about 100 µg/ml, about 150 µg/ml, about 200 µg/ml, about 250 µg/ml, about 300 µg/ml, or any other $C_{max}$ appropriate for describing a pharmacokinetic profile of an anti-TIM-3 antibody.

In some embodiments, the $T_{max}$ is, for example, not greater than about 0.5 hours, not greater than about 1.0 hours, not greater than about 1.5 hours, not greater than about 2.0 hours, not greater than about 2.5 hours, or not greater than about 3.0 hours, or any other $T_{max}$ appropriate for describing a pharmacokinetic profile of an anti-TIM-3 antibody.

In general, AUC as described herein is the measure of the area under the curve that corresponds to the concentration of an analyte over a selected time period following administration of a dose of a therapeutic agent. In some embodiments, such time period begins at the dose administration (i.e., 0 hours after dose administration) and extends for about 2, about 6, about 12, about 36, about 48, about 72, about 168, about 336, about 514, about 682, or more hours after the dose administration. In some embodiments, AUC is that achieved from 0 hours to 336 hours following administration of a dose described herein.

The $AUC_{(0-336h)}$ can be, for example, about 500 µg·hr/mL, about 1000 µg·hr/mL, about 1500 µg·hr/mL, about 2000 µg·hr/mL, about 2500 µg·hr/mL, about 3000 µg·hr/mL, about 3500 µg·hr/mL, about 4000 µg·hr/mL, about 4500 µg·hr/mL, about 5000 µg·hr/mL, about 7500 µg·hr/mL, about 10,000 µg·hr/mL, about 15,000 µg·hr/mL, about 20,000 µg·hr/mL, about 25,000 µg·hr/mL, about 30,000 µg·hr/mL, about 35,000 µg·hr/mL, about 40,000 µg·hr/mL, about 45,000 µg·hr/mL, about 50,000 µg·hr/mL, about 65,000 µg·hr/mL, about 75,000 µg·hr/mL, about 90,000 µg·hr/mL, or any other $AUC_{(0-336h)}$ appropriate for describing a pharmacokinetic profile of a therapeutic agent (e.g., an anti-TIM-3 antibody). In some embodiments, an anti-TIM-3 antibody is administered according to a regimen that is demonstrated to achieve an average $AUC_{0-336h}$ of the anti-TIM-3 antibody concentration-time curve in a patient population that is within 2500 h*µg/mL to 50000 µg/mL.

In some embodiments, the AUC from 0 hours to the end of the dosing period is determined ($AUC_{(0-Tau)}$). In some embodiments, the dosing period is one week, two weeks, three weeks, four weeks, five weeks, six weeks, seven weeks, eight weeks, nine weeks or ten weeks. In some embodiments, the dosing period is 2 weeks. In some embodiments, the dosing period is 3 weeks.

In some embodiments, an anti-TIM-3 antibody is administered according to a regimen demonstrated to achieve a response rate in relevant patient population such that no more than 50% to 80% of patients show progressive disease after 2, 4, 6, 8, 10, 12, 14, 16, 18, or 20 weeks following initiation of treatment. In some embodiments, no more than 80% of patients show progressive disease after at least 10 weeks following initiation of treatment.

In some embodiments, an anti-TIM-3 antibody is administered according to a regimen that is sufficient to achieve an average TIM-3 receptor occupancy of at least 50% to 90% after 1, 2, 3, 4, or 5 days following a single dose of the composition. In some embodiments, administration of a composition that delivers an anti-TIM-3 antibody sufficient to achieve an average TIM-3 receptor occupancy of at least 50%, at least 55%, at least 60%, at least 65%, at least 70%, at least 75%, at least 80%, at least 85%, or at least 90% after 3 days following a single dose of the composition.

In some embodiments, an anti-TIM-3 antibody is administered according to a regimen sufficient to achieve an average stimulation ratio of at least 1 in a functional TIM-3 receptor occupancy assay after 3 days following a single dose of the TIM-3-binding agent.

In some embodiments, an anti-TIM-3 antibody is administered according to a regimen sufficient to achieve an average TIM-3 receptor occupancy of at least 75% over a first period of time, e.g., about 14 days to about 60 days following a single dose of the anti-TIM-3 antibody t. In some embodiments, an anti-TIM-3 antibody is administered according to a regimen sufficient to achieve an average TIM-3 receptor occupancy of at least 75% over the first period of time (e.g., about 15 days to about 60 days; in some embodiments about 29 days) following a single dose of the anti-TIM-3 antibody.

In some embodiments, an anti-TIM-3 antibody is administered according to a regimen sufficient to achieve an average stimulation ratio of at least 1 in a functional TIM-3 receptor occupancy assay over a first period of time, e.g., about 14 days to about 60 days following a single dose of the anti-TIM-3 antibody. In some embodiments, an anti-TIM-3 antibody is administered according to a regimen sufficient to achieve an average stimulation ratio of at least 1 in a functional TIM-3 receptor occupancy assay over the first period of time (e.g., about 15 days to about 60 days; in some embodiments about 29 days) following a single dose of the anti-TIM-3 antibody.

EXAMPLES

The following examples are provided to illustrate, but not limit the claimed invention.

Example 1

Combinatorial Blockade of TIM-3 and PD-1 in Mouse Model Systems

Figure 2A:
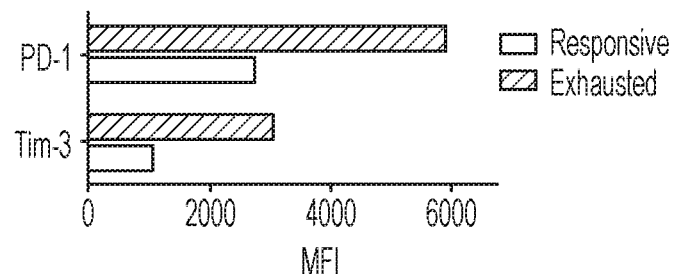
FIGS. 2A-2B depict results from an exemplary T cell exhaustion model. (A) Target expression of PD-1 and TIM-3 in responsive (pre-stimulated) cells and exhausted (post-stimulated cells). (B) Quantification of IFNγ production in exhausted (post-stimulated) cells treated with a combination of an anti-PD-1 antibody agent and an anti-TIM-3 antibody agent, an anti-PD-1 antibody agent, an anti-TIM-3 antibody agent, and isotype control.
Figure 2B:
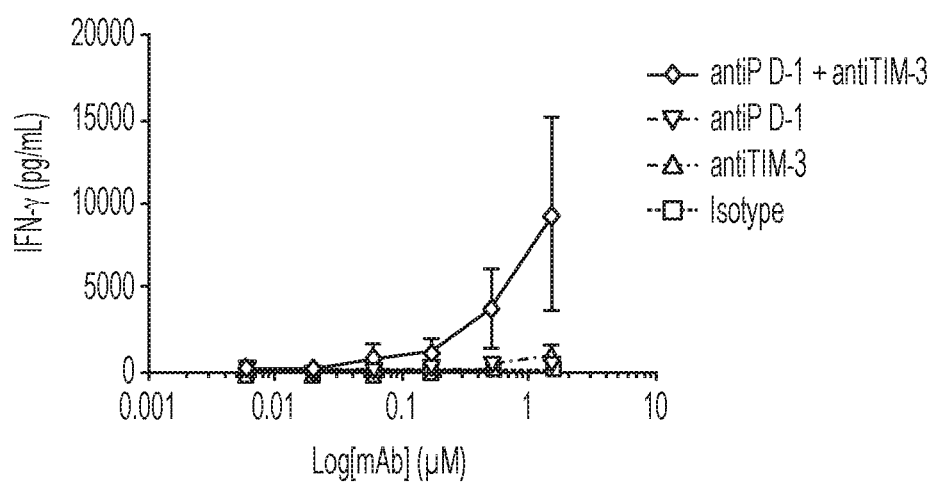

The effect of TIM-3 and PD-1 inhibition in a mouse T cell exhaustion assay was studied (Burkhart et al. *Int Immunol.* 1999; 11:1625-1634). In this system, in vitro stimulation of mouse CD4+ T cell receptor transgenic T cells with a super-agonist altered-peptide ligand leads to an exhausted phenotype, characterized by increased expression of PD-1 and TIM-3 (FIG. 2A). As shown in FIG. 2B, the combination of anti-PD-1 and anti-TIM-3 antibodies was more effective than either agent alone in enhancing the production of IFNγ in this system.

Example 2

In Vivo Efficacy Study of TSR-042 and TSR-022 Combination

Figure 3:
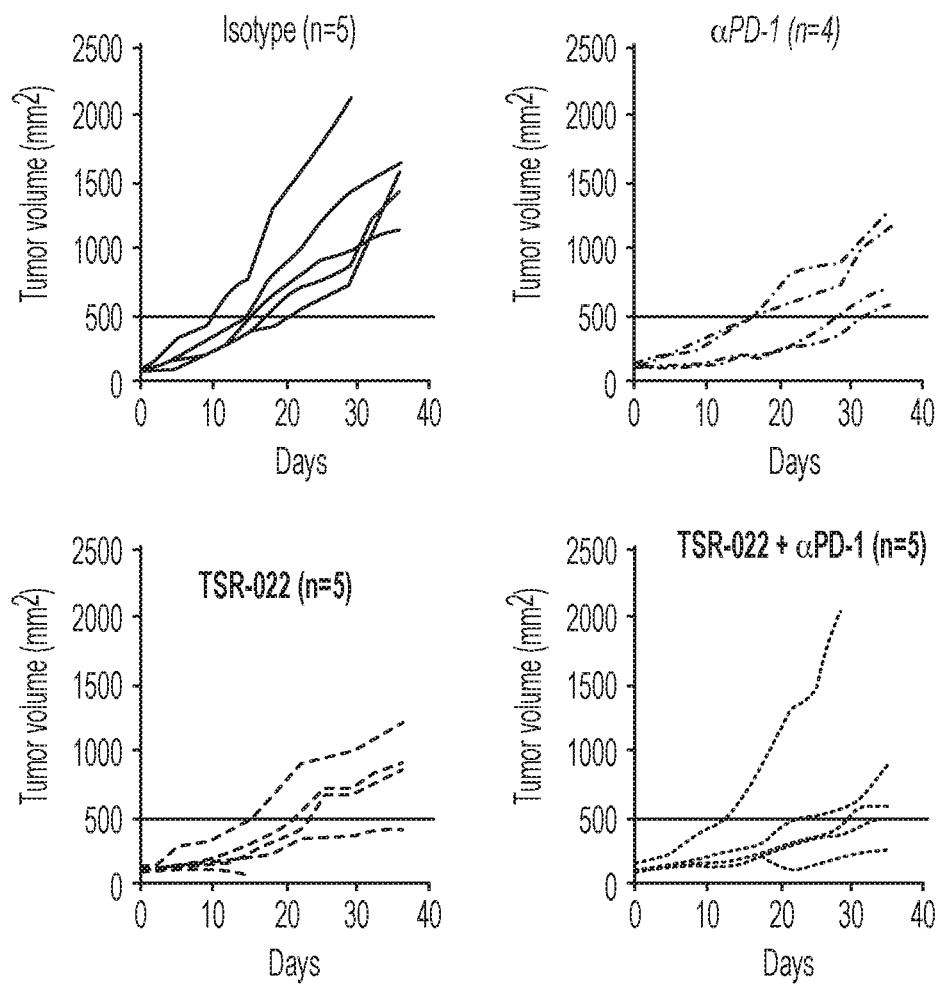
FIG. 3 depicts results from an in vivo efficacy study of a combination of an exemplary anti-PD-1 antibody (TSR-042) and an exemplary anti-TIM-3 antibody (TSR-022) antibodies. In the study, huNOG-EXL mice transplanted neonatally with CD34+ hematopoietic stem cells were implanted with A549 NSCLC cells and treated with single agents and combinations of anti-PD-1 and anti-TIM-3 antibodies.

In addition to evaluating the combinatorial effect of targeting PD-1 and TIM-3 in vitro, the combination was tested in an animal model of lung cancer. A humanized mouse tumor model was employed, consisting of A549 human lung cancer cells ($5 \times 10^6$ cells per mouse) implanted into huNOG-EXL mice. Neonatally derived CD34+ hematopoietic stem cells were engrafted into the mouse, and animals were treated with monoclonal blocking antibodies targeting PD-1 (TSR-042) and TIM-3 (TSR-022). Here, we show that the combination of anti-PD-1 and anti-TIM-3 has a beneficial antitumor effect when compared to either agent alone (FIG. 3).

Example 3

Dosing Regimens for an Exemplary TIM-3-Binding Agent

This example describes a multicenter, open-label, first-in-human Phase 1 study evaluating a TIM-3 binding agent (an anti-TIM-3 antibody), in patients with tumors. Specifically the dosage effects in patients with advanced solid tumors treated with a particular TIM-3 binding agent. A TIM-3 binding agent (TSR-022) as described in the present study comprises a humanized monoclonal anti-TIM-3 antibody comprising a heavy chain whose amino acid sequence comprises SEQ ID NO: 3 and a light chain whose amino acid sequence comprises SEQ ID NO:4 are evaluated. This anti-TIM-3 antibody utilizes a human IGHG4*01 heavy chain gene, and a human IGKC*01 kappa light chain gene, as scaffolds. Further, there is a single Ser to Pro point mutation in the hinge region of the IgG4 heavy chain at the canonical S228 position.

Patients were included with histologically or cytologically proven advanced (unresectable) or metastatic solid tumor and who had disease progression after treatment with available therapies that are known to confer clinical benefit or who are intolerant to other known treatment(s).

The study comprises several parts: dose escalation and cohort expansion. Part 1a of the study (dose escalation) is intended, inter alia, to evaluate the safety, PK, and PDy profile, tolerability and anti-cancer effect of the anti-TIM-3 antibody. A modified 3+3 design was used for dose escalation at 0.03 mg/kg, 0.1 mg/kg, 0.3 mg/kg, 1.0 mg/kg, 3 mg/kg, and 10 mg/kg and higher every 2 weeks (Q2W) with the dose of the TIM-3 antibody not to exceed 20 mg/kg. Dose escalation has continued to 1.0 mg/kg Q2W and a MTD has not yet been identified. Part 1a could also comprise the testing of a "flat" dose, or a specific fixed number of milligrams of antibody (as opposed to the weight based dosing mg/kg). Flat doses could range from 200 mg to 1500 mg of anti-TIM-3 antibody. Part 1b of the study (combination with PD1 dose escalation cohorts) is intended, inter alia, to evaluate the safety, PK, and PDy profile, tolerability and anti-cancer effect of the anti-TIM-3 antibody in combination with an anti-PD-1 antibody wherein the anti-TIM-3 antibody is administered as a dose escalation. Dosing will comprise anti-TIM-3 at 1.0 mg/kg, 3 mg/kg, and 10 mg/kg or higher every 2 weeks (Q2W) or every 3 weeks (Q3W) with the dose of anti-TIM-3 to not exceed the MTD defined in part 1a of the study each in combination with an anti-PD-1 (exemplary anti-PD-1 antibodies are a humanized monoclonal anti-PD-1 antibody comprising a heavy chain whose amino acid sequence comprises SEQ ID NO: 13 and a light chain whose amino acid sequence comprises SEQ ID NO:14 nivolumab, or pembrolizumab). The anti-PD-1 antibody can be dosed at an approved dose and schedule for a marketed agent and on a weight basis at a dose of 3 or 10 mg/kg Q2W or Q3W or on a flat dose basis of 500 mg antibody Q2W or Q3W by using a modified 3+3 design.

Primary endpoints include determining the safety and tolerability of TSR-022 by Common Terminology Criteria for Adverse Events (CTCAE v4) and to determine the recommended phase 2 dose (RP2D) and schedule for monotherapy and combination with an anti-PD-1 antibody. Secondary endpoints include: pharmacokinetics (PK), overall response rate, duration of response, disease control rate, progression-free survival, overall survival, and immunogenicity. Exploratory endpoints include pharmacodynamics.

Figure 4A:
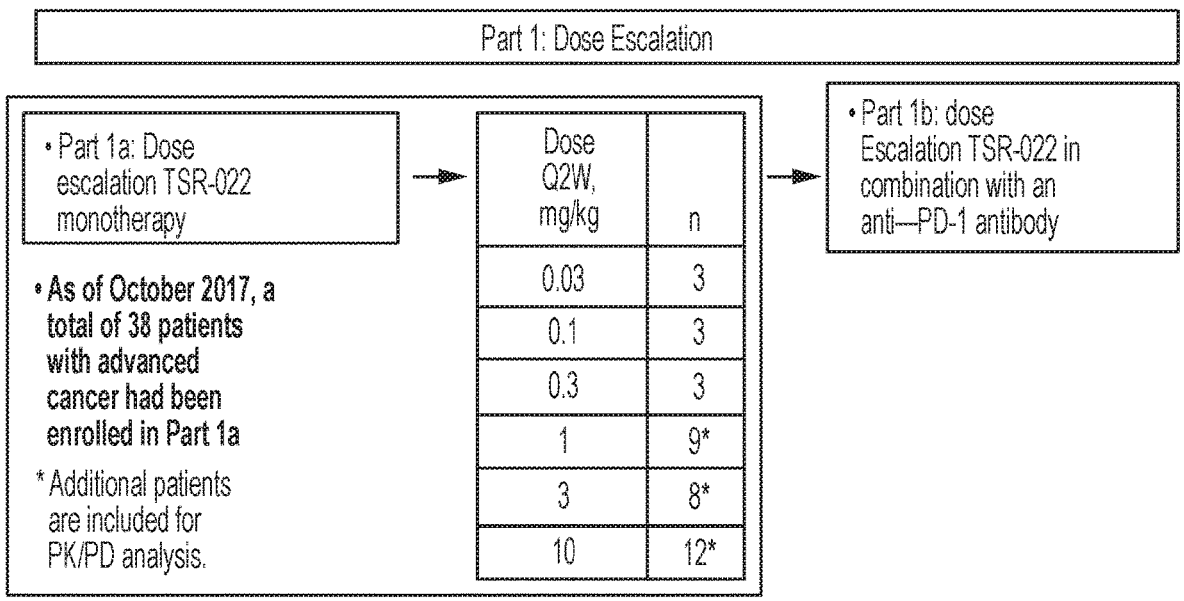
FIG. 4A relates to a dose escalation study for an exemplary anti-TIM-3 antibody (TSR-022) as monotherapy or in combination with an anti-PD-1 antibody.

FIG. 4A shows doses used in the dose escalation study of Part 1a for TSR-022 monotherapy. In the dose escalation study, 38 patients with advanced cancer had been enrolled as of October 27. Doses of 0.03 mg/kg, 0.1 mg/kg, 0.3 mg/kg, 1 mg/kg, 3 mg/kg, and 10 mg/kg were administered to patients.

Adult patients with advanced or metastatic solid tumors who have disease progression or treatment in tolerance after treatment with available therapies and having adequate organ function and ECOG [Eastern Cooperative Oncology Group] performance status were treated. Prior treatment with immune checkpoint inhibitors was permitted. A summary of patient demographics is shown in FIG. 5 for the 38 patients enrolled. In the Part 1a study, there were 21 male patients and 17 female patients. The mean age was 60.1 years (SD=13.5), with a median of 61.0 years (min=25; max=85). The mean number of prior treatment lines was 3.2 (SD=2.3), with a median of 2.0 (min=1; max=10). 10 patients had an ECOG performance status of 0, and 28 had an ECOG performance status of 1. Tumor sites included colon, skin, ovary, breast, brain, head and neck, testis, pleura, lung, rectum, thyroid, liver, or esophagus.

Figure 6A:
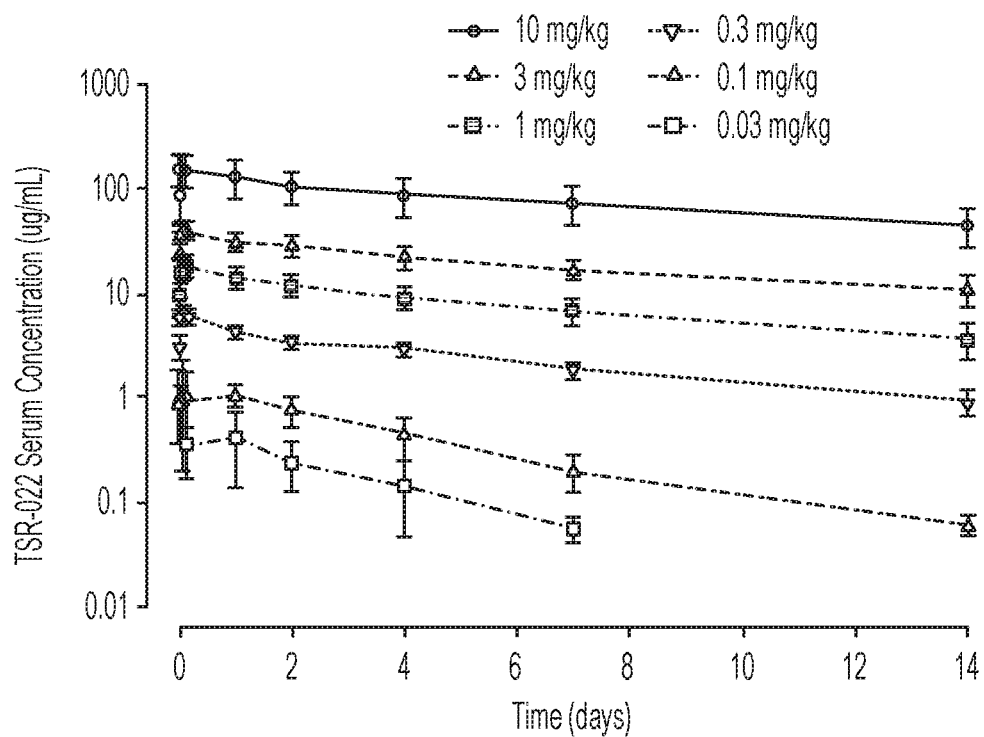
FIG. 6A depicts mean PK profiles of an exemplary anti-TIM-3 antibody (TSR-022) after the first dose.

After patients received the first dose of TSR-022 at various levels (0.03-10 mg/kg), the TSR-022 concentration in serum was monitored for two weeks and the pharmacokinetic (PK) behaviors were characterized. FIG. 6A shows serum concentration versus time profiles for all treatment groups in Part 1. TSR-022 demonstrated linear PK behavior for the studied doses of 0.03-10 mg/kg.

Figure 6B:
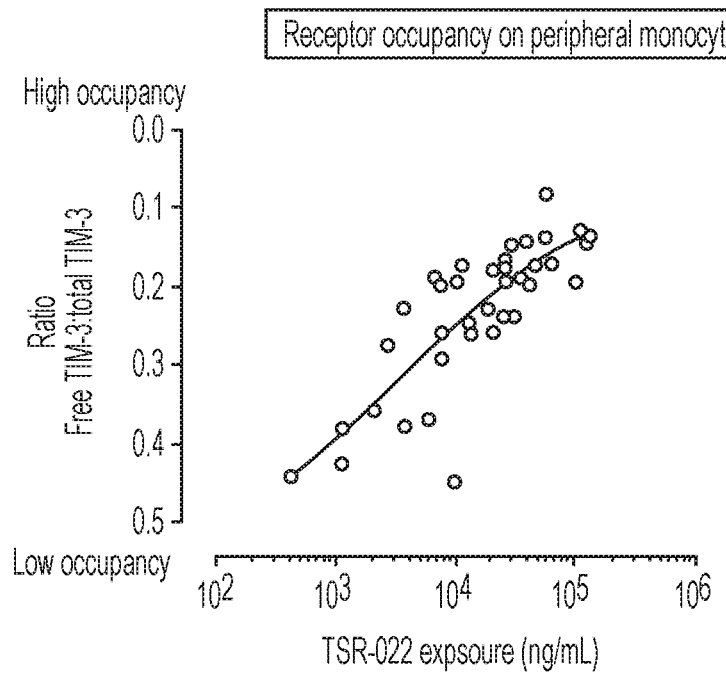
FIG. 6B depicts TIM-3 occupancy on circulating monocytes as measured by flow cytometry from whole blood samples collected from patients treated with an exemplary anti-TIM-3 antibody (TSR-022).

FIG. 6B shows TIM-3 occupancy on circulating monocytes as measured by flow cytometry from whole blood samples collected from patients treated with anti-TIM-3. Receptor occupancy on peripheral monocytes was shown to correlate with TSR-022 exposure.

TIM-3 receptor occupancy (RO) by TSR-022 on circulating $CD14^+$ monocytes was measured by flow cytometry. Briefly, whole blood samples from patients treated with TSR-022 were stained with anti-CD14, a non-competing anti-TIM-3 antibody (indicating total TIM-3) and a competing anti-TIM-3 antibody (indicating unbound or free TIM-3). TIM-3 occupancy by infused TSR-022 was estimated as the ratio of free TIM-3 on CD14+ cells to the total TIM-3 on CD14+ cells. A decrease in the ratio indicates an increase in TSR-022 bound TIM-3 receptor. To measure binding in the RO assay, whole blood was collected from patients at baseline (Day 1 predose), 48 hours following the first dose (Day 3) and prior to the second dose (Day 15 predose) for the Q2W schedule. Additional samples were collected on Day 22 and Day 29 following the first dose for a subset of patients who did not receive the second dose. Samples for occupancy measurement on the Q3W schedule were collected as follows: Day 1 predose, Day 5, Day 15 and Day 22. Ex vivo TSR-022 saturated healthy donor samples ("sat") as well as controls lacking detection antibodies ("Bkgd") were included as controls.

Figure 7A:
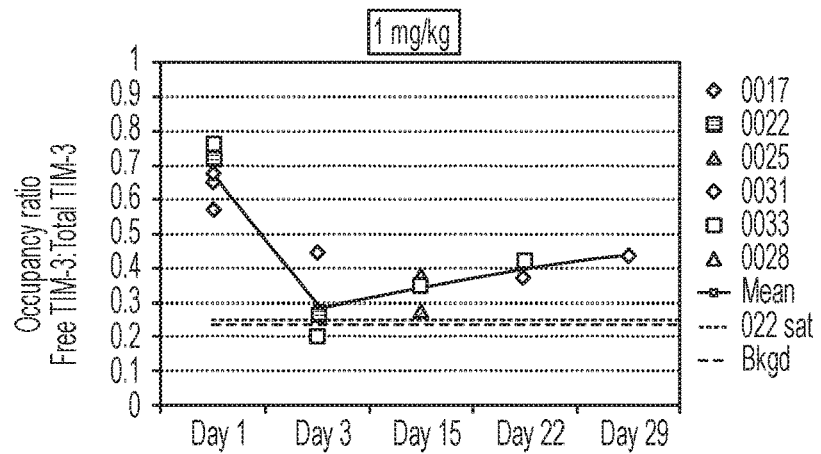
FIGS. 7A-7C depict TIM-3 receptor occupancy for an exemplary anti-TIM-3 antibody (TSR-022) at doses of 1 mg/kg (FIG. 7A), 3 mg/kg (FIG. 7B), and 10 mg/kg (FIG. 7C) administered once every two weeks (Q2W).
Figure 7B:
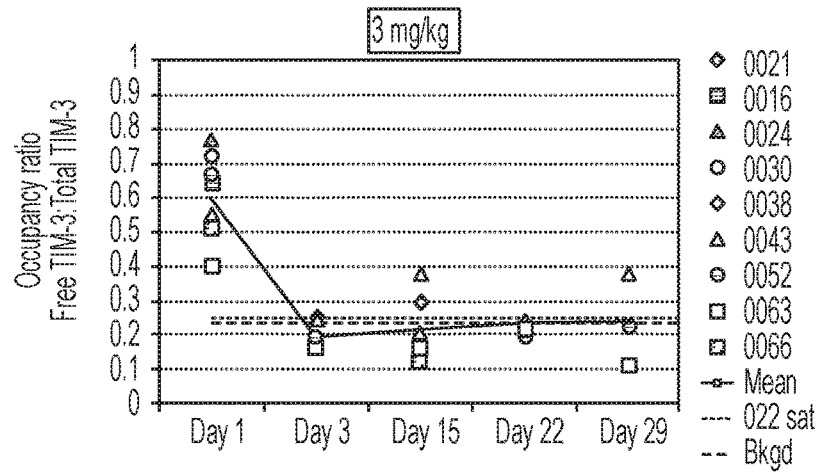
Figure 7C:
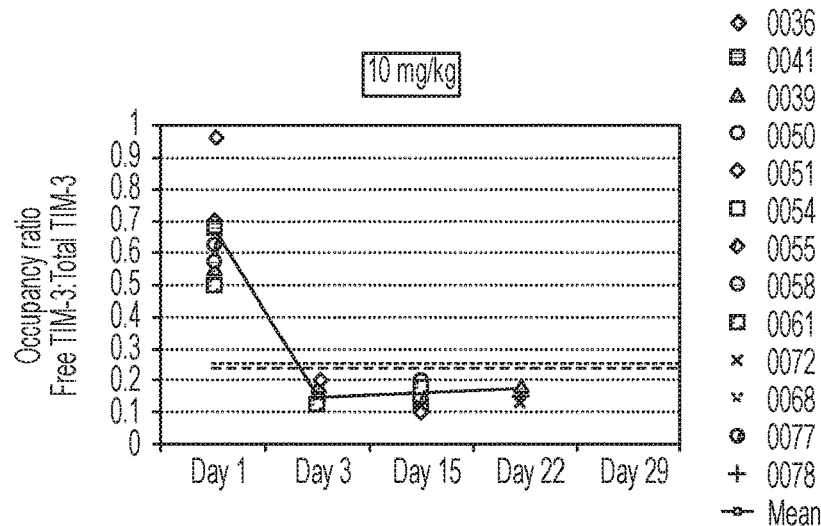

FIGS. 7A-7C respectively show receptor occupancy studies of the anti-TIM-3 antibody (TSR-022) administered at doses of 1 mg/kg (FIG. 7A), 3 mg/kg (FIG. 7B), and 10 mg/kg (FIG. 7C) every two weeks (Q2W). All samples were pre-dose, with occupancy measured after a single dose on day 1. The occupancy ratio (free TIM-3:total TIM-3) is determined at various time points (for example, timepoints can include day 1, day 3, day 15, day 22, and day 29). The receptor occupancy is maximal on day 3 across doses of TSR-022. At 3 mg/kg, maximal occupancy is maintained through day 29, and comparable results are obtained for the 10 mg/kg dose through the days of available data.

Figure 8:
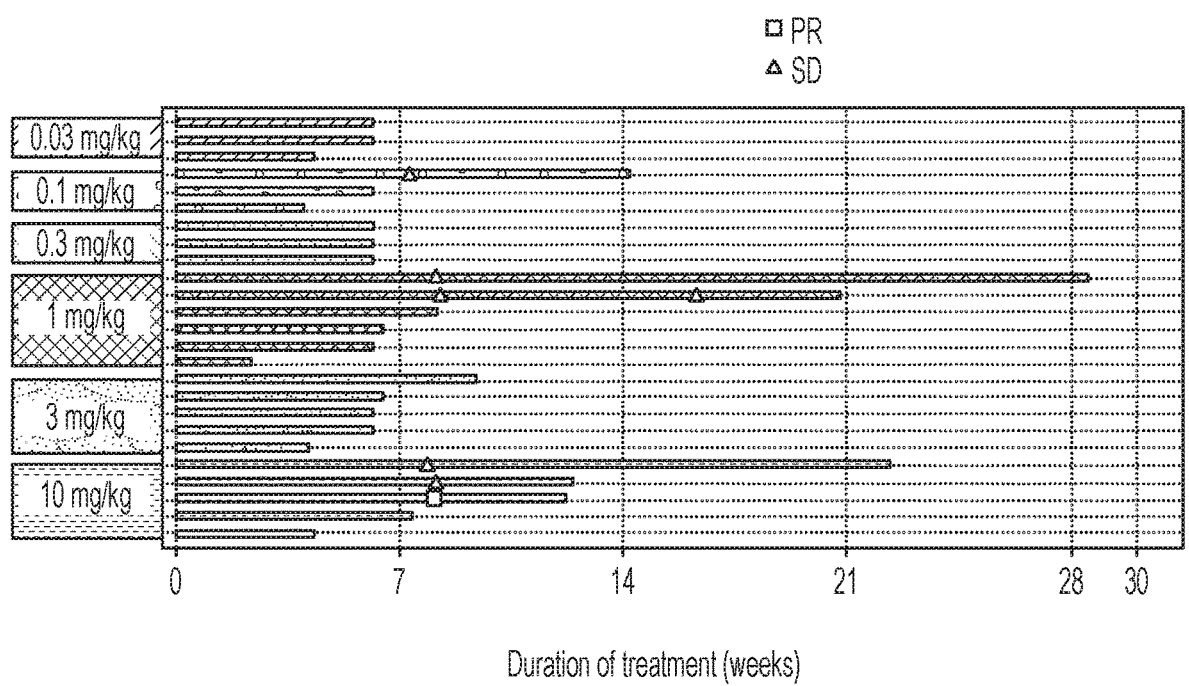
FIG. 8 depicts the effects of treatment with an exemplary anti-TIM-3 antibody (TSR-022). Duration of treatment associated with specific dosages are shown, and a partial response is noted by black squares and stable disease is noted by black triangles.

FIG. 8 provides a summary of dosages administered to patients (0.03-10 mg/kg) and the duration of treatment during the Part 1a studies.

The best response observed was also evaluated in efficacy evaluable patients (e.g., patients who received at least two doses and either had at least one post-baseline assessment or had discontinued treatment due to clinical progression prior to post-baseline tumor assessment. Stable disease (5/25 patients) and partial response (1/25 patients at 10 mg/kg) were observed as the best response in patients with rectal, thyroid, neuroendocrine, or head and neck cancer, or with soft tissue sarcoma.

Figure 9:
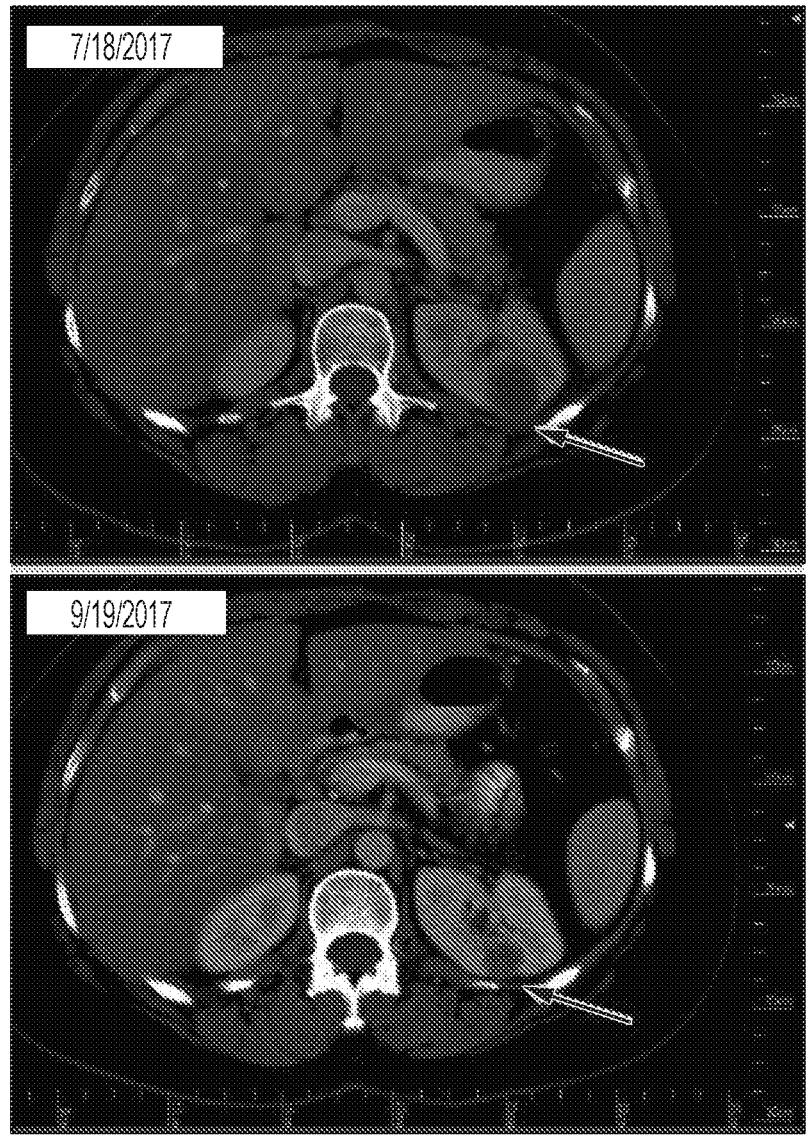
FIG. 9 depicts the brain scan of a patient with leiomyosarcoma, metastatic to the lung and kidney and who received three doses of an exemplary anti-TIM-3 antibody (TSR-022) at 10 mg/kg prior to re-staging imaging.

FIG. 9 depicts brain scans from the patient with partial response at the 10/mg level. The patient is 42 years old with leiomyosarcoma that is metastatic to lung and kidney (kidney biopsy confirmed leiomyosarcoma: PTEN splice site, MYC amplification, ATRX mutation, CD36 mutation, RB loss, p53 loss; low mutation burden). The patient received 3 doses of TSR-022 at 10 mg/kg before re-staging imaging. Additionally, the patient received gemcitabine and docetaxel for 5 months with demonstrated progression before entering the study. Pending confirmatory imaging, there appears to be a 32% tumor reduction at the 10 mg/kg dose level, and treatment is ongoing.

From the studies, TSR-022 monotherapy has been shown to be well-tolerated across multiple dose levels.

Part 2 of the study is intended, inter alia, are to evaluate safety and tolerability, PK, and PDy profile and anti-cancer effect of (i) the anti-TIM-3 antibody at fixed doses Q2W or Q3W or (ii) anti-TIM-3 antibody at fixed doses Q2W or Q3W in combination with anti-PD-1 antibodies at weight based or flat doses as indicated above. An anti-PD-1 antibody can be administered according to a regimen of 500 mg every three weeks (Q3W) for the initial treatment cycles (e.g., 500 mg administered Q3W for four treatment cycles) followed by administration of 1000 mg administered every six weeks (Q6W) until treatment is discontinued (e.g., due to disease progression).

Flat doses of about 100 mg to 1500 mg of the anti-TIM-3 antibody can be administered in monotherapy or in combination therapy. For example, a dose of about 100 mg, 200 mg, 300 mg, 400 mg, 500 mg, 600 mg, 700 mg, 800 mg, 900 mg, 1000 mg, 1100 mg, 1200 mg, 1300 mg, 1400 mg, or 1500 mg of the anti-TIM-3 antibody can be administered Q1W, Q2W, Q3W, Q4W, Q5W, or Q6W as monotherapy or in combination with an anti-PD-1 antibody that is administered 500 mg Q3W for four treatment cycles then as 1000 mg Q6W until treatment is discontinued (e.g., due to disease progression). In embodiments, a dose of about 100 mg, 200 mg, 300 mg, 400 mg, 500 mg, 600 mg, 700 mg, 800 mg, 900 mg, 1000 mg, 1100 mg, 1200 mg, 1300 mg, 1400 mg, or 1500 mg of the anti-TIM-3 antibody can be administered Q2W or Q3W as monotherapy or in combination with an anti-PD-1 antibody that is administered 500 mg Q3W for four treatment cycles then as 1000 mg Q6W until treatment is discontinued (e.g., due to disease progression). A 100 mg, 200 mg, 300 mg, 500 mg, 800 mg, 1000 mg, or 1200 mg dose of the anti-TIM-3 antibody can be administered as a monotherapy once each week (Q1W), once every two weeks (Q2W), once every three weeks (Q3W), once every four weeks (Q4W), once every five weeks (Q5W), or once every three weeks (Q6W). A 100 mg, 200 mg, 300 mg, 500 mg, 800 mg, 1000 mg, or 1200 mg dose of the anti-TIM-3 antibody can be administered as a monotherapy once every two weeks (Q2W) or once every three weeks (Q3W).

Figure 10:
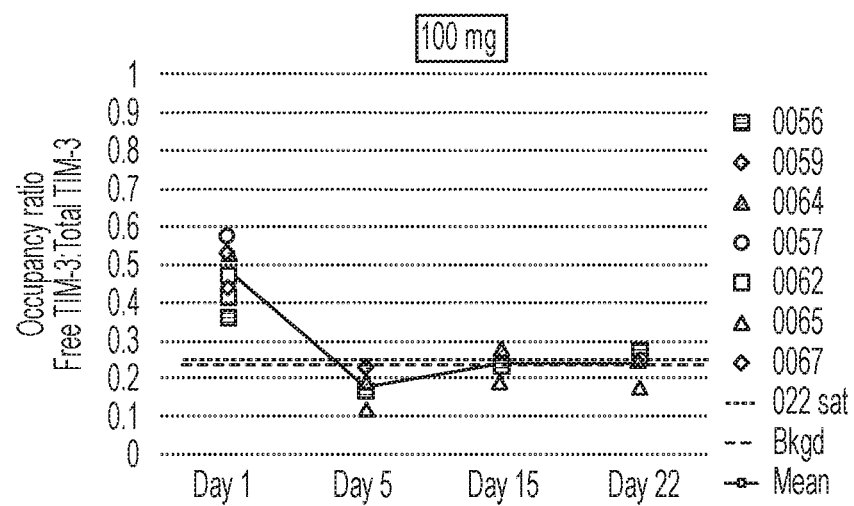
FIG. 10 depicts a receptor occupancy study of a 100 mg flat dose of an exemplary anti-TIM-3 antibody (TSR-022) administered once every three weeks (Q3W).

Receptor occupancy studies have been done based on a flat dose of 100 mg of the anti-TIM-3 antibody administered once every three weeks (Q3W). All samples were pre-dose, with occupancy measured after a single dose on day 1. As shown in FIG. 10, target coverage in the periphery is achieved at 100 mg for the duration of the dosing interval. Further, receptor occupancy at 100 mg Q3W is comparable to 3 mg/kg Q2W (FIG. 7B).

Figure 11:
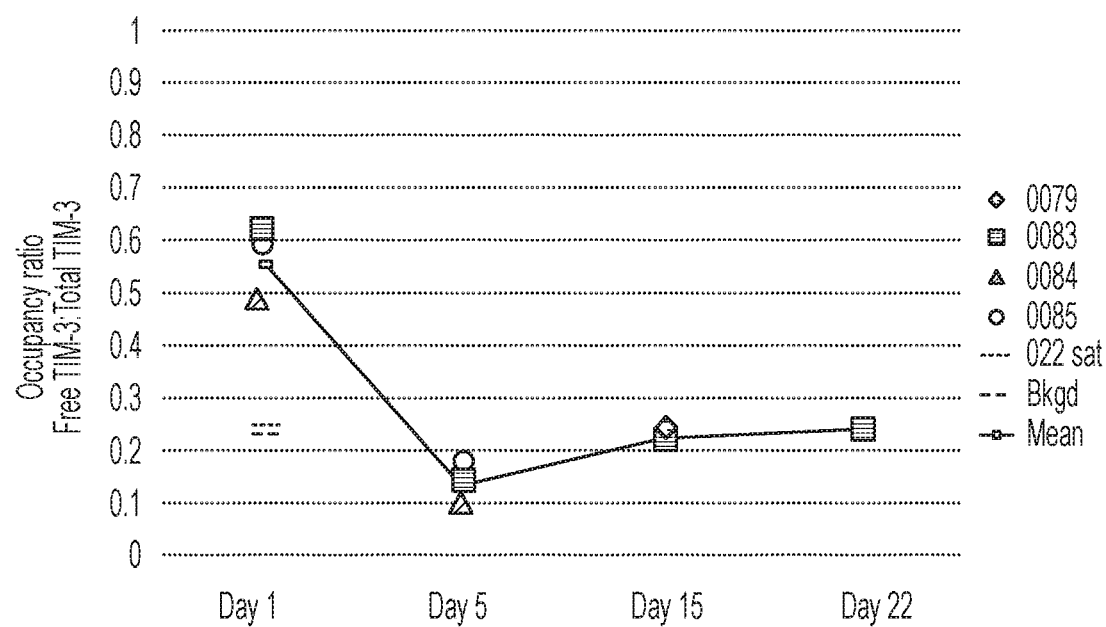
FIG. 11 depicts a receptor occupancy study of a 300 mg flat dose of an exemplary anti-TIM-3 antibody (TSR-022) administered in combination with a 500 mg flat dose of an exemplary anti-PD-1 antibody (TSR-042). A second dose of TSR-022 was administered on day 22, with the RO sample collected prior to the second dose.

Receptor occupancy studies following administration of a 300 mg flat dose of an exemplary anti-TIM-3 antibody (TSR-022) administered in combination with a 500 mg flat dose of an exemplary anti-PD-1 antibody (TSR-042) were also conducted according to methods described herein, and data are shown in FIG. 11. A second dose of the TSR-022 was administered on day 22, with the RO sample collected prior to the second dose. Using a flat dose of 300 mg TSR-022, high RO can be maintained over the measured time period.

Figure 12:
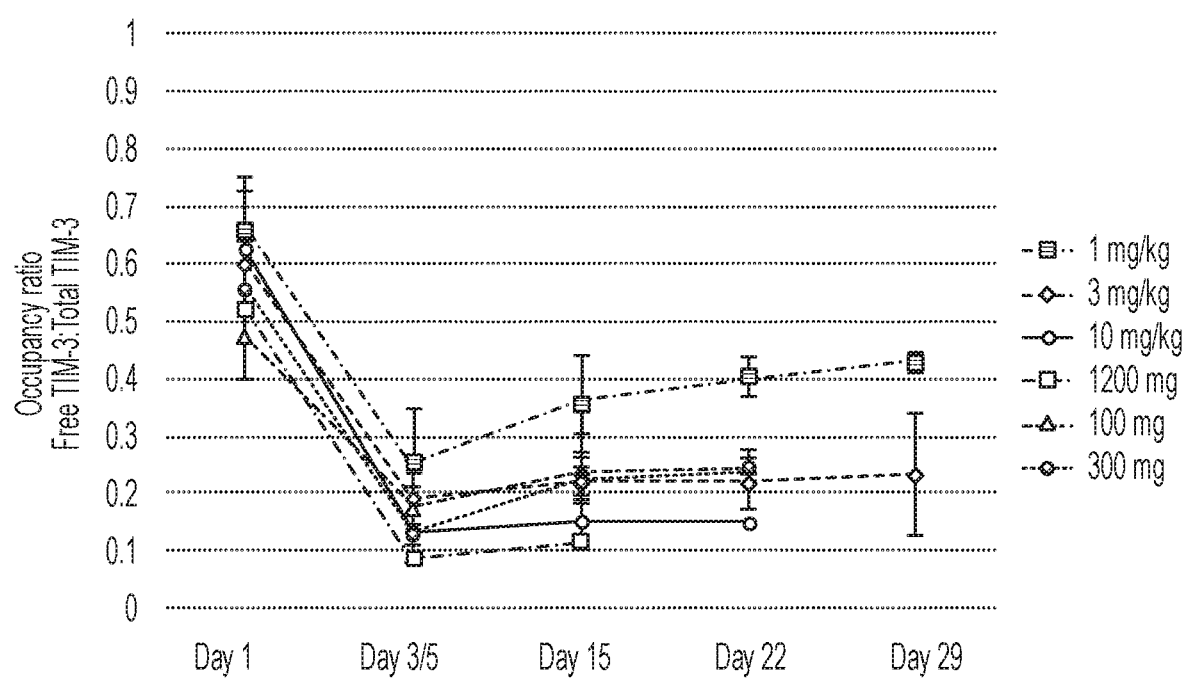
FIG. 12 is a composite of mean receptor occupancy data for doses of an exemplary anti-TIM-3 antibody (TSR-022) of 1 mg/kg, 3 mg/kg, 10 mg/kg and of flat doses of 100 mg, 300 mg, and 1200 mg. The figure shows the occupancy ratio (free TIM-3:total TIM-3) as measured over a range of days.

FIG. 12 is a composite of mean receptor occupancy data for doses of an exemplary anti-TIM-3 antibody (TSR-022) of 1 mg/kg, 3 mg/kg, 10 mg/kg and of flat doses of 100 mg, 300 mg, and 1200 mg. The figure shows that high occupancy ratios (free TIM-3:total TIM-3) can be achieved using various doses of TSR-022 as measured over a range of days.

Figure 4B:
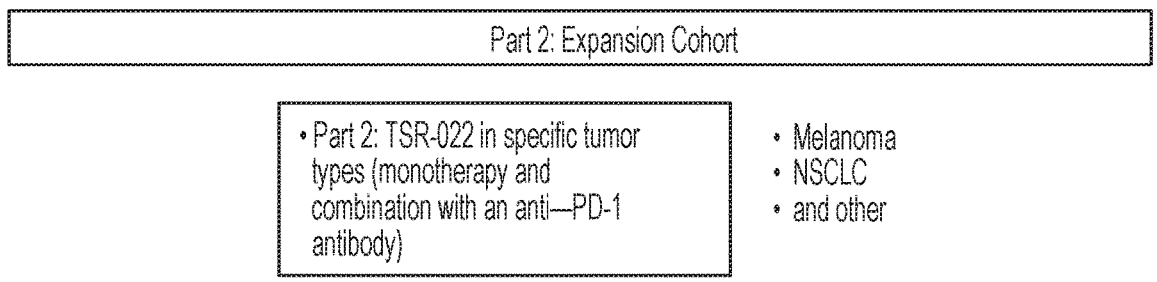
FIG. 4B relates to an expansion cohort in order to evaluate the anti-tumor activity of an exemplary anti-TIM-3 antibody (TSR-022) as a monotherapy and in combination with an anti-PD-1 antibody in patients with specific tumor types.

These monotherapy or combination regimens will be tested in specific tumor types, which may include anti-PD1/L1 treated melanoma, anti-PD1/L1 treated NSCLC, colorectal cancer, ovarian cancer, renal cell carcinoma, hepatocellular carcinoma, and/or breast cancer. FIG. 4B provides an overview of the Part 2 expansion cohort study.

Equivalents

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. A method of treating a lung cancer in a human subject, the method comprising: (i) administering, to the human subject, a flat dose of 300 mg, once every 3 weeks (Q3W), of an anti-TIM-3 antibody that comprises a heavy chain variable domain comprising SEQ ID NO: 1 and a light chain variable domain comprising SEQ ID NO:2; and, (ii) administering, to the human subject, an anti-Programmed Death-1 (anti-PD-1) antibody comprising a heavy chain comprising SEQ ID NO: 13 and a light chain comprising SEQ ID NO: 14, wherein the human subject has the lung cancer.

2. The method according to claim 1, wherein the anti-PD-1 antibody is administered at a flat dose of 500 mg Q3W to the human subject.

3. The method of claim 1, wherein the human subject is further administered a chemotherapeutic agent.

4. The method of claim 1, wherein the anti-TIM-3 antibody is administered to the human subject prior to the administration of the anti-PD-1 antibody.

5. The method of claim 4, wherein the anti-TIM-3 antibody is administered to the human subject 30 minutes prior to the administration of the anti-PD-1 antibody.

6. The method of claim 4, wherein the anti-TIM-3 antibody is administered to the human subject 45 minutes prior to the administration of the anti-PD-1 antibody.

7. The method of claim 1, wherein the anti-TIM-3 antibody and the anti-PD-1 antibody are administered intravenously to the human subject.

8. The method of claim 7, wherein the anti-TIM-3 antibody is present in a composition and is administered by intravenous infusion to the human subject.

9. The method of claim 1, wherein the lung cancer is a non-small cell lung cancer.

10. The method of claim 1, wherein the anti-TIM-3 antibody is administered to the human subject prior to the administration of the anti-PD-1 antibody, wherein the anti-TIM-3 antibody and the anti-PD-1 antibody are administered intravenously to the human subject, and wherein the lung cancer is a non-small cell lung cancer.

11. The method of claim 10, wherein the human subject is further administered a chemotherapeutic agent.

12. The method of claim 11, wherein the human subject is administered the anti-TIM-3 antibody before the administration of the chemotherapeutic agent.

13. A method of treating a non-small cell lung cancer in a human subject, the method comprising: (i) administering, to the human subject, a flat dose of 300 mg, once every 3 weeks (Q3W), of an anti-TIM-3 antibody that comprises a heavy chain variable domain comprising SEQ ID NO: 1 and a light chain variable domain comprising SEQ ID NO:2; (ii) administering, to the human subject, a flat dose of 500 mg, Q3W, of an anti-PD-1 antibody comprising a heavy chain comprising SEQ ID NO: 13 and a light chain comprising SEQ ID NO: 14; and, (iii) administering, to the human subject, a chemotherapeutic agent wherein the human subject has the non-small cell lung cancer.

\* \* \* \* \*

SEQUENCE LISTING

```
<160> NUMBER OF SEQ ID NOS: 26

<210> SEQ ID NO 1
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Gly Thr Tyr Thr Tyr Tyr Gln Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala

<210> SEQ ID NO 2
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg
            100                 105

<210> SEQ ID NO 3
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Lys Gly Leu Asp Trp
        35                  40                  45

Val Ser Thr Ile Ser Gly Gly Gly Thr Tyr Thr Tyr Tyr Gln Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
        340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 4
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 5

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ala Ser Gly Phe Thr
            35                  40                  45

Phe Ser Ser Tyr Asp Met Ser Trp Val Arg Gln Ala Pro Gly Lys Gly
    50                  55                  60

Leu Asp Trp Val Ser Thr Ile Ser Gly Gly Gly Thr Tyr Thr Tyr Tyr
65                  70                  75                  80

Gln Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Ser Met Asp Tyr Trp Gly Gln Gly Thr Thr Val
    115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220
```

```
Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser Gln Glu Asp Pro Glu Val Gln Phe Asn
    275                 280                 285

Trp Tyr Val Asp Gly Val Glu Val His Asn Ala Lys Thr Lys Pro Arg
        290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
            325                 330                 335

Asn Lys Gly Leu Pro Ser Ser Ile Glu Lys Thr Ile Ser Lys Ala Lys
        340                 345                 350

Gly Gln Pro Arg Glu Pro Gln Val Tyr Thr Leu Pro Pro Ser Gln Glu
    355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Arg Leu Thr Val Asp Lys Ser Arg Trp Gln Glu Gly
        420                 425                 430

Asn Val Phe Ser Cys Ser Val Met His Glu Ala Leu His Asn His Tyr
    435                 440                 445

Thr Gln Lys Ser Leu Ser Leu Ser Leu Gly Lys
    450                 455

<210> SEQ ID NO 6
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Arg Arg Tyr Leu Asn Trp Tyr His Gln Lys Pro Gly Lys
    50                  55                  60

Ala Pro Lys Leu Leu Ile Tyr Gly Ala Ser Thr Leu Gln Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Val Tyr Tyr Cys Gln Gln
        100                 105                 110

Ser His Ser Ala Pro Leu Thr Phe Gly Gly Gly Thr Lys Val Glu Ile
    115                 120                 125
```

```
Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 7
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser
            20                  25                  30

Tyr Asp Met Ser Trp Val Arg Gln Ala Pro Gly Lys Gly Leu Asp Trp
            35                  40                  45

Val Ser Thr Ile Ser Gly Gly Thr Tyr Thr Tyr Tyr Gln Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
                100                 105                 110

Ser

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
            35                  40                  45

Tyr Gly Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

Glu Asp Phe Ala Val Tyr Tyr Cys Gln Gln Ser His Ser Ala Pro Leu
            85                  90                  95

Thr Phe Gly Gly Gly Thr Lys Val Glu Ile Lys
            100                 105

<210> SEQ ID NO 9
<211> LENGTH: 1320
<212> TYPE: DNA
<213> ORGANISM: Artificial Sequence
<220> FEATURE:
<223> OTHER INFORMATION: Synthetic Polynucleotide

<400> SEQUENCE: 9
gaggtgcagc tgttggagtc tgggggaggc ttggtacagc ctggggggtc cctgagactc      60
tcctgtgcag cagcctctgg attcactttc agtagctatg acatgtcttg ggtccgccag     120
gctccaggga aggggctgga ctgggtctca accattagtg gtggtggtac ttacacctac     180
tatcaagaca gtgtgaaggg gcggttcacc atctccagag acaattccaa gaacacgctg     240
tatctgcaaa tgaacagcct gagagccgag gacacggccg tatattactg cgtccatg      300 gactactggg gcaagggac cacggtcacc gtctcctcag catccaccaa gggcccatcg      360
gtcttcccgc tagcaccctg ctccaggagc acctccgaga gcacagccgc cctgggctgc     420
ctggtcaagg actacttccc cgaaccagtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660
ccatgcccag cacctgagtt cctggggggga ccatcagtct tcctgttccc cccaaaaccc     720
aaggacactc tcatgatctc ccggacccct gaggtcacgt gcgtggtggt ggacgtgagc     780
caggaagacc ccgaggtcca gttcaactgg tacgtggatg gcgtggaggt gcataatgcc     840
aagacaaagc cgcgggagga gcagttcaac agcacgtacc gtgtggtcag cgtcctcacc     900
gtcctgcacc aggactggct gaacggcaag gagtacaagt gcaaggtctc caacaaaggc     960
ctcccgtcct ccatcgagaa aaccatctcc aaagccaaag ggcagccccg agagccacag    1020
gtgtacaccc tgcccccatc ccaggaggag atgaccaaga accaggtcag cctgacctgc    1080
ctggtcaaag gcttctaccc cagcgacatc gccgtggagt gggagagcaa tgggcagccg    1140
gagaacaact acaagaccac gcctcccgtg ctggactccg acggctcctt cttcctctac    1200
agcaggctaa ccgtggacaa gagcaggtgg caggagggga atgtcttctc atgctccgtg    1260
atgcatgagg ctctgcacaa ccactacaca cagaagagcc tctccctgtc tctgggtaaa    1320

<210> SEQ ID NO 10
<211> LENGTH: 642
<212> TYPE: DNA
<213> ORGANISM: Artificial Sequence
<220> FEATURE:
<223> OTHER INFORMATION: Synthetic Polynucleotide

<400> SEQUENCE: 10
gacatccaga tgacccagtc tccatcctcc ctgtctgcat ctgtaggaga cagagtcacc      60
atcacttgcc gggcaagtca gagcattagg aggtatttaa attggtatca gcagaaacca     120
gggaaagccc ctaagctcct gatctatggt gcatccacct tgcaaagtgg ggtcccatca     180
aggttcagtg gtagtggatc tgggacagat ttcactctca ccatcagcag tctgcaacct     240

```
gaagattttg cagtgtatta ctgtcaacag agtcacagtg cccccctcac tttcggcgga      300
gggaccaagg tggagatcaa acgaactgtg gctgcaccat ctgtcttcat cttcccgcca      360
tctgatgagc aattgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctcagctcgc ccgtcacaaa gagcttcaac aggggagagt gt                        642
```

<210> SEQ ID NO 11
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala
        115
```

<210> SEQ ID NO 12
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 12

```
Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg
            100                 105
```

```
<210> SEQ ID NO 13
<211> LENGTH: 443
<212> TYPE: PRT
<213> ORGANISM: Artificial Sequence
<220> FEATURE:
<223> OTHER INFORMATION: Synthetic Polypeptide

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365
```

```
Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440

<210> SEQ ID NO 14
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 14

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 15

Met Glu Phe Gly Leu Ser Trp Leu Phe Leu Val Ala Ile Leu Lys Gly
1               5                   10                  15
```

Val Gln Cys Glu Val Gln Leu Leu Glu Ser Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Asp Met Ser Trp Val Arg Gln Ala Pro Gly Lys Gly Leu
 50                  55                  60

Glu Trp Val Ser Thr Ile Ser Gly Gly Gly Ser Tyr Thr Tyr Tyr Gln
65                   70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ser Pro Tyr Tyr Ala Met Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

```
Gln Glu Gly Asn Val Phe Ser Cys Ser Val Met His Glu Ala Leu His
            435                 440                 445
Asn His Tyr Thr Gln Lys Ser Leu Ser Leu Ser Leu Gly Lys
    450                 455                 460
```

<210> SEQ ID NO 16
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 16

```
Met Asp Met Arg Val Pro Ala Gln Leu Leu Gly Leu Leu Leu Leu Trp
1               5                   10                  15
Leu Pro Gly Ala Arg Cys Asp Ile Gln Leu Thr Gln Ser Pro Ser Phe
            20                  25                  30
Leu Ser Ala Tyr Val Gly Asp Arg Val Thr Ile Thr Cys Lys Ala Ser
        35                  40                  45
Gln Asp Val Gly Thr Ala Val Ala Trp Tyr Gln Gln Lys Pro Gly Lys
    50                  55                  60
Ala Pro Lys Leu Leu Ile Tyr Trp Ala Ser Thr Leu His Thr Gly Val
65                  70                  75                  80
Pro Ser Arg Phe Ser Gly Ser Gly Ser Gly Thr Glu Phe Thr Leu Thr
                85                  90                  95
Ile Ser Ser Leu Gln Pro Glu Asp Phe Ala Thr Tyr Tyr Cys Gln His
            100                 105                 110
Tyr Ser Ser Tyr Pro Trp Thr Phe Gly Gln Gly Thr Lys Leu Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 17
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 17

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met Ser Trp Val Arg Gln Ala Pro Gly Lys Gly Leu Glu Trp Val
        35                  40                  45
```

Ser Thr Ile Ser Gly Gly Ser Tyr Thr Tyr Tyr Gln Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Pro Tyr Tyr Ala Met Asp Tyr Trp Gly Gln Gly Thr Thr Val
                100                 105                 110

Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 18

Asp Ile Gln Leu Thr Gln Ser Pro Ser Phe Leu Ser Ala Tyr Val Gly
 1               5                  10                  15

Asp Arg Val Thr Ile Thr Cys Lys Ala Ser Gln Asp Val Gly Thr Ala
                20                  25                  30

Val Ala Trp Tyr Gln Lys Pro Gly Lys Ala Pro Lys Leu Leu Ile
             35                  40                  45

Tyr Trp Ala Ser Thr Leu His Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln His Tyr Ser Ser Tyr Pro Trp
                 85                  90                  95

Thr Phe Gly Gln Gly Thr Lys Leu Glu Ile Lys
                100                 105

<210> SEQ ID NO 19
<211> LENGTH: 1329
<212> TYPE: DNA
<213> ORGANISM: Artificial Sequence
<220> FEATURE:
<223> OTHER INFORMATION: Synthetic Polynucleotide

<400> SEQUENCE: 19
gaggtgcagc tgttggagtc tgggggaggc ttggtacagc ctggggggtc cctgagactc      60
tcctgtgcag cctctggatt cactttcagt agctatgaca tgtcttgggt ccgccaggct     120
ccagggaagg gctggagtg gtctcaacc attagtggtg gtggtagtta cacctactat      180
caagacagtg tgaaggggcg gttcaccatc tccagagaca attccaagaa cacgctgtat     240
ctgcaaatga acagcctgag agccgaggac acggccgtat attactgtgc gtccccttac     300
tatgctatgg actactgggg gcaagggacc acggtcaccg tctcctcagc atccaccaag     360
ggcccatcgg tcttccccct agcacccctgc tccaggagca cctccgagag cacagccgcc     420
ctgggctgcc tggtcaagga ctacttcccc gaaccagtga cggtgtcgtg aactcaggc     480 gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca agcccagcaa caccaaggtg gacaagagag ttgagtccaa atatggtccc     660

```
ccatgcccac catgcccagc acctgagttc ctgggggac catcagtctt cctgttcccc      720
ccaaaaccca aggacactct catgatctcc cggaccctg aggtcacgtg cgtggtggtg      780
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca aagccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggagagcaat     1140
gggcagccgg agaacaacta caagaccacg cctcccgtgc tggactccga cggctccttc     1200
ttcctctaca gcaggctaac cgtggacaag agcaggtggc aggagggaa tgtcttctca     1260 tgctccgtga tgcatgaggc tctgcacaac cactacacac agaagagcct ctccctgtct     1320
ctgggtaaa                                                           1329
```

<210> SEQ ID NO 20
<211> LENGTH: 642
<212> TYPE: DNA
<213> ORGANISM: Artificial Sequence
<220> FEATURE:
<223> OTHER INFORMATION: Synthetic Polynucleotide

<400> SEQUENCE: 20

```
gacatccagt tgacccagtc tccatccttc ctgtctgcat atgtaggaga cagagtcacc       60
atcacttgca aggccagtca ggatgtgggt actgctgtag cctggtatca gcaaaaacca      120
gggaaagccc ctaagctcct gatctattgg gcatccaccc tgcacactgg ggtcccatca      180
aggttcagcg gcagtggatc tgggacagaa ttcactctca caatcagcag cctgcagcct      240
gaagattttg caacttatta ctgtcagcat tatagcagct atccgtggac gtttggccag      300
gggaccaagc tggagatcaa acggactgtg gctgcaccat ctgtcttcat cttcccgcca      360
tctgatgagc aattgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacctgacg      540 ctgagcaaag cagactacga gaaacacaaa gtctacgcct gcgaagtcac ccatcagggc      600
ctcagctcgc ccgtcacaaa gagcttcaac aggggagagt gt                       642
```

<210> SEQ ID NO 21
<211> LENGTH: 10
<212> TYPE: PRT
<213> ORGANISM: Artificial Sequence
<220> FEATURE:
<223> OTHER INFORMATION: Synthietic Oligopeptide

<400> SEQUENCE: 21

Gly Phe Thr Phe Ser Ser Tyr Asp Met Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 22

```
Thr Ile Ser Gly Gly Thr Tyr Thr Tyr Tyr Gln Asp Ser Val Lys
1               5                   10                  15

<210> SEQ ID NO 23
<211> LENGTH: 3
<212> TYPE: PRT
<213> ORGANISM: Artificial Sequence
<220> FEATURE:
<223> OTHER INFORMATION: Synthetic Oligopeptide

<400> SEQUENCE: 23

Met Asp Tyr
1

<210> SEQ ID NO 24
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 24

Arg Ala Ser Gln Ser Ile Arg Arg Tyr Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 25

Gly Ala Ser Thr Leu Gln Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 26

Gln Gln Ser His Ser Ala Pro Leu Thr
1               5
```